(12) United States Patent  (10) Patent No.: US 8,609,700 B2
Soergel et al.  (45) Date of Patent: Dec. 17, 2013

(54) PYRIDINE COMPOUNDS FOR CONTROLLING INVERTEBRATE PESTS I

(75) Inventors: Sebastian Soergel, Ludwigshafen (DE);
Christian Defieber, Mannheim (DE);
Ronan Le Vezouet, Mannheim (DE);
Steffen Gross, Ludwigshafen (DE);
Karsten Koerber, Eppelheim (DE);
Deborah L. Culbertson, Fuquay Varina, NC (US); Douglas D. Anspaugh, Apex, NC (US)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 13/821,749

(22) PCT Filed: Sep. 12, 2011

(86) PCT No.: PCT/EP2011/065710
§ 371 (c)(1),
(2), (4) Date: Mar. 8, 2011

(87) PCT Pub. No.: WO2012/034961
PCT Pub. Date: Mar. 22, 2012

(65) Prior Publication Data
US 2013/0178502 A1 Jul. 11, 2013

Related U.S. Application Data

(60) Provisional application No. 61/382,043, filed on Sep. 13, 2010.

(51) Int. Cl.
*A01N 43/40* (2006.01)
*C07D 405/12* (2006.01)
*C07D 401/12* (2006.01)
*C07D 409/12* (2006.01)

(52) U.S. Cl.
USPC .................................. 514/343; 514/336

(58) Field of Classification Search
USPC ................................ 514/343, 336
See application file for complete search history.

(56) References Cited

U.S. PATENT DOCUMENTS

| 2002/0016337 | A1* | 2/2002 | Cuny et al. ............... 514/317 |
| 2004/0063765 | A1* | 4/2004 | Ammendola et al. ...... 514/353 |
| 2005/0101657 | A1* | 5/2005 | Furuya et al. ............. 514/423 |
| 2009/0156591 | A1* | 6/2009 | Ferrigno et al. .......... 514/231.2 |
| 2010/0305124 | A1 | 12/2010 | Fusslein et al. |
| 2011/0245239 | A1* | 10/2011 | Nanchen et al. .......... 514/227.8 |

FOREIGN PATENT DOCUMENTS

EP 1 466 902 10/2004

(Continued)

OTHER PUBLICATIONS

Begouin, Agathe, et al., "Palladium-Catalysed Muiticomponent Aminocarbonylation of Aryl or Heteroaryl Halides with [Mo(CO)6] and Aryl—or Heteroarylamines Using Conventional Heating", European Journal of Organic Chemistry, 2009, p. 2820-2827, vol. 2009, No. 17.

(Continued)

*Primary Examiner* — Raymond Henley, III
(74) *Attorney, Agent, or Firm* — Brinks Gilson & Lione

(57) ABSTRACT

The present invention relates to novel pyridine compounds of the formulae I and II, to their salts, to their tautomers, to their N-oxides, and to the salts of these N-oxides or tautomers. The compounds are useful for combating or controlling invertebrate pests, in particular arthropod pests. The invention also relates to a method for controlling invertebrate pests by using these compounds. The invention further relates to plant propagation material and to agricultural compositions comprising said compounds.

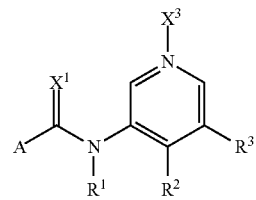

(I)

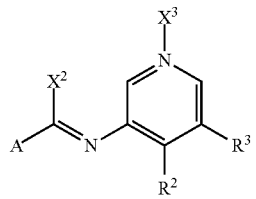

(II)

wherein A is a radical of the formulae A1 or A2

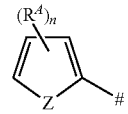

(A1)

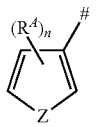

(A2)

# denotes the binding site to the remainder of formulae I or II;
n is 0, 1, 2 or 3;
Z is O, S or N—$R^N$;
$X^1$ is S, O or $NR^{1a}$;
$X^2$ is $OR^{2a}$, $NR^{2b}R^{2c}$, $S(O)_mR^{2d}$;
$X^3$ is a lone pair or oxygen;
$R^1$, $R^2$ and $R^3$ are, inter alia, hydrogen,
and $R^A$ and $R^N$, are as defined in claim 1.

19 Claims, No Drawings

(56) References Cited

FOREIGN PATENT DOCUMENTS

| | | |
|---|---|---|
| EP | 1 655 284 | 5/2006 |
| EP | 2 236 505 | 10/2010 |
| EP | 2 263 455 | 12/2010 |
| JP | 2004 331541 | 11/2004 |
| JP | 2009 78991 | 4/2009 |
| WO | WO 01/49664 | 7/2001 |
| WO | WO 01/53259 | 7/2001 |
| WO | WO 2007/029035 | 3/2007 |
| WO | WO 2008/000438 | 1/2008 |
| WO | WO 2008/074427 | 6/2008 |
| WO | WO 2009/027393 | 3/2009 |
| WO | WO 2010/034737 | 4/2010 |
| WO | WO 2010/034738 | 4/2010 |
| WO | WO 2010/070068 | 6/2010 |
| WO | WO 2010/112177 | 10/2010 |
| WO | WO 2011/003793 | 1/2011 |
| WO | WO 2011/003796 | 1/2011 |
| WO | WO 2011/009804 | 1/2011 |
| WO | WO 2011/057942 | 5/2011 |
| WO | WO 2011/117198 | 9/2011 |
| WO | WO 2011/117213 | 9/2011 |
| WO | WO 2011/117286 | 9/2011 |
| WO | WO 2011/117804 | 9/2011 |
| WO | WO 2011/117806 | 9/2011 |
| WO | WO 2012/034959 | 3/2012 |
| WO | WO 2012/034960 | 3/2012 |

OTHER PUBLICATIONS

Fors, B.P., et al., "An efficient system for the Pd-catalyzed cross-coupling of amides and aryl chlorides", Tetrahedron, 2009, p. 6576-6583, vol. 65.

Huitema, C., et al., "Heteroaromatic ester inhibitors of hepatitis A virus 3C proteinase: Evaluation of mode of action", Bioorganic & Medicinal Chemistry, 2008, p. 5761-5777, vol. 16.

Tangallapally, Rajendra, P., "Synthesis and Evaluation of Nitrofuranylamides as Novel Antituberculosis Agents", J. Med. Chem., 2004, p. 5276-5283, vol. 47.

Takashi, T. et al., "Synthesis of furan derivatives. I. Furamidines", 1948, p. 42-43, vol. 68, STN Database Accession No. 1950:10054 CAPLUS, Chemical Abstracts Service, Columbus, Ohio.

White, G. A., et al., "Furan carboxamide fungicides: structure-activity relationships with the succinate dehydrogenase complex in mitochondria from a wild-type strain and a carboxin-resistant mutant strain of Ustilago maydis", Pesticide Biochemistry and Physiology, 1988, p. 129-145, vol. 31, No. 2, STN Database Accession No. 1988:624591 CAPLUS, Chemical Abstracts Service, Columbus, Ohio.

International Search Report dated Oct. 20, 2011, prepared in International Application No. PCT/EP2011/065710.

International Preliminary Report on Patentability dated Dec. 6, 2012, prepared in International Application No. PCT/EP2011/065710.

Written Opinion of the ISA dated Aug. 30, 2012, prepared in International Application No. PCT/EP2011/065710.

\* cited by examiner

PYRIDINE COMPOUNDS FOR CONTROLLING INVERTEBRATE PESTS I

This application is a National Stage application of International Application No. PCT/EP2011/065710, filed Sep. 12, 2011, which claims the benefit of U.S. Provisional Application No. 61/382,043, filed Sep. 13, 2010, the entire contents of which are hereby incorporated herein by reference.

The present invention relates to novel pyridine compounds, to their salts, to their tautomers, to their N-oxides, and the salts of these N-oxides or tautomers which are useful for combating or controlling invertebrate pests, in particular arthropod pests and nematodes. The invention further relates to methods for controlling invertebrate pests by using these compounds. The invention further relates to a method for protecting plant propagation material and/or the plants which grow therefrom by using these compounds. The present invention further relates to plant propagation material and an agricultural composition comprising said compounds.

Invertebrate pests and in particular arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

WO 2008/074427 and WO 2008/000438 describe (het)arylcarbonylamino substituted six-membered (het)arenes which carry a carboxamide group in the meta-position of the carbonylamino substituent. The compounds are mentioned to be useful for combating invertebrate pests.

WO 2009/027393 and WO 2010/034737 describe pyrazolylcarbonylamino substituted pyridines, pyrimidines and triazines, which are mentioned to be useful for controlling invertebrate pests.

WO 2010/034738 describes compounds similar to those of WO 2009/027393 and WO 2010/034737 that have a heterocycle fused to the pyrazole moiety and that are also mentioned for controlling invertebrate pests.

JP 2009078991 describes preparation of thiophenecarboxyclic acids derivatives compounds and their respectively use as fungicide and glucokinase activators is mentioned. Example 206 relates to 5-trifluoromethylthiophene-2-carboxylic acid pyridin-3-ylamide.

WO 01/53259 relates to pyrrole carboxamide and pyrrole thioamide compounds as fungicides. WO 01/49664 relates to trifluoromethylpyrrole carboxamide and trifluoromethylpyrrole thioamide compounds as fungicides.

PCT/EP2010/001925 (WO 2010/112177), which was published after the priority date of the present invention, describes (het)arylcarbonylamino substituted pyridines and pyridazines including their use as insecticides.

It is an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by compounds of the formulae I and II, as defined below, including any possible stereoisomers of formulae I and II, by their salts, by their tautomers and by their N-oxides and by the salts of said tautomers and N-oxides, in particular their agriculturally or veterinarily acceptable salts.

Therefore, in a first aspect the present invention relates to pyridine compounds of formulae I or II,

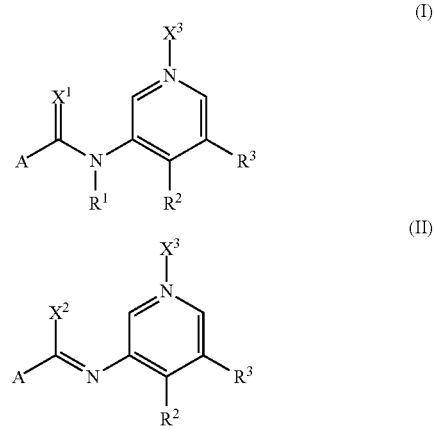

wherein
A is a radical of the formulae A1 or A2

where # denotes the binding site to the remainder of formulae I and II
n is 0, 1, 2 or 3;
Z is O, S or N—$R^N$;
$R^A$ is selected from the group consisting of halogen, CN, $NO_2$, $C_1$-$C_{10}$-alkyl, $C_2$-$C_{10}$-alkenyl and $C_2$-$C_{10}$-alkynyl, wherein the last three mentioned radicals may be unsubstituted, may be partially or fully halogenated or may carry 1, 2 or 3 identical or different substituents $R^x$, and also from the group consisting of $OR^a$, $C(Y)R^b$, $C(Y)OR^c$, $S(O)_mR^d$, $NR^eR^f$, $C_3$-$C_{10}$-cycloalkyl, $C_5$-$C_{10}$-cycloalkenyl, heterocyclyl, phenyl, $C_3$-$C_{10}$-cycloalkyl-$C_1$-$C_5$-alkyl, $C_5$-$C_{10}$-cycloalkenyl-$C_1$-$C_5$-alkyl, heterocyclyl-$C_1$-$C_5$-alkyl, hetaryl-$C_1$-$C_5$-alkyl, phenyl-$C_1$-$C_5$-alkyl and phenoxy-$C_1$-$C_5$-alkyl wherein the cyclic moieties of the ten last mentioned radicals may be unsubstituted or may carry 1, 2, 3, 4 or 5 identical or different substituents $R^y$; and
$R^N$ is selected from the group consisting of hydrogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, and also from the group consisting of $OR^a$, $C(Y)R^b$, $C(Y)OR^c$, $S(O)_mR^d$, $NR^eR^f$, $C(Y)NR^gR^h$, $S(O)_mNR^eR^f$, $C(Y)NR^iNR^eR^f$, $C_1$-$C_5$-alkylen-$OR^a$, $C_1$-$C_5$-alkylen-CN, $C_1$-$C_5$-alkylen-C(Y)$R^b$, $C_1$-$C_5$-alkylen-C(Y)O$R^c$, $C_1$-$C_5$-alkylen-N$R^e R^f$, $C_1$-$C_5$-alkylen-C(Y)N$R^g R^h$, $C_1$-$C_5$-alkylen-S(O)$_m R^d$, $C_1$-$C_5$-alkylen-S(O)$_m$N$R^e R^f$, $C_1$-$C_5$-alkylen-N$R^i$N$R^e R^f$, $C_3$-$C_{10}$-cycloalkyl, $C_5$-$C_{10}$-cycloalkenyl, heterocyclyl, phenyl, $C_3$-$C_{10}$-cycloalkyl-$C_1$-$C_5$-alkyl, $C_5$-$C_{10}$-cycloalkenyl-$C_1$-$C_5$-alkyl, heterocyclyl-$C_1$-$C_5$-alkyl, hetaryl-$C_1$-$C_5$-alkyl, phenyl-$C_1$-$C_5$-alkyl and phenoxy-$C_1$-$C_5$-alkyl wherein the cyclic moieties of the ten last mentioned radicals may be unsubstituted or may carry 1, 2, 3, 4 or 5 identical or different substituents $R^y$;

and where m is 0, 1 or 2

Y is O or S;

$X^1$ is S, O or N$R^{1a}$, where $R^{1a}$ is selected from hydrogen, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, O$R^a$, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$haloalkyl, $C_1$-$C_4$-alkoxy and $C_1$-$C_4$haloalkoxy;

$X^2$ is O$R^{2a}$, N$R^{2b}R^{2c}$, S(O)$_m R^{2d}$, where $R^{2a}$ is selected from $C_1$-$C_4$alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^{2b}$, $R^{2c}$ are independently of each other selected from hydrogen, $C_1$-$C_4$alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$alkylcarbonyl, $C_1$-$C_4$haloalkylcarbonyl, $C_1$-$C_4$alkylsulfonyl, $C_1$-$C_4$haloalkylsulfonyl, phenyl, phenylcarbonyl, phenylsulfonyl, hetaryl, hetarylcarbonyl, hetarylsulfonyl, phenyl-$C_1$-$C_4$alkyl and hetaryl-$C_1$-$C_4$alkyl, wherein the aromatic ring in the eight last mentioned radicals may be unsubstituted or may carry 1, 2, 3, 4 or 5 substituents which, independently of each other, are selected from the group consisting of halogen, cyano, nitro, $C_1$-$C_4$-haloalkyl, $C_1$-$C_4$-alkoxy and $C_1$-$C_4$-haloalkoxy; or $R^{2b}$ and $R^{2c}$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which, independently of each other, are selected from the group consisting of halogen, cyano, nitro, $C_1$-$C_4$alkyl, $C_1$-$C_4$haloalkyl, $C_1$-$C_4$-alkoxy and $C_1$-$C_4$haloalkoxy;

$R^{2d}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$X^3$ is a lone pair or oxygen;

$R^1$ is hydrogen, CN, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, O$R^a$, C(Y)$R^b$, C(Y)O$R^c$, S(O)$_2 R^d$, N$R^e R^f$, C(Y)N$R^g R^h$, S(O)$_m$N$R^e R^f$, C(Y)N$R^i$N$R^e R^f$, $C_1$-$C_5$-alkylen-O$R^a$, $C_1$-$C_5$-alkylen-CN, $C_1$-$C_5$-alkylen-C(Y)$R^b$, $C_1$-$C_5$-alkylen-C(Y)O$R^c$, $C_1$-$C_5$-alkylen-N$R^e R^f$, $C_1$-$C_5$-alkylen-C(Y)N$R^g R^h$, $C_1$-$C_5$-alkylen-S(O)$_2 R^d$, $C_1$-$C_5$-alkylen-S(O)$_m$N$R^e R^f$, $C_1$-$C_5$-alkylen-C(Y)N$R^i$N$R^e R^f$, phenyl, hetaryl, $C_3$-$C_{10}$-cycloalkyl, heterocyclyl, phenyl-$C_1$-$C_5$-alkyl, hetaryl-$C_1$-$C_5$-alkyl, heterocyclyl-$C_1$-$C_5$-alkyl, $C_3$-$C_{10}$-cycloalkyl-$C_1$-$C_5$-alkyl and phenoxy-$C_1$-$C_5$-alkyl, wherein the rings of the nine last mentioned radicals may be unsubstituted or may carry 1, 2, 3, 4 or 5 identical or different substituents selected from the radicals $R^y$;

$R^2$ is hydrogen, halogen, methyl, $C_1$-haloalkyl, methoxy, $C_1$-haloalkoxy, methylthio, $C_1$-haloalkylthio, methylsulfinyl, $C_1$-haloalkylsulfinyl, methylsulfonyl or $C_1$-haloalkylsulfonyl;

$R^3$ is hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl or $C_1$-$C_4$-alkoxy-$C_1$-$C_4$-alkyl;

$R^a$, $R^b$, $R^c$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy; $R^g$, $R^h$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^i$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from halogen, cyano, nitro, $C_1$-$C_4$-alkoxy and $C_1$-$C_4$-haloalkoxy;

$R^x$ are independently of each other selected from cyano, nitro, $C_1$-$C_4$-alkoxy, haloalkoxy, $C_1$-$C_4$-haloalkylthio, $C_1$-$C_4$-alkylsulfonyl, $C_1$-$C_4$-haloalkylsulfonyl, $C_1$-$C_{10}$-alkylcarbonyl, $C_3$-$C_{10}$-cycloalkyl, 5- to 7-membered heterocyclyl, phenyl, $C_3$-$C_6$-cycloalkoxy, 3- to 6-membered heterocyclyloxy and phenoxy, wherein the last 6 mentioned radicals may be unsubstituted or may carry 1, 2, 3, 4 or 5 radicals selected from the group consisting of halogen, cyano, nitro, $C_1$-$C_4$-alkyl, $C_1$-$C_4$-alkoxy and $C_1$-$C_4$-haloalkoxy;

$R^y$ is selected from halogen, cyano, nitro, $C_1$-$C_4$-alkyl, $C_1$-$C_4$-haloalkyl, $C_1$-$C_4$-alkoxy, $C_1$-$C_4$-haloalkoxy, $S(O)_m R^d$, $S(O)_m NR^e R^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_3$-$C_6$-cycloalkyl, 5- to 7-membered heterocyclyl, hetaryl, phenyl, $C_3$-$C_6$-cycloalkoxy, 3- to 6-membered heterocyclyloxy, hetaryloxy and phenoxy, wherein the last 8 mentioned radicals may be unsubstituted or may carry 1, 2, 3, 4 or 5 radicals selected from halogen, cyano, nitro, $C_1$-$C_4$-alkyl, $C_1$-$C_4$-alkoxy and $C_1$-$C_4$-haloalkoxy;

and the salts thereof, the N-oxides thereof, the tautomers thereof and the salts of said N-oxides or tautomers, except for 5-trifluoromethylthiophene-2-carboxylic acid pyridin-3-ylamide and the salts thereof.

The compounds of the present invention are particularly useful for controlling invertebrate pests, in particular for controlling arthropods and nematodes, especially for controlling insects, in particular for controlling insects of the order Homoptera. Therefore, the invention also relates to the use of a pyridine compound of the formulae I or II, a tautomer or an N-oxide thereof or a salt thereof, in particular an agriculturally or veterinarily acceptable salt thereof, for controlling invertebrate pests, in particular for controlling arthropods and nematodes, especially for controlling insects, in particular for controlling insects of the order Homoptera.

A further aspect of the present invention relates to a method for controlling invertebrate pests which method comprises treating the pests, their food supply, their habitat or their breeding ground or a cultivated plant, plant propagation materials such as seed, soil, area, material or environment in which the pests are growing or may grow, or the materials, plants, seeds, soils, surfaces or spaces to be protected from pest attack or infestation with a pesticidally effective amount of a pyridine compound of formulae I or II according to the present invention or a salt thereof or an N-oxide thereof or a salt of said N-oxide.

A further aspect of the present invention relates to a method for protecting plant propagation material, in particular seed and/or the plants which grow therefrom, which method comprises treating the plant propagation material with a pesticidally effective amount of a pyridine compound of the formulae I or II according to the present invention or an agriculturally acceptable salt, a tautomer or an N-oxide thereof or an agriculturally acceptable salt of said N-oxide or of said tautomer.

A further aspect of the present invention relates to plant propagation material, such as seed, comprising at least one compound of formulae I or II according to the present invention and/or an agriculturally acceptable salt, a tautomer or an N-oxide thereof or an agriculturally acceptable salt of said N-oxide or of said tautomer.

The present invention further relates to the use of compounds of formulae I or II as defined herein for controlling invertebrate pests.

A further aspect of the present invention relates to an agricultural composition containing at least one compound of formulae I or II according to the present invention and/or an agriculturally acceptable salt thereof or an N-oxide or tautomer thereof and/or an agriculturally acceptable salt of said N-oxide or said tautomer and at least one liquid or solid carrier.

A further aspect of the present invention relates to a compound of formulae I or II according to the present invention or a veterinarily acceptable salt thereof or a tautomer or an N-oxide thereof or a salt of said N-oxide or tautomer for the use in a method for treating or protecting a human or in particular a non-human animal from infestation or infection by parasites especially ectoparasites.

A further aspect of the present invention relates to a compound of formulae I or II according to the present invention or a veterinarily acceptable salt thereof or a tautomer or an N-oxide thereof or a salt of said N-oxide or tautomer for the use in a method for treating or protecting a human or in particular a non-human animal from infestation or infection by parasites especially ectoparasites.

A further aspect of the present invention relates to a method for treating or protecting an animal, in particular a non-human animal, from infestation or infection by parasites especially ectoparasites which comprises bringing the animal in contact with a parasiticidally effective amount of a compound of the formulae I or II or a veterinarily acceptable salt thereof or an N-oxide or tautomer thereof or with a veterinarily acceptable salt of said tautomer or N-oxide. Bringing the animal in contact with a compound of formulae I or II, a tautomer, an N-oxide or salt thereof or with a veterinary composition containing a compound of the invention, means applying or administering it to the animal.

Another object of the present invention is a veterinary composition containing at least one novel pyrazole compound of the formulae I or II as defined above and/or a veterinarily acceptable salt or an N-oxide thereof and at least one veterinarily acceptable liquid or solid carrier.

In the compounds of formulae I or II the substituents on A or the pyridyl ring may contain one or more centers of chirality. In this case the compounds of the formulae I or II can be present in the form of different enantiomers or diastereomers, depending on the substituents. In case of the formula II, the compound II may also exist as a cis- or trans-isomer with respect to the N=C axis. The present invention relates to every possible stereoisomer of the compounds of general formulae I or II, i.e. to single enantiomers or diastereomers, as well as to mixtures thereof.

The compounds of formulae I or II may be amorphous or may exist in one ore more different crystalline states (polymorphs) which may have a different macroscopic properties such as stability or show different biological properties such as activities.

The present invention includes both amorphous and crystalline compounds of formulae I or II, mixtures of different crystalline states of the respective compound I or II, as well as amorphous or crystalline salts thereof.

Salts of the compounds of the formulae I or II are preferably agriculturally and veterinarily acceptable salts. They can be formed in a customary method, e.g. by reacting the compound with an acid of the anion in question if the compound of formulae I or II has a basic functionality or by reacting an acidic compound of formulae I or II with a suitable base.

Agriculturally useful salts of the compounds of formulae I and II encompass especially the salts of those cations or the acid addition salts of those acids whose cations and anions, respectively, have no adverse effect on the pesticidal action of the compounds of formulae I or II. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formulae I and II with an acid of the corresponding anion, preferably of hydrochloric acid, hydrobromic acid, sulfuric acid, phosphoric acid or nitric acid.

Veterinarily acceptable salts of the compounds of formulae I or II encompass especially the salts of those cations or the acid addition salts which are known and accepted in the art for the formation of salts for veterinary use. Suitable acid addition salts, e.g. formed by compounds of formulae I or II containing a basic nitrogen atom, e.g. an amino group, include salts with inorganic acids, for example hydrochlorids, sulphates, phosphates, and nitrates and salts of organic acids for example acetic acid, maleic acid, e.g. the monoacid salts or diacid salts of maleic acid, dimaleic acid, fumaric acid, e.g. the monoacid salts or diacid salts of fumaric acid, difumaric acid, methane sulfenic acid, methane sulfonic acid, and succinic acid.

The term "N-oxide" includes any compound of the formulae I or II which, apart from the pyridine nitrogen that carries the moiety $X^3$, has at least one tertiary nitrogen atom that is oxidized to an N-oxide moiety.

The term "invertebrate pest" as used herein encompasses animal populations, such as arthropode pests, including insects and arachnids, as well as nematodes, which may attack plants thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat. Protoc. 2007; 2(5):1225-35, Curr. Opin. Chem. Biol. 2006 October; 10(5): 487-91. Epub 2006 August 28, Biomaterials. 2001 March; 22(5):405-17, Bioconjug. Chem. 2005 January-February; 16(1):113-21).

The term "cultivated plants" as used herein further includes plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20659, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20659, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" as used herein further includes plants that are by the use of recombinant DNA techniques capable to synthesize one or more insecticidal proteins, especially those known from the bacterial genus *bacillus*, particularly from *bacillus thuringiensis*, such as delta-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such as *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073.

The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods insects, particularly to beetles (Coleoptera), flies (Diptera), and butterflies and moths (Lepidoptera) and to plant parasitic nematodes (Nematoda).

The term "cultivated plants" as used herein further includes plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*).

The term "cultivated plants" as used herein further includes plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" as used herein further includes plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" as used herein further includes plants that contain by the use of recombinant DNA techniques a modified amount of substances of content or new substances of content, specifically to improve raw material production, for example potatoes that produce increased amounts of amylopectin (e.g. Amflora® potato).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms and in particular from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylpentyl, n-octyl, 1-methyloctyl, 2-methylheptyl, 1-ethylhexyl, 2-ethylhexyl, 1,2-dimethylhexyl, 1-propylpentyl and 2-propylpentyl.

The term "alkylene" (or alkanediyl) as used herein in each case denotes an alkyl radical as defined above, wherein one hydrogen atom at any position of the carbon backbone is replaced by one further binding site, thus forming a bivalent moiety. Accordingly, $C_1$-$C_5$-alkylene is a divalent branched or unbranched saturated aliphatic chain having 1 to 5 carbon atoms, for example —$CH_2$—, —$CH_2CH_2$—, —$CH(CH_3)$—, —$CH_2CH_2CH_2$—, —$CH(CH_3)CH_2$—, —$CH_2CH_2CH_2CH_2$—, —$CH_2CH(CH_3)CH_2$—, —$CH(CH_3)CH(CH_3)$—, —$CH_2CH_2CH_2CH_2CH_2$—, —$CH_2(CH_2)_2CH(CH_3)$—, —$CH_2C(CH_3)_2CH_2$—, and the like.

The term "haloalkyl" as used herein and in the haloalkyl moieties of haloalkoxy, haloalkylthio, haloalkylcarbonyl, haloalkylsulfonyl and haloalkylsulfinyl, denotes in each case a straight-chain or branched alkyl group having usually from 1 to 10 carbon atoms, frequently from 1 to 6 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group usually having from 1 to 10 carbon atoms, frequently from 1 to 6 carbon atoms, preferably 1 to 4 carbon atoms, which is bound to the remainder of the molecule via an oxygen atom. Examples of an alkoxy group are methoxy, ethoxy, n-propoxy, iso-propoxy, n-butyloxy, 2-butyloxy, iso-butyloxy, tert.-butyloxy, and the like.

The term "haloalkoxy" as used herein denotes in each case a straight-chain or branched alkoxy group, as defined above, having from 1 to 10 carbon atoms, frequently from 1 to 4 carbon atoms, preferably 1 to 3 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluorethoxy, 2,2,2-trichloroethoxy, pentafluoroethoxy and the like.

The term "cycloalkyl" as used herein denotes in each case a mono- or bicyclic cycloaliphatic radical having usually from 3 to 10 carbon atoms or 3 to 6 carbon atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1]heptyl, and bicyclo[2.2.2]octyl.

The term "$C_n$-$C_m$-cycloalkyl-$C_o$-$C_p$-alkyl" as used herein refers to a cycloalkyl group, as defined above, having n to m carbon atoms, which is bound to the remainder of the molecule via an alkylene group, as defined above, having o to p carbon atoms. Examples are cyclopropylmethyl, cyclopropylethyl, cyclopropylpropyl, cyclobutylmethyl, cyclobutylethyl, cyclobutylpropyl, cyclopentylmethyl, cycloppentylethyl, cyclopentylpropyl, cyclohexylmethyl, cyclohexylethyl, cyclohexylpropyl, and the like.

The term "$C_3$-$C_6$-cycloalkoxy" as used herein refers to a cycloalkyl group, as defined above, having 3 to 6 carbon atoms, which is bound to the remainder of the molecule via an oxygen atom. Examples of $C_3$-$C_6$-cycloalkoxy groups include cycloproppyloxy, cyclopentyloxy, cyclohexyloxy and the like.

The term "halocycloalkyl" as used herein denotes in each case a mono- or bicyclic cycloaliphatic radical having usually from 3 to 10 carbon atoms or 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "$C_5$-$C_{10}$-cycloalkenyl" as used herein denotes in each case an aliphatic ring system radical having 5 to 10 carbon atoms that comprises at least one carbon-carbon double bond in the ring. Examples of cycloalkenyl groups include, but are not limited to, cyclopropenyl, cyclopentenyl, cyclohexenyl, cycloheptenyl, and the like.

The term "$C_5$-$C_{10}$-cycloalkenyl-$C_1$-$C_5$-alkyl" refers to cycloalkenyl as defined above which is bound via an alkylene group, as defined above, having 1 to 5 carbon atoms to the remainder of the molecule. Examples include but are not limited to cyclopentenylmethyl, cyclopentenylethyl, cyclohexenylpropyl, cyclohexenylpentyl, cycloheptenylmethyl, and the like.

The term "alkenyl" as used herein denotes in each case a singly unsaturated hydrocarbon radical having usually 2 to 10, preferably 2 to 4 carbon atoms, e.g. vinyl, allyl (2-propen-1-yl), 1-propen-1-yl, 2-propen-2-yl, methallyl (2-methyl-prop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "haloalkenyl" as used herein, which may also expressed as "alkenyl which may be substituted by halogen", and the haloalkenyl moieties in haloalkenyloxy, haloalkenylcarbonyl and the like refers to unsaturated straight-chain or branched hydrocarbon radicals having 2 to 10 ("$C_2$-$C_{10}$-haloalkenyl") or 2 to 4 ("$C_2$-$C_4$-haloalkenyl") carbon atoms and a double bond in any position, where some or all of the hydrogen atoms in these groups are replaced by halogen atoms as mentioned above, in particular fluorine, chlorine and bromine, for example chlorovinyl, chloroallyl and the like.

The term "alkynyl" as used herein refers to unsaturated straight-chain or branched hydrocarbon radicals having usually 2 to 10, preferably 2 to 4 carbon atoms and one or two triple bonds in any position, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "$C_3$-$C_{10}$-haloalkynyl" as used herein, which is also expressed as "$C_3$-$C_{10}$-alkynyl which may be substituted by halogen", refers to unsaturated straight-chain or branched hydrocarbon radicals having 3 to 10 carbon atoms and one or two triple bonds in any position (as mentioned above), where some or all of the hydrogen atoms in these groups are replaced by halogen atoms as mentioned above, in particular fluorine, chlorine and bromine;

The term "alkoxyalkyl" as used herein refers to alkyl usually comprising 1 to 4 carbon atoms, wherein 1 carbon atom carries an alkoxy radical usually comprising 1 to 10, in particular 1 to 4, carbon atoms as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methylpropoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "alkylcarbonyl" (alkyl-C(=O)—), as used herein refers to a straight-chain or branched saturated alkyl group as define above comprising 1 to 10 carbon atoms (=$C_1$-$C_{10}$-alkylcarbonyl), preferably 1 to 4 carbon atoms (=$C_1$-$C_4$-alkylcarbonyl) attached through the carbon atom of the carbonyl group at any position in the alkyl group.

The term "haloalkylcarbonyl" as used herein refers to an alkylcarbonyl group as defined above wherein the hydrogen atoms are partially or fully substituted by fluorine, chlorine, bromine and/or iodine.

The term "alkylthio "(also alkylsulfanyl or alkyl-S—)" as used herein refers to a straight-chain or branched saturated alkyl group comprising 1 to 10 carbon atoms (=$C_1$-$C_{10}$-alkylthio), preferably 1 to 4 carbon atoms (=$C_1$-$C_4$-alkylthio) as defined above, which is attached via a sulfur atom at any position in the alkyl group.

The term "haloalkylthio" as used herein refers to an alkylthio group as defined above wherein the hydrogen atoms are partially or fully substituted by fluorine, chlorine, bromine and/or iodine. The term "$C_1$-$C_4$-haloalkylthio" is a $C_1$-$C_4$-haloalkyl group, as defined above, attached via a sulfur atom. The term "$C_1$-haloalkylthio" is a $C_1$-haloalkyl group, as defined above, attached via a sulfur atom. $C_1$-haloalkylthio is e.g. $SCH_2F$, $SCHF_2$, $SCF_3$, $SCH_2Cl$, $SCHCl_2$, $SCCl_3$, chlorofluoromethylthio, dichlorofluoromethylthio or chlorodifluoromethylthio. $C_1$-$C_4$-Haloalkylthio is additionally, for example, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio.

The term "alkylsulfinyl" (also alkylsulfoxyl or alkyl-S(=O)—), as used herein refers to a straight-chain or branched saturated alkyl group as define above comprising 1 to 10 carbon atoms (=$C_1$-$C_{10}$-alkylsulfinyl), preferably 1 to 4 carbon atoms (=$C_1$-$C_4$-alkylsulfinyl) attached through the sulfur atom of the sulfinyl group at any position in the alkyl group.

The term "haloalkylsulfinyl" as used herein refers to an alkylsulfinyl group as defined above wherein the hydrogen atoms are partially or fully substituted by fluorine, chlorine, bromine and/or iodine.

The term "alkylsulfonyl" (also alkyl-S(=O)$_2$—) as used herein refers to a straight-chain or branched saturated alkyl group comprising 1 to 10 carbon atoms (=$C_1$-$C_{10}$-alkylsulfonyl), preferably 1 to 4 carbon atoms (=$C_1$-$C_4$-alkylsulfonyl), as defined above, which is attached via the sulfur atom of the sulfonyl group at any position in the alkyl group.

The term "haloalkylsulfonyl" as used herein refers to an alkylsulfonyl group as defined above wherein the hydrogen atoms are partially or fully substituted by fluorine, chlorine, bromine and/or iodine.

The term "heterocyclyl" includes in general 3-, 4-, 5-, 6-, 7- or 8-membered, in particular 5-, 6-, 7- or 8-membered monocyclic heterocyclic non-aromatic radicals and 8 to 10 membered bicyclic heterocyclic non-aromatic radicals, the mono- and bicyclic non-aromatic radicals may be saturated or unsaturated. The mono- and bicyclic heterocyclic non-aromatic radicals usually comprise 1, 2, 3 or 4 heteroatoms, in particular 1 or 2 heteroatoms selected from N, O and S as ring members, where S-atoms as ring members may be present as S, SO or $SO_2$. Examples of saturated or unsaturated 3-, 4-, 5-, 6-, 7- or 8-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, S-oxothiolanyl, S-dioxothiolanyl, dihydrothienyl, S-oxodihydrothienyl, S-dioxodihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, 1,3- and 1,4-dioxanyl, thiopyranyl, S-oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

Examples of 3-, 4-, 5-, 6- or 7-membered saturated heterocyclyl include: Oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro-[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

The term "heterocyclyloxy" as used herein refers to heterocyclyl groups, as defined above, in particular those that are 3-, 4-5- or 6-membered, which are bound to the remainder of the molecule via an oxygen atom. Examples of $C_3$-$C_6$-heterocycloalkoxy groups include oxiranyloxy, tetrahydropyranyloxy, pyrrolinyloxy and the like.

The term "heterocyclyl-$C_1$-$C_5$-alkyl" as used herein refers to heterocyclyl groups, as defined above, in particular those that are 3-, 4-, 5- or 6-membered, which are bound via an alkylene group, as defined above, having 1 to 5 carbon atoms to the remainder of the molecule.

The term "hetaryl" (also referred to as "heteroaryl") includes in general 5- or 6-membered unsaturated monocyclic heterocyclic radicals and 8 to 10 membered unsaturated bicyclic heterocyclic radicals which are aromatic, i.e. they comply with Mickel's rule (4n+2 rule). Hetaryl usually comprise besides carbon atom(s) as ring member(s) 1, 2, 3 or 4 heteroatoms selected from N, O and S as ring members. Examples of 5- or 6-membered heteroaromatic radicals include: 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl or 5-isoxazolyl, 3-isothiazolyl, 4-isothiazolyl or 5-isothiazolyl, 1-imidazolyl, 2-imidazolyl, 4-imidazolyl, 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, 2- or 5-(1,3,4-thiadiazol)yl, 4- or 5-(1,2,3-thiadiazol)yl, 3- or 5-(1,2,4-thiadiazol)yl, 1H-, 2H- or 3H-1,2,3-triazol-4-yl, 1,3,4-triazol-2-yl, 2H-triazol-3-yl, 1H-, 2H-, or 4H-1,2,4-triazolyl, 1H- or 2H-tetrazolyl 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "hetaryl" also includes bicyclic 8- to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "phenylalkyl" and "phenoxyalkyl" refers to phenyl or phenoxy, respectively, which are bound via an alkyl group having usually 1 to 4 carbon atoms, in particular a methyl group (=phenylmethyl), to the remainder of the molecule, examples including benzyl, 1-phenylethyl, 2-phenylethyl, 2-phenoxyethyl and the like.

The terms "heterocyclylalkyl" and "hetarylalkyl" refer to heterocyclyl or hetaryl, respectively, as defined above, which are bound via an alkylene group, as defined above, in particular a methylene group (=heterocyclylmethyl or hetarylmethyl, respectively) or an 1,1-ethandiyl or 1,2-ethandiyl group (=1-heterocyclylethyl, 2-heterocyclylethyl, 1-hetarylethyl or 2-hetarylethyl, respectively), to the remainder of the molecule.

The term "phenylcarbonyl" (phenyl-C(=O)—), as used herein refers to a phenyl group that is bound to the remainder of the molecule via the carbon atom of the carbonyl group.

The term "hetarylcarbonyl" (hetaryl-C(=O)—) and "heterocyclylcarbonyl" (heterocyclyl-C(=O)—) refer to a hetaryl or heterocyclyl, respectively, as defined above, which are bound via the carbon atom of the carbonyl group to the remainder of the molecule, wherein the carbon atom of the carbonyl group is attached through any one of the carbon atoms of the hetaryl or heterocyclyl, respectively.

The term "phenylsulfonyl" (also phenyl-S(=O)$_2$—) as used herein refers to phenyl group that is bound to the remainder of the molecule via the sulfur atom of the sulfonyl group.

The term "hetarylsulfonyl" (hetaryl-S(=O)$_2$—) and "heterocyclylsulfonyl" (heterocyclyl-S(=O)$_2$—) refer to a hetaryl or heterocyclyl, respectively, as defined above, which are bound via the sulfur atom of the sulfonyl group to the remainder of the molecule, wherein the sulfur atom of the sulfonyl group is attached through any one of the carbon atoms of the hetaryl or heterocyclyl, respectively.

The remarks made below as to preferred embodiments of the variables (substituents) of the compounds of formulae I or II are valid on their own as well as preferably in combination with each other.

The remarks made below concerning preferred embodiments of the variables further are valid concerning the compounds of formulae I or II as well as concerning the uses and methods according to the invention and the composition according to the present invention.

A preferred embodiment of the invention relates to compounds of the formula I, to their salts, to their N-oxides and to the methods and uses of such compounds. Amongst the compounds of the formula I, preference is given to those compounds, wherein $X^1$ in formula I is oxygen, sulphur or a moiety N—$R^{1a}$, wherein $R^{1a}$ is as defined above. Particular preference is given to those compounds of the formula I wherein $X^1$ is oxygen.

In the compounds of the formula I, wherein X is $NR^{1a}$, a particular embodiment relates to those compounds, wherein $R^{1a}$ is $C_1$-$C_6$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_6$-alkenyl, $C_2$-$C_6$-haloalkenyl, $C_2$-$C_6$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, or a moiety $OR^a$. In particular, $R^{1a}$ is $C_1$-$C_6$-alkyl, $C_3$-$C_6$-cycloalkylmethyl, $C_3$-$C_6$-alkenyl, $C_3$-$C_6$-alkynyl, $C_1$-$C_4$-alkoxy-$C_1$-$C_4$-alkyl or a moiety $OR^a$, wherein $R^a$ is as defined above and in particular selected from $C_1$-$C_4$-alkyl, $C_3$-$C_6$-cycloalkylmethyl, $C_2$-$C_4$-alkenyl, especially $C_3$-$C_4$-alkenyl, $C_2$-$C_4$-alkynyl, especially $C_3$-$C_4$-alkynyl, and $C_1$-$C_4$-alkoxy-$C_1$-$C_4$-alkyl.

Amongst the compounds of the formula I, preference is given to those compounds, wherein $R^1$ is hydrogen, CN, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_1$-$C_5$-alkylene-CN, $OR^a$, $C_1$-$C_5$- alkylene-OR$^a$, C(Y)R$^b$, C(Y)OR$^c$, S(O)$_2$R$^d$, heterocyclyl-C$_1$-C$_5$-alkyl, hetaryl-C$_1$-C$_5$-alkyl, or C$_3$-C$_{10}$-cycloalkyl-C$_1$-C$_5$-alkyl, wherein the cyclic moiety of the three last-mentioned radicals may be unsubstituted or may carry 1, 2, 3, 4, or 5 identical or different substituents selected from the radicals R$^y$. In these compounds, the radicals R$^a$, R$^b$, R$^c$, R$^d$ and R$^y$ are as defined above. R$^a$ is in particular C$_1$-C$_4$-alkyl, C$_3$-C$_6$-cycloalkylmethyl, C$_2$-C$_4$-alkenyl, especially C$_3$-C$_4$-alkenyl, C$_2$-C$_4$-alkynyl, especially C$_3$-C$_4$-alkynyl, and C$_1$-C$_4$-alkoxy-C$_1$-C$_4$-alkyl. R$^b$ in particular C$_1$-C$_4$-alkyl, C$_3$-C$_6$-cycloalkylmethyl, C$_2$-C$_4$-alkenyl, especially C$_3$-C$_4$-alkenyl, C$_2$-C$_4$-alkynyl, especially C$_3$-C$_4$-alkynyl, and C$_1$-C$_4$-alkoxy-C$_1$-C$_4$-alkyl. In particular, R$^y$ is halogen, cyano, nitro, C$_1$-C$_4$-alkyl, C$_1$-C$_4$-haloalkyl, C$_1$-C$_4$-alkoxy or C$_1$-C$_4$-haloalkoxy. More preference is given to compounds of formula I, wherein R$^1$ is hydrogen, C$_1$-C$_{10}$-alkyl, C$_1$-C$_{10}$-haloalkyl, C$_1$-C$_4$-alkylene-CN, heterocyclyl-C$_1$-C$_5$-alkyl, in particular heterocyclylmethyl, 1-heterocyclylethyl or 2-heterocyclylethyl, wherein the heterocyclyl radicals may be unsubstituted or may carry 1, 2 or 3 radicals R$^y$ as defined above, hetaryl-C$_1$-C$_5$-alkyl, in particular hetarylmethyl, 1-hetarylethyl or 2-hetarylethyl, wherein the hetaryll radicals may be unsubstituted or may carry 1, 2 or 3 radicals R$^y$ as defined above, C$_1$-C$_5$-alkylen-OR$^a$ or C$_3$-C$_{10}$-cycloalkyl-C$_1$-C$_5$-alkyl. In particular, R$^1$ is hydrogen, C$_1$-C$_4$-alkyl, C$_1$-C$_4$-haloalkyl, C$_1$-C$_3$-alkylene-O—C$_1$-C$_3$-alkyl or C$_1$-C$_4$-alkylene-CN, in particular hydrogen, methyl, ethyl, methoxymethyl or ethoxymethyl.

Another embodiment of the invention relates to pyridine compounds of the formula II, to their salts, to their N-oxides and to the methods and uses of such compounds. In the compounds of the formula II, preference is given to those compounds, wherein X$^2$ in formula II is OR$^{2a}$, wherein R$^{2a}$ is as defined above, preferably C$_1$-C$_4$-alkyl, C$_2$-C$_4$-alkenyl, C$_3$-C$_4$-alkynyl, phenyl, benzyl(phenylmethyl) or C$_1$-C$_4$-alkoxy-C$_1$-C$_4$-alkyl.

Another embodiment relates to compounds of the formula I, wherein X$^2$ is formula II is S(O)$_m$R$^{2d}$, wherein Red is as defined above, preferably, C$_1$-C$_4$-alkyl, C$_2$-C$_4$-alkenyl, C$_3$-C$_4$-alkynyl, phenylmethyl or C$_1$-C$_4$-alkoxy-C$_1$-C$_4$-alkyl. In these compounds m is preferably 0.

Another embodiment relates to compounds of the formula II, wherein X$^2$ is NR$^{2b}$R$^{2c}$. In these compounds R$^{2b}$ and R$^{2c}$ are preferably selected, independently of each other, from hydrogen, C$_1$-C$_4$-alkyl, C$_1$-C$_4$-alkoxy-C$_1$-C$_4$-alkyl, phenyl or benzyl or R$^{2b}$ and R$^{2c}$, together with the nitrogen atom to which they are attached, form a saturated, nitrogen-bound 5- or 6-membered heterocycle which may comprise a further heteroatom selected from O, S and N, e.g. NR$^{2b}$R$^{2c}$ being 1-pyrrolidinyl, 1-piperidinyl, 1-piperazinyl, 4-morpholinyl or 4-thiomorpholinyl.

Among the compounds of formulae I and II, preference is given to those compounds, wherein R$^2$ is hydrogen, halogen, methyl, C$_1$-fluoroalkyl, methoxy or C$_1$-fluoroalkoxy, in particular hydrogen, fluorine, chlorine, bromine, methyl, difluoromethyl, trifluoromethyl, methoxy, difluoromethoxy or trifluoromethoxy.

Among the compounds of formulae I and II, preference is given to those compounds, wherein, R$^3$ is hydrogen, halogen, C$_1$-C$_4$-alkyl, C$_1$-C$_3$-haloalkyl, C$_2$-C$_4$-alkenyl, C$_2$-C$_4$-haloalkenyl, C$_2$-C$_4$-alkynyl or C$_1$-C$_4$-alkoxy-C$_1$-C$_4$-alkyl. In these compounds, R$^3$ is in particular hydrogen, fluorine, chlorine, bromine, methyl, difluoromethyl, trifluoromethyl, methoxy, difluoromethoxy or trifluoromethoxy.

In particular, at least one of the radicals R$^2$ or R$^3$ in formulae I and II is hydrogen. Another preferred embodiment relates to compounds of formulae I or II, wherein R$^2$ is hydrogen and R$^3$ is hydrogen, fluorine, chlorine, bromine, methyl, difluoromethyl, trifluoromethyl, methoxy, difluoromethoxy or trifluoromethoxy. Likewise, preference is given to compounds of formulae I and II, wherein R$^2$ is hydrogen, fluorine, chlorine, bromine, methyl, difluoromethyl, trifluoromethyl, methoxy, difluoromethoxy or trifluoromethoxy and R$^3$ is hydrogen. A very preferred embodiment of the invention relates to compounds of the formulae I and II and to their salts, wherein both R$^2$ and R$^3$ are hydrogen.

Among the compounds of formulae I and II, preference is given to those compounds, wherein X$^3$ in formulae I or II is a lone pair.

Another preferred embodiment of the invention relates to pyridine compounds of formulae I and II, to the salts and N-oxides thereof and to the methods and uses of such compounds, wherein A is a radical A1. Among the compounds, wherein A is a radical A1, preference is given to compounds of the formula I, wherein X$^1$, R$^1$, R$^2$, R$^3$ and X$^3$ are as defined above and in particular have one of the preferred meanings and n is 0. Likewise, preference is given to compounds of formula I, wherein A is a radical A1 and X$^1$, R$^1$, R$^2$, R$^3$ and X$^3$ are as defined above and in particular have one of the preferred meanings and n is 1. Likewise, preference is given to compounds of formula I, wherein A is a radical A1 and X$^1$, R$^1$, R$^2$, R$^3$ and X$^3$ are as defined above and in particular have one of the preferred meanings and n is 2. Likewise, preference is given to compounds of formula I, wherein A is a radical A1 and X$^1$, X$^2$, R$^1$, R$^2$, R$^3$ and X$^3$ are as defined above and in particular have one of the preferred meanings and n is 3.

Among the compounds of formulae I and II, wherein A is a radical A1, preference is given to those compounds, wherein Z is O.

Among the compounds of formulae I and II, wherein A is a radical A1, preference is further given to those compounds, wherein Z is S.

Among the compounds of formulae I and II, wherein A is a radical A1, preference is further given to those compounds, wherein Z is N—R$^N$.

In the compounds of the formulae I and II, wherein A is a radical A1, the radical R$^A$, if present, is preferably selected from
halogen, such as bromine or chlorine,
CN,
NO$_2$,
C$_1$-C$_{10}$-alkyl, in particular C$_1$-C$_4$-alkyl, such as methyl, ethyl, n-propyl, isopropyl, n-butyl, tert.-butyl or 2-methylpropyl,
C$_1$-C$_{10}$-alkyl, in particular C$_1$-C$_4$-alkyl, which is partially or fully halogenated or carries 1, 2 or 3 identical or different substituents R$^x$ selected from C$_1$-C$_4$-alkoxy, C$_1$-C$_4$-haloalkoxy, C$_3$-C$_6$-cycloalkyl, 5- to 7-membered heterocyclyl, phenyl and phenoxy, wherein the last four mentioned radicals may be unsubstituted or may carry 1, 2, 3, 4 or 5 radicals selected from halogen, nitro, C$_1$-C$_4$-alkyl, C$_1$-C$_4$-alkoxy and C$_1$-C$_4$-haloalkoxy,
C$_2$-C$_{10}$-alkenyl, in particular C$_2$-C$_4$-alkenyl, such as 2-propenyl, cis or trans 2-buten-1-yl, which may be partially or fully halogenated or may carry 1, 2 or 3 identical or different substituents R$^x$ selected from C$_1$-C$_4$-alkoxy, C$_1$-C$_4$-haloalkoxy, C$_3$-C$_6$-cycloalkyl, 5- to 7-membered heterocyclyl, phenyl and phenoxy, wherein the last four mentioned radicals may be unsubstituted or may carry 1, 2, 3, 4 or 5 identical or different radicals selected from halogen, nitro, C$_1$-C$_4$-alkyl, C$_1$-C$_4$-alkoxy and C$_1$-C$_4$-haloalkoxy, $C_3$-$C_6$-cycloalkyl, such as cyclopropyl, cyclobutyl or cyclopentyl, $C_3$-$C_6$-halocycloalkyl, hetaryl-$C_1$-$C_5$-alkyl, in particular hetarylmethyl, 1-hetarylethyl or 2-hetarylethyl, wherein the hetararyl moiety may be unsubstituted or may carry 1, 2, 3, 4 or 5 identical or different substituents $R^y$, wherein $R^y$ is as defined above and preferably has one of the meanings being preferred, e.g. 2-furylmethyl, 3-furylmethyl, 5-methylfuran-2-ylmethyl, 2-thienylmethyl, 3-thienylmethyl, isothiazol-3-ylmethyl, isothiazol-4-ylmethyl, isothiazol-5-ylmethyl, isoxazol-3-ylmethyl, isoxazol-4-ylmethyl, isoxazol-5-ylmethyl, oxazol-2-ylmethyl, oxazol-4-ylmethyl, oxazol-5-ylmethyl, thiazol-2-ylmethyl, thiazol-4-ylmethyl, thiazol-5-ylmethyl, 1H-pyrazol-3-ylmethyl, 1H-pyrazol-4-ylmethyl, 2H-pyrazol-3-ylmethyl, 1-methyl-1H-pyrazol-3-ylmethyl, 1-methyl-1H-pyrazol-4-ylmethyl, 2-methyl-2H-pyrazol-3-ylmethyl, 3,5-dimethylpyrazol-1-ylmethyl, 1H-imidazol-2-ylmethyl, 1H-imidazol-4-ylmethyl, 1H-imidazol-5-ylmethyl, 1-methyl-1H-imidazol-2-ylmethyl, 1-methyl-1H-imidazol-4-ylmethyl, 1-methyl-1H-imidazol-5-ylmethyl, 2-pyridylmethyl or 3-pyridylmethyl, phenyl, which may be unsubstituted or may carry 1, 2, 3, 4 or 5 identical or different substituents $R^y$, wherein $R^y$ is as defined above and preferably has one of the meanings being preferred, phenyl-$C_1$-$C_5$-alkyl, which may be unsubstituted or wherein the phenyl moiety may carry 1, 2, 3, 4 or 5 identical or different substituents $R^y$, wherein $R^y$ is as defined above and preferably has one of the meanings being preferred, phenoxy-$C_1$-$C_5$-alkyl, which may be unsubstituted or wherein the aromatic moiety may carry 1, 2, 3, 4 or 5 identical or different substituents $R^y$, wherein $R^y$ is as defined above and preferably has one of the meanings being preferred, $OR^a$, wherein $R^a$ is as defined above and preferably has one of the preferred meanings, $C(O)R^b$, wherein $R^b$ is as defined above and preferably has one of the meanings being preferred.

More preferably, the radical $R^A$, if present, is selected from halogen, CN, $NO_2$, $C_1$-$C_4$-alkyl, $C_1$-$C_4$-haloalkyl, $C_3$-$C_6$-cycloalkyl, $C_3$-$C_6$-halocycloalkyl and $C_1$-$C_4$-alkyl which carries one substituent $R^x$, wherein $R^x$ is cyano, $C_1$-$C_4$-alkoxy, $C_1$-$C_4$-haloalkoxy, $C_3$-$C_6$-cycloalkyl, 5- to 7-membered heterocyclyl, phenyl or phenoxy, wherein the last four mentioned radicals may be unsubstituted or may carry 1 or 2, 3, 4 or 5 identical or different radicals selected from halogen, nitro, $C_1$-$C_4$-alkyl, $C_1$-$C_4$-haloalkyl, $C_1$-$C_4$-alkoxy and $C_1$-$C_4$-haloalkoxy, or wherein the radical $R^A$, if present, is further selected from $C_1$-$C_4$-alkoxy, $C_1$-$C_4$-haloalkoxy, $C(O)C_1$-$C_4$-alkyl, $C(O)$phenyl, wherein the phenyl moiety may be unsubstituted or carries one or two identical or different substituents selected from halogen, nitro, $C_1$-$C_4$-alkyl, $C_1$-$C_4$-haloalkyl, $C_1$-$C_4$-alkoxy and $C_1$-$C_4$-haloalkoxy, phenyl, phenoxy-$C_1$-$C_5$-alkyl and hetaryl-$C_1$-$C_5$-alkyl, wherein the cyclic moiety of the three last mentioned radicals may be unsubstituted or carries one or two identical or different substituents selected from halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkyl.

In particular, the radical $R^A$, if present, is selected from halogen, $NO_2$, $C_1$-$C_4$-alkyl, $C_1$-$C_4$-haloalkyl, $C_1$-$C_4$-alkoxy, $C_1$-$C_4$-haloalkoxy, $C(O)C_1$-$C_4$-alkyl, benzoyl, $C_3$-$C_6$-cycloalkyl, $C_3$-$C_6$-halocycloalkyl, phenyl, phenoxy-$C_1$-$C_4$-alkyl and hetaryl-$C_1$-$C_4$-alkyl, wherein the cyclic moiety of the three last mentioned radicals is unsubstituted or substituted by 1 or 2 identical or different radicals selected from halogen, nitro, $C_1$-$C_4$-alkyl, $C_1$-$C_4$-alkoxy, $C_1$-$C_4$-haloalkoxy, $C_1$-$C_4$-alkylsulfonyl and $C_1$-$C_4$-haloalkyl.

Even more preferably, the radical $R^A$, if present, is selected from halogen, CN, $NO_2$, $C_1$-$C_4$-alkyl, $C_3$-$C_6$-cycloalkyl and $C_3$-$C_6$-halocycloalkyl. More particularly, the radical $R^A$, if present, is halogen, $C_1$-$C_2$-alkyl or $C_1$-$C_2$-haloalkyl.

A further embodiment of the invention relates to compounds of formulae I and II, to their N-oxides and their salts, wherein A is a radical A1 and wherein $R^A$ is absent, i.e. n is 0. It is understood that if n is 0, the radical A1 in formulae I and II is unsubstituted.

A further embodiment of the invention relates to compounds of formulae I and II, to their N-oxides and their salts, wherein the above examples of substituents $R^A$ are not in combination with other $R^A$, i.e. n is 1.

In the formulae A1 and A2, where the variable n is 2 or 3, $R^A$ may be identical or different.

A further embodiment of the invention relates to compounds of formulae I and II, to their N-oxides and their salts, wherein A is a radical A1 and the above examples of radical $R^A$ are in combination with other radical $R^A$, i.e. n is 2 or 3. In the formula A1, where the variable n is 2 or 3, $R^A$ may be identical or different.

In the compounds of the formulae I and II, wherein A is a radical A1 with Z being a radical $R^N$, $R^N$ is preferably selected from hydrogen, $NO_2$, $C_1$-$C_{10}$-alkyl and $C_2$-$C_{10}$-alkenyl, wherein the last two mentioned radicals may be unsubstituted, may be partially or fully halogenated or may carry 1, 2 or 3 identical or different substituents $R^x$, which are as defined above and which are preferably selected from cyano, $C_1$-$C_4$-alkoxy, $C_1$-$C_4$-haloalkoxy, $C_3$-$C_6$-cycloalkyl, 5- to 6-membered heterocyclyl, phenyl and phenoxy, wherein the four last mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy, or wherein $R^N$ is further selected from $C_3$-$C_{10}$-cycloalkyl, $C_5$-$C_{10}$-cycloalkenyl, heterocyclyl, phenyl, $C_3$-$C_{10}$-cycloalkyl-$C_1$-$C_5$-alkyl, heterocyclyl-$C_1$-$C_5$-alkyl, hetaryl-$C_1$-$C_5$-alkyl, phenyl-$C_1$-$C_5$-alkyl and phenoxy-$C_1$-$C_5$-alkyl, wherein the cyclic moieties of the nine last mentioned radicals may be unsubstituted or may carry 1, 2, 3, 4 or 5 identical or different substituents $R^y$, which are as defined above and which are preferably selected from halogen, $C_1$-$C_4$-alkyl, $C_1$-$C_4$-alkoxy, $C_1$-$C_4$-haloalkoxy, $C_1$-$C_4$-alkylcarbonyl and $C_1$-$C_4$-haloalkylcarbonyl.

Examples of preferred radicals $R^N$ include:

hydrogen;

$C_1$-$C_{10}$-alkyl, in particular $C_1$-$C_6$-alkyl, such as methyl, ethyl, n-propyl, isopropyl, n-butyl, tert.-butyl or 2-methylpropyl;

$C_1$-$C_{10}$-haloalkyl, in particular $C_1$-$C_6$-haloalkyl, such as 2-fluoroethyl, 2-chloroethyl, 2-bromoethyl, 2,2-difluoroethyl, 2,2-dichloroethyl, 2,2-dibromoethyl or 2,2,2-trifluoroethyl;

$C_2$-$C_{10}$-alkenyl, in particular $C_2$-$C_4$-alkenyl, such as vinyl, 2-propenyl, cis or trans 2-buten-1-yl;

$C_2$-$C_{10}$-haloalkenyl, in particular $C_3$-$C_4$-haloalkenyl such as 3,3-dichloro-2-propenyl or 3,3-dibromo-2-propenyl;

$C_1$-$C_4$-alkylene-CN such as cyanomethyl, cyanoethyl, 2-cyano-1-methylethyl, or 2-cyano-2-methylethyl;

$C_1$-$C_4$-alkylen-$C_1$-$C_4$-alkoxy such as methoxymethyl, ethoxymethyl, 2-methoxyethyl or 2-ethoxyethyl;

$C_3$-$C_6$-cycloalkyl, such as cyclopropyl, cyclobutyl or cyclopentyl; $C_3$-$C_6$-cycloalkyl, which carries 1, 2, 3, 4 or 5, in particular 1, 2 or 3 radicals $R^y$ which are as defined above and which are preferably selected from halogen, $C_1$-$C_4$-alkyl and $C_1$-$C_4$-haloalkyl;

$C_3$-$C_6$-cycloalkyl-$C_1$-$C_5$-alkyl, in particular $C_3$-$C_6$-cycloalkylmethyl, 1-$C_3$-$C_6$-cycloalkylethyl or 2-$C_3$-$C_6$-cycloalkylethyl such as cyclopropylmethyl, cyclobutylmethyl or cyclopentylmethyl;

phenyl, which may be unsubstituted or may carry 1, 2, 3, 4 or 5, in particular 1, 2 or 3 radicals $R^y$ as defined herein;

phenyl-$C_1$-$C_5$-alkyl, in particular benzyl, 1-phenylethyl or 2-phenylethyl, wherein the phenyl radicals may be unsubstituted or may carry 1, 2, 3, 4 or 5, in particular 1, 2 or 3 radicals $R^y$ as defined herein, e.g. benzyl;

heterocyclyl-$C_1$-$C_5$-alkyl, in particular heterocyclylmethyl, 1-heterocyclylethyl or 2-heterocyclylethyl, wherein the heterocyclyl radicals may be unsubstituted or may carry 1, 2 or 3 radicals $R^y$ as defined above, e.g. oxetan-2-ylmethyl, oxetan-3-ylmethyl, thietan-3-ylmethyl, 3,3-dioxathietan-3-ylmethyl, oxolan-2-ylmethyl, oxolan-3-ylmethyl, oxazolin-2-ylmethyl, thiazolin-2-ylmethyl, 1H-imidazolin-2-ylmethyl, 1-methyl-1H-imidizolin-2-ylmethyl or 5,5-dimethyltetrahydrofuran-2-ylmethyl; and hetaryl-$C_1$-$C_5$-alkyl, in particular hetarylmethyl, 1-hetarylethyl or 2-hetarylethyl, wherein the hetaryl radicals may be unsubstituted or may carry 1, 2 or 3 radicals $R^y$ as defined above, e.g. furan-2-ylmethyl, furan-2-ylmethyl, 5-methylfuran-2-ylmethyl, thiophen-2-ylmethyl, thiophen-3-ylmethyl, isothiazol-3-ylmethyl, isothiazol-4-ylmethyl, isothiazol-5-ylmethyl, isoxazol-3-ylmethyl, isoxazol-4-ylmethyl, isoxazol-5-ylmethyl, oxazol-2-ylmethyl, oxazol-4-ylmethyl, oxazol-5-ylmethyl, thiazol-2-ylmethyl, thiazol-4-ylmethyl, thiazol-5-ylmethyl, 1H-pyrazol-3-ylmethyl, 1H-pyrazol-4-ylmethyl, 2H-pyrazol-3-ylmethyl, 1-methyl-1H-pyrazol-3-ylmethyl, 1-methyl-1H-pyrazol-4-ylmethyl, 2-methyl-2H-pyrazol-3-ylmethyl, 1H-imidazol-2-ylmethyl, 1H-imidazol-4-ylmethyl, 1H-imidazol-5-ylmethyl, 1-methyl-1H-imidazol-2-ylmethyl, 1-methyl-1H-imidazol-4-ylmethyl, 1-methyl-1H-imidazol-5-ylmethyl, pyridin-2-ylmethyl or pyridin-3-ylmethyl.

A particular embodiment relates to compounds of the formulae I and II, wherein A is a radical A1 with Z being a radical $R^N$, wherein $R^N$ is selected from hydrogen, $C_1$-$C_{10}$-alkyl, $C_1$-$C_{10}$-haloalkyl, $C_2$-$C_{10}$-alkenyl, $C_2$-$C_{10}$-haloalkenyl, $C_1$-$C_4$-alkoxy-$C_1$-$C_{10}$-alkyl, $C_1$-$C_4$-alkylene-CN, $C_3$-$C_{10}$-cycloalkyl, $C_3$-$C_{10}$-cycloalkyl-$C_1$-$C_4$-alkyl, heterocyclyl, heterocyclyl-$C_1$-$C_4$-alkyl, in particular heterocyclylmethyl, phenyl, phenyl-$C_1$-$C_4$-alkyl, in particular benzyl, 5- or 6-membered hetarylmethyl, wherein the cycloalkyl, heterocyclyl, phenyl or hetaryl ring in the nine last mentioned radicals may be unsubstituted or may carry 1, 2, 3, 4 or 5 identical or different substituents selected from CN, halogen, $C_1$-$C_4$-alkyl, $C_1$-$C_4$-haloalkyl, $C_1$-$C_4$-alkoxy and $C_1$-$C_4$-haloalkoxy. More preferably, $R^N$ is selected from hydrogen, $C_1$-$C_6$-alkyl, $C_1$-$C_6$-haloalkyl, heterocyclyl-$C_1$-$C_4$-alkyl, $C_1$-$C_4$-alkoxy-$C_1$-$C_4$-alkyl, $C_1$-$C_4$-alkylene-CN, $C_3$-$C_6$-cycloalkyl, $C_3$-$C_6$-cycloalkyl-$C_1$-$C_4$-alkyl, where the cycloalkyl moiety in the last two mentioned radicals is unsubstituted or carries 1 or 2 radicals selected from halogen, CN and $C_1$-$C_2$-haloalkyl. In particular, $R^N$ is $C_1$-$C_4$-alkyl, $C_1$-$C_4$-haloalkyl, $C_1$-$C_2$-alkoxy-$C_2$-$C_4$-alkyl, $C_1$-$C_4$-alkylene-CN, $C_3$-$C_6$-cycloalkyl and $C_3$-$C_6$-cycloalkylmethyl, where the cycloalkyl moiety in the last two mentioned radicals is unsubstituted or carries 1 or 2 radicals selected from halogen, CN and $C_1$-$C_2$-haloalkyl.

Especially, $R^N$, if present is $C_1$-$C_4$-alkyl or $C_1$-$C_4$-haloalkyl, $C_1$-$C_2$-alkoxy-$C_2$-$C_4$-alkyl, $C_3$-$C_6$-cycloalkylmethyl or $C_1$-$C_4$-alkylene-CN.

Examples of suitable radicals $R^N$ are: H, $CH_3$, $CH_2CH_3$, $CH_2CH_2CH_3$, $CH(CH_3)_2$, $CH_2CH_2CH_2CH_3$, $CH_2CH(CH_3)_2$, $C(CH_3)_3$, $CH_2F$, $CHF_2$, $CF_3$, $CH_2CHF_2$, $CH_2CF_3$, $CH_2Cl$, $CHCl_2$, $CCl_3$, $CH_2CHCl_2$, $CH_2CCl_3$, $CH_2OCH_3$, $CH_2CH_2OCH_3$, $CH_2CH_2OCH_3$, $CH_2CH_2CN$, 2-cyano-1-methyl-ethyl, 2-cyano-2-methyl-ethyl, vinyl, 2-propenyl, cyclopropyl, cyclopropylmethyl, 1-fluorocyclopropyl, 1-chlorocyclopropyl, 2,2-dichlorocyclopropylmethyl, 1-fluorocyclopropylmethyl, 1-chlorocyclopropylmethyl, 1-trifluoromethylcyclopropylmethyl, 1-cyanocyclopropylmethyl, $C_6H_5$, 4-$CH_3$—$C_6H_4$, 4-$C(CH_3)_3$—$C_6H_4$, 4-phenyl-$C_6H_4$, 4-$NO_2$—$C_6H_4$, 4-F—$C_6H_4$, 4-Cl—$C_6H_4$, 4-$CF_3$—$C_6H_4$, 4-$(CF(CF_3)_2)$—$C_6H_4$, 4-$(SO_2CH_3)$—$C_6H_4$, 4-$(SCF_3)$—$C_6H_4$, 4-$(OCHF_2)$—$C_6H_4$, 4-$(OCF_3)$—$C_6H_4$, 4-$(CH_3O)$—$C_6H_4$, 3-phenyl-$C_6H_4$, 3-$NO_2$—$C_6H_4$, 3-F—$C_6H_4$, 3-Cl—$C_6H_4$, 3-Cl-4-F—$C_6H_3$, 3-$CH_3O$—$C_6H_4$, 3-$CH_3$—$C_6H_4$, 3,5-$Cl_2$-$C_6H_3$, 3,4-$Cl_2$-$C_6H_3$, 2-phenyl-$C_6H_4$, 2-$NO_2$—$C_6H_4$, 2-F—$C_6H_4$, 2-F-4-Cl—$C_6H_3$, 2-$CH_3O$—$C_6H_4$, 2-$CH_3$—$C_6H_4$, 2-$CF_3$—$C_6H_4$, 2,6-$F_2$-$C_6H_3$, 2,6-Cl-4-$CF_3$—$C_6H_2$, 2,4-$F_2$—$C_6H_3$, 2,4-$Cl_2$-$C_6H_3$, 2,4,6-$Cl_3$-$C_6H_2$, 2,3,4-$Cl_3$-$C_6H_2$, benzyl and 4-chlorobenzyl.

Each group of suitable and preferred radicals A1 of the following examples constitutes an embodiment of the invention.

Preferred radicals A1 are the radicals of the formula A1.Za,

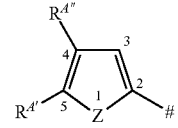

A1•Za wherein # denotes the attachment point to the remainder of the compound of formulae I and II, Z is as defined above, $R^{A'}$ is hydrogen or has one of the meanings given for $R^A$, and $R^{A''}$ is hydrogen or has one of the meanings given for $R^A$.

The positional numbering of the atoms in the 5-membered ring depicted in formula A1.Za is the same as in formula A1: Z is in the number 1 position and the binding site to the remainder of the compound I or II is in the number 2 position.

Examples of particularly preferred radicals A1 are the radicals of the formula A1.Za, wherein Z is O, $R^{A'}$ and $R^{A''}$ are radicals $R^A$, as defined herein, at the indicated positions of the 5-membered ring, and each combination of the radicals $R^{A'}$ and $R^{A''}$ is represented by one line of Table $R^A$. These radicals A1.Za are numbered A1.Oa1 to A1.Oa420.

TABLE $R^A$

| Line | Radical $R^{A'}$ | Radical $R^{A''}$ |
|---|---|---|
| 1 | H | H |
| 2 | $CH_3$ | H |
| 3 | $CH_2CH_3$ | H |
| 4 | $CH_2CH_2CH_3$ | H |
| 5 | isoproyl | H |
| 6 | cyclopropyl | H |
| 7 | $CF_3$ | H |
| 8 | $CHF_2$ | H |
| 9 | $CH(F)CH_3$ | H |
| 10 | $OCH_3$ | H |
| 11 | $OC_2H_5$ | H |
| 12 | $OCHF_2$ | H |
| 13 | CN | H |

TABLE R^A-continued

| Line | Radical R^A' | Radical R^A'' |
|---|---|---|
| 14 | F | H |
| 15 | Cl | H |
| 16 | Br | H |
| 17 | NO$_2$ | H |
| 18 | acetyl | H |
| 19 | benzoyl | H |
| 20 | 3-CF$_3$-phenyl | H |
| 21 | 2-methoxy-4-nitrophenyl | H |
| 22 | 4-Cl-phenyl | H |
| 23 | 2,5-dichlorophenyl | H |
| 24 | 2-nitro-phenoxymethyl | H |
| 25 | 4-ethoxy-phenoxymethyl | H |
| 26 | 4-isopropyl-phenoxymethyl | H |
| 27 | 4-tert-butyl-phenoxymethyl | H |
| 28 | 3,5-dimethyl-pyrazol-1-ylmethyl | H |
| 29 | H | CH$_3$ |
| 30 | CH$_3$ | CH$_3$ |
| 31 | CH$_2$CH$_3$ | CH$_3$ |
| 32 | CH$_2$CH$_2$CH$_3$ | CH$_3$ |
| 33 | isopropyl | CH$_3$ |
| 34 | cyclopropyl | CH$_3$ |
| 35 | CF$_3$ | CH$_3$ |
| 36 | CHF$_2$ | CH$_3$ |
| 37 | CH(F)CH$_3$ | CH$_3$ |
| 38 | OCH$_3$ | CH$_3$ |
| 39 | OC$_2$H$_5$ | CH$_3$ |
| 40 | OCHF$_2$ | CH$_3$ |
| 41 | CN | CH$_3$ |
| 42 | F | CH$_3$ |
| 43 | Cl | CH$_3$ |
| 44 | Br | CH$_3$ |
| 45 | NO$_2$ | CH$_3$ |
| 46 | acetyl | CH$_3$ |
| 47 | benzoyl | CH$_3$ |
| 48 | 3-CF$_3$-phenyl | CH$_3$ |
| 49 | 2-methoxy-4-nitrophenyl | CH$_3$ |
| 50 | 4-Cl-phenyl | CH$_3$ |
| 51 | 2,5-dichlorophenyl | CH$_3$ |
| 52 | 2-nitro-phenoxymethyl | CH$_3$ |
| 53 | 4-ethoxy-phenoxymethyl | CH$_3$ |
| 54 | 4-isopropyl-phenoxymethyl | CH$_3$ |
| 55 | 4-tert-butyl-phenoxymethyl | CH$_3$ |
| 56 | 3,5-dimethyl-pyrazol-1-ylmethyl | CH$_3$ |
| 57 | H | CH$_2$CH$_3$ |
| 58 | CH$_3$ | CH$_2$CH$_3$ |
| 59 | CH$_2$CH$_3$ | CH$_2$CH$_3$ |
| 60 | CH$_2$CH$_2$CH$_3$ | CH$_2$CH$_3$ |
| 61 | isoproyl | CH$_2$CH$_3$ |
| 62 | cyclopropyl | CH$_2$CH$_3$ |
| 63 | CF$_3$ | CH$_2$CH$_3$ |
| 64 | CHF$_2$ | CH$_2$CH$_3$ |
| 65 | CH(F)CH$_3$ | CH$_2$CH$_3$ |
| 66 | OCH$_3$ | CH$_2$CH$_3$ |
| 67 | OC$_2$H$_5$ | CH$_2$CH$_3$ |
| 68 | OCHF$_2$ | CH$_2$CH$_3$ |
| 69 | CN | CH$_2$CH$_3$ |
| 70 | F | CH$_2$CH$_3$ |
| 71 | Cl | CH$_2$CH$_3$ |
| 72 | Br | CH$_2$CH$_3$ |
| 73 | NO$_2$ | CH$_2$CH$_3$ |
| 74 | acetyl | CH$_2$CH$_3$ |
| 75 | benzoyl | CH$_2$CH$_3$ |
| 76 | 3-CF$_3$-phenyl | CH$_2$CH$_3$ |
| 77 | 2-methoxy-4-nitrophenyl | CH$_2$CH$_3$ |
| 78 | 4-Cl-phenyl | CH$_2$CH$_3$ |
| 79 | 2,5-dichlorophenyl | CH$_2$CH$_3$ |
| 80 | 2-nitro-phenoxymethyl | CH$_2$CH$_3$ |
| 81 | 4-ethoxy-phenoxymethyl | CH$_2$CH$_3$ |
| 82 | 4-isopropyl-phenoxymethyl | CH$_2$CH$_3$ |
| 83 | 4-tert-butyl-phenoxymethyl | CH$_2$CH$_3$ |
| 84 | 3,5-dimethyl-pyrazol-1-ylmethyl | CH$_2$CH$_3$ |
| 85 | H | CH$_2$CH$_2$CH$_3$ |
| 86 | CH$_3$ | CH$_2$CH$_2$CH$_3$ |
| 87 | CH$_2$CH$_3$ | CH$_2$CH$_2$CH$_3$ |
| 88 | CH$_2$CH$_2$CH$_3$ | CH$_2$CH$_2$CH$_3$ |
| 89 | isopropyl | CH$_2$CH$_2$CH$_3$ |
| 90 | cyclopropyl | CH$_2$CH$_2$CH$_3$ |
| 91 | CF$_3$ | CH$_2$CH$_2$CH$_3$ |
| 92 | CHF$_2$ | CH$_2$CH$_2$CH$_3$ |
| 93 | CH(F)CH$_3$ | CH$_2$CH$_2$CH$_3$ |
| 94 | OCH$_3$ | CH$_2$CH$_2$CH$_3$ |
| 95 | OC$_2$H$_5$ | CH$_2$CH$_2$CH$_3$ |
| 96 | OCHF$_2$ | CH$_2$CH$_2$CH$_3$ |
| 97 | CN | CH$_2$CH$_2$CH$_3$ |
| 98 | F | CH$_2$CH$_2$CH$_3$ |
| 99 | Cl | CH$_2$CH$_2$CH$_3$ |
| 100 | Br | CH$_2$CH$_2$CH$_3$ |
| 101 | NO$_2$ | CH$_2$CH$_2$CH$_3$ |
| 102 | acetyl | CH$_2$CH$_2$CH$_3$ |
| 103 | benzoyl | CH$_2$CH$_2$CH$_3$ |
| 104 | 3-CF$_3$-phenyl | CH$_2$CH$_2$CH$_3$ |
| 105 | 2-methoxy-4-nitrophenyl | CH$_2$CH$_2$CH$_3$ |
| 106 | 4-Cl-phenyl | CH$_2$CH$_2$CH$_3$ |
| 107 | 2,5-dichlorophenyl | CH$_2$CH$_2$CH$_3$ |
| 108 | 2-nitro-phenoxymethyl | CH$_2$CH$_2$CH$_3$ |
| 109 | 4-ethoxy-phenoxymethyl | CH$_2$CH$_2$CH$_3$ |
| 110 | 4-isopropyl-phenoxymethyl | CH$_2$CH$_2$CH$_3$ |
| 111 | 4-tert-butyl-phenoxymethyl | CH$_2$CH$_2$CH$_3$ |
| 112 | 3,5-dimethyl-pyrazol-1-ylmethyl | CH$_2$CH$_2$CH$_3$ |
| 113 | H | cyclopropyl |
| 114 | CH$_3$ | cyclopropyl |
| 115 | CH$_2$CH$_3$ | cyclopropyl |
| 116 | CH$_2$CH$_2$CH$_3$ | cyclopropyl |
| 117 | isoproyl | cyclopropyl |
| 118 | cyclopropyl | cyclopropyl |
| 119 | CF$_3$ | cyclopropyl |
| 120 | CHF$_2$ | cyclopropyl |
| 121 | CH(F)CH$_3$ | cyclopropyl |
| 122 | OCH$_3$ | cyclopropyl |
| 123 | OC$_2$H$_5$ | cyclopropyl |
| 124 | OCHF$_2$ | cyclopropyl |
| 125 | CN | cyclopropyl |
| 126 | F | cyclopropyl |
| 127 | Cl | cyclopropyl |
| 128 | Br | cyclopropyl |
| 129 | NO$_2$ | cyclopropyl |
| 130 | acetyl | cyclopropyl |
| 131 | benzoyl | cyclopropyl |
| 132 | 3-CF$_3$-phenyl | cyclopropyl |
| 133 | 2-methoxy-4-nitrophenyl | cyclopropyl |
| 134 | 4-Cl-phenyl | cyclopropyl |
| 135 | 2,5-dichlorophenyl | cyclopropyl |
| 136 | 2-nitro-phenoxymethyl | cyclopropyl |
| 137 | 4-ethoxy-phenoxymethyl | cyclopropyl |
| 138 | 4-isopropyl-phenoxymethyl | cyclopropyl |
| 139 | 4-tert-butyl-phenoxymethyl | cyclopropyl |
| 140 | 3,5-dimethyl-pyrazol-1-ylmethyl | cyclopropyl |
| 141 | H | CF$_3$ |
| 142 | CH$_3$ | CF$_3$ |
| 143 | CH$_2$CH$_3$ | CF$_3$ |
| 144 | CH$_2$CH$_2$CH$_3$ | CF$_3$ |
| 145 | isopropyl | CF$_3$ |
| 146 | cyclopropyl | CF$_3$ |
| 147 | CF$_3$ | CF$_3$ |
| 148 | CHF$_2$ | CF$_3$ |
| 149 | CH(F)CH$_3$ | CF$_3$ |
| 150 | OCH$_3$ | CF$_3$ |
| 151 | OC$_2$H$_5$ | CF$_3$ |
| 152 | OCHF$_2$ | CF$_3$ |
| 153 | CN | CF$_3$ |
| 154 | F | CF$_3$ |
| 155 | Cl | CF$_3$ |
| 156 | Br | CF$_3$ |
| 157 | NO$_2$ | CF$_3$ |
| 158 | acetyl | CF$_3$ |
| 159 | benzoyl | CF$_3$ |
| 160 | 3-CF$_3$-phenyl | CF$_3$ |
| 161 | 2-methoxy-4-nitrophenyl | CF$_3$ |
| 162 | 4-Cl-phenyl | CF$_3$ |
| 163 | 2,5-dichlorophenyl | CF$_3$ |
| 164 | 2-nitro-phenoxymethyl | CF$_3$ |
| 165 | 4-ethoxy-phenoxymethyl | CF$_3$ |
| 166 | 4-isopropyl-phenoxymethyl | CF$_3$ |
| 167 | 4-tert-butyl-phenoxymethyl | CF$_3$ |
| 168 | 3,5-dimethyl-pyrazol-1-ylmethyl | CF$_3$ |
| 169 | H | CHF$_2$ |

TABLE R^A-continued

| Line | Radical R^A' | Radical R^A'' |
|---|---|---|
| 170 | CH₃ | CHF₂ |
| 171 | CH₂CH₃ | CHF₂ |
| 172 | CH₂CH₂CH₃ | CHF₂ |
| 173 | isopropyl | CHF₂ |
| 174 | cyclopropyl | CHF₂ |
| 175 | CF₃ | CHF₂ |
| 176 | CHF₂ | CHF₂ |
| 177 | CH(F)CH₃ | CHF₂ |
| 178 | OCH₃ | CHF₂ |
| 179 | OC₂H₅ | CHF₂ |
| 180 | OCHF₂ | CHF₂ |
| 181 | CN | CHF₂ |
| 182 | F | CHF₂ |
| 183 | Cl | CHF₂ |
| 184 | Br | CHF₂ |
| 185 | NO₂ | CHF₂ |
| 186 | acetyl | CHF₂ |
| 187 | benzoyl | CHF₂ |
| 188 | 3-CF₃-phenyl | CHF₂ |
| 189 | 2-methoxy-4-nitrophenyl | CHF₂ |
| 190 | 4-Cl-phenyl | CHF₂ |
| 191 | 2,5-dichlorophenyl | CHF₂ |
| 192 | 2-nitro-phenoxymethyl | CHF₂ |
| 193 | 4-ethoxy-phenoxymethyl | CHF₂ |
| 194 | 4-isopropyl-phenoxymethyl | CHF₂ |
| 195 | 4-tert-butyl-phenoxymethyl | CHF₂ |
| 196 | 3,5-dimethyl-pyrazol-1-ylmethyl | CHF₂ |
| 197 | H | CH(F)CH₃ |
| 198 | CH₃ | CH(F)CH₃ |
| 199 | CH₂CH₃ | CH(F)CH₃ |
| 200 | CH₂CH₂CH₃ | CH(F)CH₃ |
| 201 | isopropyl | CH(F)CH₃ |
| 202 | cyclopropyl | CH(F)CH₃ |
| 203 | CF₃ | CH(F)CH₃ |
| 204 | CHF₂ | CH(F)CH₃ |
| 205 | CH(F)CH₃ | CH(F)CH₃ |
| 206 | OCH₃ | CH(F)CH₃ |
| 207 | OC₂H₅ | CH(F)CH₃ |
| 208 | OCHF₂ | CH(F)CH₃ |
| 209 | CN | CH(F)CH₃ |
| 210 | F | CH(F)CH₃ |
| 211 | Cl | CH(F)CH₃ |
| 212 | Br | CH(F)CH₃ |
| 213 | NO₂ | CH(F)CH₃ |
| 214 | acetyl | CH(F)CH₃ |
| 215 | benzoyl | CH(F)CH₃ |
| 216 | 3-CF₃-phenyl | CH(F)CH₃ |
| 217 | 2-methoxy-4-nitrophenyl | CH(F)CH₃ |
| 218 | 4-Cl-phenyl | CH(F)CH₃ |
| 219 | 2,5-dichlorophenyl | CH(F)CH₃ |
| 220 | 2-nitro-phenoxymethyl | CH(F)CH₃ |
| 221 | 4-ethoxy-phenoxymethyl | CH(F)CH₃ |
| 222 | 4-isopropyl-phenoxymethyl | CH(F)CH₃ |
| 223 | 4-tert-butyl-phenoxymethyl | CH(F)CH₃ |
| 224 | 3,5-dimethyl-pyrazol-1-ylmethyl | CH(F)CH₃ |
| 225 | H | OCH₃ |
| 226 | CH₃ | OCH₃ |
| 227 | CH₂CH₃ | OCH₃ |
| 228 | CH₂CH₂CH₃ | OCH₃ |
| 229 | isopropyl | OCH₃ |
| 230 | cyclopropyl | OCH₃ |
| 231 | CF₃ | OCH₃ |
| 232 | CHF₂ | OCH₃ |
| 233 | CH(F)CH₃ | OCH₃ |
| 234 | OCH₃ | OCH₃ |
| 235 | OC₂H₅ | OCH₃ |
| 236 | OCHF₂ | OCH₃ |
| 237 | CN | OCH₃ |
| 238 | F | OCH₃ |
| 239 | Cl | OCH₃ |
| 240 | Br | OCH₃ |
| 241 | NO₂ | OCH₃ |
| 242 | acetyl | OCH₃ |
| 243 | benzoyl | OCH₃ |
| 244 | 3-CF₃-phenyl | OCH₃ |
| 245 | 2-methoxy-4-nitrophenyl | OCH₃ |
| 246 | 4-Cl-phenyl | OCH₃ |
| 247 | 2,5-dichlorophenyl | OCH₃ |
| 248 | 2-nitro-phenoxymethyl | OCH₃ |
| 249 | 4-ethoxy-phenoxymethyl | OCH₃ |
| 250 | 4-isopropyl-phenoxymethyl | OCH₃ |
| 251 | 4-tert-butyl-phenoxymethyl | OCH₃ |
| 252 | 3,5-dimethyl-pyrazol-1-ylmethyl | OCH₃ |
| 253 | H | OCHF₂ |
| 254 | CH₃ | OCHF₂ |
| 255 | CH₂CH₃ | OCHF₂ |
| 256 | CH₂CH₂CH₃ | OCHF₂ |
| 257 | isopropyl | OCHF₂ |
| 258 | cyclopropyl | OCHF₂ |
| 259 | CF₃ | OCHF₂ |
| 260 | CHF₂ | OCHF₂ |
| 261 | CH(F)CH₃ | OCHF₂ |
| 262 | OCH₃ | OCHF₂ |
| 263 | OC₂H₅ | OCHF₂ |
| 264 | OCHF₂ | OCHF₂ |
| 265 | CN | OCHF₂ |
| 266 | F | OCHF₂ |
| 267 | Cl | OCHF₂ |
| 268 | Br | OCHF₂ |
| 269 | NO₂ | OCHF₂ |
| 270 | acetyl | OCHF₂ |
| 271 | benzoyl | OCHF₂ |
| 272 | 3-CF₃-phenyl | OCHF₂ |
| 273 | 2-methoxy-4-nitrophenyl | OCHF₂ |
| 274 | 4-Cl-phenyl | OCHF₂ |
| 275 | 2,5-dichlorophenyl | OCHF₂ |
| 276 | 2-nitro-phenoxymethyl | OCHF₂ |
| 277 | 4-ethoxy-phenoxymethyl | OCHF₂ |
| 278 | 4-isopropyl-phenoxymethyl | OCHF₂ |
| 279 | 4-tert-butyl-phenoxymethyl | OCHF₂ |
| 280 | 3,5-dimethyl-pyrazol-1-ylmethyl | OCHF₂ |
| 281 | H | CN |
| 282 | CH₃ | CN |
| 283 | CH₂CH₃ | CN |
| 284 | CH₂CH₂CH₃ | CN |
| 285 | isopropyl | CN |
| 286 | cyclopropyl | CN |
| 287 | CF₃ | CN |
| 288 | CHF₂ | CN |
| 289 | CH(F)CH₃ | CN |
| 290 | OCH₃ | CN |
| 291 | OC₂H₅ | CN |
| 292 | OCHF₂ | CN |
| 293 | CN | CN |
| 294 | F | CN |
| 295 | Cl | CN |
| 296 | Br | CN |
| 297 | NO₂ | CN |
| 298 | acetyl | CN |
| 299 | benzoyl | CN |
| 300 | 3-CF₃-phenyl | CN |
| 301 | 2-methoxy-4-nitrophenyl | CN |
| 302 | 4-Cl-phenyl | CN |
| 303 | 2,5-dichlorophenyl | CN |
| 304 | 2-nitro-phenoxymethyl | CN |
| 305 | 4-ethoxy-phenoxymethyl | CN |
| 306 | 4-isopropyl-phenoxymethyl | CN |
| 307 | 4-tert-butyl-phenoxymethyl | CN |
| 308 | 3,5-dimethyl-pyrazol-1-ylmethyl | CN |
| 309 | H | F |
| 310 | CH₃ | F |
| 311 | CH₂CH₃ | F |
| 312 | CH₂CH₂CH₃ | F |
| 313 | isopropyl | F |
| 314 | cyclopropyl | F |
| 315 | CF₃ | F |
| 316 | CHF₂ | F |
| 317 | CH(F)CH₃ | F |
| 318 | OCH₃ | F |
| 319 | OC₂H₅ | F |
| 320 | OCHF₂ | F |
| 321 | CN | F |
| 322 | F | F |
| 323 | Cl | F |
| 324 | Br | F |
| 325 | NO₂ | F |

TABLE R$^A$-continued

| Line | Radical R$^{A'}$ | Radical R$^{A''}$ |
|---|---|---|
| 326 | acetyl | F |
| 327 | benzoyl | F |
| 328 | 3-CF$_3$-phenyl | F |
| 329 | 2-methoxy-4-nitrophenyl | F |
| 330 | 4-Cl-phenyl | F |
| 331 | 2,5-dichlorophenyl | F |
| 332 | 2-nitro-phenoxymethyl | F |
| 333 | 4-ethoxy-phenoxymethyl | F |
| 334 | 4-isopropyl-phenoxymethyl | F |
| 335 | 4-tert-butyl-phenoxymethyl | F |
| 336 | 3,5-dimethyl-pyrazol-1-ylmethyl | F |
| 337 | H | Cl |
| 338 | CH$_3$ | Cl |
| 339 | CH$_2$CH$_3$ | Cl |
| 340 | CH$_2$CH$_2$CH$_3$ | Cl |
| 341 | isopropyl | Cl |
| 342 | cyclopropyl | Cl |
| 343 | CF$_3$ | Cl |
| 344 | CHF$_2$ | Cl |
| 345 | CH(F)CH$_3$ | Cl |
| 346 | OCH$_3$ | Cl |
| 347 | OC$_2$H$_5$ | Cl |
| 348 | OCHF$_2$ | Cl |
| 349 | CN | Cl |
| 350 | F | Cl |
| 351 | Cl | Cl |
| 352 | Br | Cl |
| 353 | NO$_2$ | Cl |
| 354 | acetyl | Cl |
| 355 | benzoyl | Cl |
| 356 | 3-CF$_3$-phenyl | Cl |
| 357 | 2-methoxy-4-nitrophenyl | Cl |
| 358 | 4-Cl-phenyl | Cl |
| 359 | 2-nitro-phenyloxymethyl | Cl |
| 360 | 4-ethoxy-phenoxymethyl | Cl |
| 361 | 4-isopropyl-phenoxymethyl | Cl |
| 362 | 4-tert-butyl-phenoxymethyl | Cl |
| 363 | 3,5-dimethyl-pyrazol-1-ylmethyl | Cl |
| 364 |  | Cl |
| 365 | H | Br |
| 366 | CH$_3$ | Br |
| 367 | CH$_2$CH$_3$ | Br |
| 368 | CH$_2$CH$_2$CH$_3$ | Br |
| 369 | isopropyl | Br |
| 370 | cyclopropyl | Br |
| 371 | CF$_3$ | Br |
| 372 | CHF$_2$ | Br |
| 373 | CH(F)CH$_3$ | Br |
| 374 | OCH$_3$ | Br |
| 375 | OC$_2$H$_5$ | Br |
| 376 | OCHF$_2$ | Br |
| 377 | CN | Br |
| 378 | F | Br |
| 379 | Cl | Br |
| 380 | Br | Br |
| 381 | NO$_2$ | Br |
| 382 | acetyl | Br |
| 383 | benzoyl | Br |
| 384 | 3-CF$_3$-phenyl | Br |
| 385 | 2-methoxy-4-nitrophenyl | Br |
| 386 | 4-Cl-phenyl | Br |
| 387 | 2,5-dichlorophenyl | Br |
| 388 | 2-nitro-phenoxymethyl | Br |
| 389 | 4-ethoxy-phenoxymethyl | Br |
| 390 | 4-isopropyl-phenoxymethyl | Br |
| 391 | 4-tert-butyl-phenoxymethyl | Br |
| 392 | 3,5-dimethyl-pyrazol-1-ylmethyl | Br |
| 393 | H | NO$_2$ |
| 394 | CH$_3$ | NO$_2$ |
| 395 | CH$_2$CH$_3$ | NO$_2$ |
| 396 | CH$_2$CH$_2$CH$_3$ | NO$_2$ |
| 397 | isopropyl | NO$_2$ |
| 398 | cyclopropyl | NO$_2$ |
| 399 | CF$_3$ | NO$_2$ |
| 400 | CHF$_2$ | NO$_2$ |
| 401 | CH(F)CH$_3$ | NO$_2$ |
| 402 | OCH$_3$ | NO$_2$ |
| 403 | OC$_2$H$_5$ | NO$_2$ |
| 404 | OCHF$_2$ | NO$_2$ |
| 405 | CN | NO$_2$ |
| 406 | F | NO$_2$ |
| 407 | Cl | NO$_2$ |
| 408 | Br | NO$_2$ |
| 409 | NO$_2$ | NO$_2$ |
| 410 | acetyl | NO$_2$ |
| 411 | benzoyl | NO$_2$ |
| 412 | 3-CF$_3$-phenyl | NO$_2$ |
| 413 | 2-methoxy-4-nitrophenyl | NO$_2$ |
| 414 | 4-Cl-phenyl | NO$_2$ |
| 415 | 2,5-dichlorophenyl | NO$_2$ |
| 416 | 2-nitro-phenoxymethyl | NO$_2$ |
| 417 | 4-ethoxy-phenoxymethyl | NO$_2$ |
| 418 | 4-isopropyl-phenoxymethyl | NO$_2$ |
| 419 | 4-tert-butyl-phenoxymethyl | NO$_2$ |
| 420 | 3,5-dimethyl-pyrazol-1-ylmethyl | NO$_2$ |

Preferred radicals A1 are further the radicals of the formula A1.Zb,

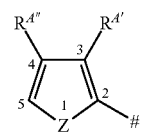

A1·Zb wherein # denotes the attachment point to the remainder of the compound of formulae I and II, Z is as defined above, R$^{A'}$ is hydrogen or has one of the meanings given for R$^A$, and R$^{A''}$ is hydrogen or has one of the meanings given for R$^A$.

Examples of particularly preferred radicals A1 are the radicals of the formula A1.Zb, wherein Z is O, R$^{A'}$ and R$^{A''}$ are radicals R$^A$, as defined herein, at the indicated positions of the 5-membered ring, and each combination of the radicals R$^{A'}$ and R$^{A''}$ is represented by one line of Table R$^A$. These radicals A1.Zb are numbered A1.Ob1 to A1.Ob420.

Preferred radicals A1 are further the radicals of the formula A1.Zc,

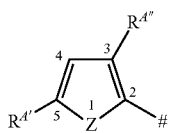

A1·Zc wherein # denotes the attachment point to the remainder of the compound of formulae I and II, Z is as defined above, R$^{A'}$ is hydrogen or has one of the meanings given for R$^A$, and R$^{A''}$ is hydrogen or has one of the meanings given for R$^A$.

Examples of particularly preferred radicals A1 are the radicals of the formula A1.Zc, wherein Z is O, R$^{A'}$ and R$^{A''}$ are radicals R$^A$, as defined herein, at the indicated positions of the 5-membered ring, and each combination of the radicals R$^{A'}$ and R$^{A''}$ is represented by one line of Table R$^A$. These radicals A1.Zc are numbered A1.Oc1 to A1.Oc420.

Further examples of suitable radicals A1 are the radicals numbered A1.Sa1 to A1.Sa420 having structures that are analog to the structures of the above radicals of numbers A1.Oa1 to A1.Oa420, wherein Z instead of O is S and each combination of the radicals R$^{A'}$ and R$^{A''}$ is represented by one line of Table R$^A$.

Further examples of suitable radicals A1 are the radicals numbered A1.Sb1 to A1.Sb420 having structures that are analog to the structures of the above radicals of numbers A1.Ob1 to A1.Ob420, wherein Z instead of O is S and each combination of the radicals $R^{A'}$ and $R^{A''}$ is represented by one line of Table $R^A$.

Further examples of suitable radicals A1 are the radicals numbered A1.Sc1 to A1.Sc420 having structures that are analog to the structures of the above radicals of numbers A1.Oc1 to A1.Oc420, wherein Z instead of O is S and each combination of the radicals $R^{A'}$ and $R^{A''}$ is represented by one line of Table $R^A$.

Further examples of suitable radicals A1 are the radicals numbered A1.1Na1 to A1.126Na420 having structures that are analog to the structures of the above radicals of numbers A1.Oa1 to A1.Oa420, wherein each combination of the radicals $R^{A'}$ and $R^{A''}$ is represented by one line of Table $R^A$ and Z instead of O is $NR^N$ with $R^N$ in each case being represented by one line of the following Table $R^N$. Thus, the set of radicals A1.1Na1 to A1.126Na420 comprises 52920 individual radicals A1.vNaw, wherein the variable v denotes the radical in line v of Table $R^N$ and the variable w denotes the combination of radicals $R^{A'}$ and $R^{A''}$ in line w of Table $R^A$.

Particular preferred examples of radicals A1.Za with Z being N—$R^N$ are the radicals A1.1Na1 to A1.1Na420, A1.2Na1 to A1.2Na420, A1.3Na1 to A1.3Na420, A1.6Na1 to A1.6Na420, A1.83Na1 to A1.83Na420, A1.84Na1 to A1.84Na420, A1.85Na1 to A1.85Na420, A1.87Na1 to A1.87Na420 and A1.94Na1 to A1.94Na420, wherein $R^N$ is hydrogen, methyl, ethyl, isobutyl (=2-methylpropyl), cyclopropylmethyl (cyclopropyl-$CH_2$—), 2,2,2-trifluoroethyl, cyanomethyl, methoxymethyl, 2-methoxyethyl or ethoxymethyl, respectively.

Further examples of suitable radicals A1 are the radicals numbered A1.1Nb1 to A1.126Nb420 having structures that are analog to the structures of the above radicals of numbers A1.Ob1 to A1.Ob420, wherein each combination of the radicals $R^{A'}$ and $R^{A''}$ is represented by one line of Table $R^A$ and Z instead of O is $NR^N$ with $R^N$ in each case being represented by one line of the following Table $R^N$. Thus, the set of radicals A1.1Nb1 to A1.126Nb420 comprises 52920 individual radicals A1.vNbw, wherein the variable v denotes the radical in line v of Table $R^N$ and the variable w denotes the combination of radicals $R^{A'}$ and $R^{A''}$ in line w of Table $R^A$.

Examples of radicals A1.Zb with Z being N—$R^N$ are the radicals A1.1Nb1 to A1.1Nb420, A1.2Nb1 to A1.2Nb420, A1.3Nb1 to A1.3Nb420, A1.6Nb1 to A1.6Nb420, A1.82Nb1 to A1.82Nb420, A1.83Nb1 to A1.83Nb420, A1.84Nb1 to A1.84Nb420, A1.85Nb1 to A1.85Nb420, A1.87Nb1 to A1.87Nb420 and A1.84Nb1 to A1.84Nb420, wherein $R^N$ is hydrogen, methyl, ethyl, isobutyl, cyclopropylmethyl, 2,2,2-trifluoroethyl, cyanomethyl, methoxymethyl, 2-methoxyethyl or ethoxymethyl, respectively.

Further examples of suitable radicals A1 are the radicals numbered A1.1Nc1 to A1.126Nc420 having structures that are analog to the structures of the above radicals of numbers A1.Oc1 to A1.Oc420, wherein each combination of the radicals $R^{A'}$ and $R^{A''}$ is represented by one line of Table $R^A$ and Z instead of O is $NR^N$ with $R^N$ in each case being represented by one line of the following Table $R^N$. Thus, the set of radicals A1.1Nc1 to A1.126Nc420 comprises 52920 individual radicals A1.vNcw, wherein the variable v denotes the radical in line v of Table $R^N$ and the variable w denotes the combination of radicals $R^{A'}$ and $R^{A''}$ in line w of Table $R^A$.

Examples of radicals A1.Zc with Z being N—$R^N$ are the radicals A1.1Nc1 to A1.1Nc420, A1.2Nc1 to A1.2Nc420, A1.3Nc1 to A1.3Nc420, A1.6Nc1 to A1.6Nc420, A1.82Nc1 to A1.82Nc420, A1.83Nc1 to A1.83Nc420, A1.84Nc1 to A1.84Nc420, A1.85Nc1 to A1.85Nc420, A1.87Nc1 to A1.87Nc420 and A1.94Nc1 to A1.94Nc420, wherein $R^N$ is hydrogen, methyl, ethyl, isobutyl, cyclopropylmethyl, 2,2,2-trifluoroethyl, cyanomethyl, methoxymethyl, 2-methoxyethyl or ethoxymethyl, respectively.

TABLE $R^N$

| Line | Radical $R^N$ |
| --- | --- |
| 1 | H |
| 2 | $CH_3$ |
| 3 | $CH_2CH_3$ |
| 4 | $CH_2CH_2CH_3$ |
| 5 | $CH(CH_3)_2$ |
| 6 | $CH_2CF_3$ |
| 7 | $C(CH_3)_3$ |
| 8 | $C_6H_5$ |
| 9 | 4-Cl—$C_6H_4$ |
| 10 | 4-F—$C_6H_4$ |
| 11 | 2,4-$Cl_2$—$C_6H_3$ |
| 12 | 4-($CH_3O$)—$C_6H_4$ |
| 13 | 2-pyridyl |
| 14 | 5-chloro-2-pyridyl |
| 15 | $CH_2$—$C_6H_5$ |
| 16 | 4-($OCF_3$)—$C_6H_4$ |
| 17 | 4-($SCF_3$)—$C_6H_4$ |
| 18 | 4-($OCHF_2$)—$C_6H_4$ |
| 19 | 4-($CF(CF_3)_2$)—$C_6H_4$ |
| 20 | 4-($SO_2CH_3$)—$C_6H_4$ |
| 21 | 2,6-Cl-4-$CF_3$—$C_6H_2$ |
| 22 | 3-chloro-5-trifluoro-methylpyridine-2-yl |
| 23 | 3-pyridyl |
| 24 | 4-pyridyl |
| 25 | 2-thiazolyl |
| 26 | 4,5-dimethyl-thiazol-2-yl |
| 27 | 4-thiazolyl |
| 28 | 5-thiazolyl |
| 29 | 4-trifluormethyl-thiazol-2-yl |
| 30 | 4-methylthiazol-2-yl |
| 31 | 4-phenylthiazol-2-yl |
| 32 | 5-triazolyl |
| 33 | 3-methyl-triazol-5-yl |
| 34 | 4-chlorobenzyl |
| 35 | 4-nitro-1-pyrazolyl-methyl |
| 36 | 2-imidazolyl |
| 37 | 4-imidazolyl |
| 38 | 5-imidazolyl |
| 39 | 2-oxazolyl |
| 40 | 4-oxazolyl |
| 41 | 5-oxazolyl |
| 42 | 3-isoxazolyl |
| 43 | 4-isoxazolyl |
| 44 | 5-isoxazolyl |
| 45 | 3-methylisoxazol-5-yl |
| 46 | 5-methylisoxazol-3-yl |
| 47 | 3-pyrazolyl |
| 48 | [1,3,4]thiadiazol-2-yl |
| 49 | 5-tetrazolyl |
| 50 | 4-$NO_2$—$C_6H_4$ |
| 51 | 4-$CF_3$—$C_6H_4$ |
| 52 | 2,4-$F_2$—$C_6H_3$ |
| 53 | 3,5-$Cl_2$—$C_6H_3$ |
| 54 | 3,4-$Cl_2$—$C_6H_3$ |
| 55 | 4-$C(CH_3)_3$—$C_6H_4$ |
| 56 | 3-Cl—$C_6H_4$ |
| 57 | 3-F—$C_6H_4$ |
| 58 | 2-F—$C_6H_4$ |
| 59 | 2-$CF_3$—$C_6H_4$ |
| 60 | 2-$CH_3O$—$C_6H_4$ |
| 61 | 3-$CH_3O$—$C_6H_4$ |
| 62 | 3-Cl-4-F—$C_6H_3$ |
| 63 | 3-$NO_2$—$C_6H_4$ |
| 64 | 2-$CH_3$—$C_6H_4$ |
| 65 | 3-$CH_3$—$C_6H_4$ |
| 66 | 4-$CH_3$—$C_6H_4$ |
| 67 | 2-phenyl-$C_6H_4$ |
| 68 | 3-phenyl-$C_6H_4$ |
| 69 | 2-F-4-Cl—$C_6H_3$ |

TABLE $R^N$-continued

| Line | Radical $R^N$ |
|------|---------------|
| 70 | 2,4,6-Cl$_3$—C$_6$H$_2$ |
| 71 | 2,3,4-Cl$_3$—C$_6$H$_2$ |
| 72 | 2,6-F$_2$—C$_6$H$_3$ |
| 73 | CH$_2$F |
| 74 | CHF$_2$ |
| 75 | CF$_3$ |
| 76 | CH$_2$CHF$_2$ |
| 77 | CH$_2$Cl |
| 78 | CHCl$_2$ |
| 79 | CCl$_3$ |
| 80 | CH$_2$CHCl$_2$ |
| 81 | CH$_2$CCl$_3$ |
| 82 | CH$_2$CH(CH$_3$)$_2$ |
| 83 | CH$_2$OCH$_3$ |
| 84 | CH$_2$CH$_2$OCH$_3$ |
| 85 | CH$_2$OCH$_2$CH$_3$ |
| 86 | CH$_2$CH$_2$OCH$_2$CH$_3$ |
| 87 | CH$_2$CN |
| 88 | CH$_2$CH$_2$CN |
| 89 | 2-cyano-1-methyl-ethyl |
| 90 | 2-cyano-2-methyl-ethyl |
| 91 | cyclopropyl |
| 92 | 1-fluorocyclopropyl |
| 93 | 1-chlorocyclopropyl |
| 94 | cyclopropylmethyl |
| 95 | 1-fluorocyclopropylmethyl |
| 96 | 1-chlorocyclopropylmethyl |
| 97 | 1-trifluoromethylcyclopropylmethyl |
| 98 | 1-cyanocyclopropylmethyl |
| 99 | 2,2-dichlorocyclopropylmethyl |
| 100 | 2-NO$_2$—C$_6$H$_4$ |
| 101 | 6-chloro-2-pyridyl |
| 102 | 5-nitro-2-pyridyl |
| 103 | 3-nitro-2-pyridyl |
| 104 | 6-methyl-5-nitro-2-pyridyl |
| 105 | pyrazin-2-yl |
| 106 | pyrimidin-2-yl |
| 107 | thiophen-3-yl |
| 108 | 4-methyl-5-isopropyl-4H-[1,2,4]-triazol-3-yl |
| 109 | 4-methyl-5-cyclopropyl-4H-[1,2,4]-triazol-3-yl |
| 110 | 4-methyl-5-trifluoromethyl-4H-[1,2,4]-triazol-3-yl |
| 111 | 4,5-dimethyl-4H-[1,2,4]-triazol-3-yl |
| 112 | 4-methyl-5-ethyl-4H-[1,2,4]-triazol-3-yl |
| 113 | 4-isopropyl-4H-[1,2,4]-triazol-3-yl |
| 114 | 4-methyl-4H-[1,2,4]-triazol-3-yl |
| 115 | 4-ethyl-4H-[1,2,4]-triazol-3-yl |
| 116 | 4-phenyl-4H-[1,2,4]-triazol-3-yl |
| 117 | 5-methyl-1,3,4-thiadiazol-2-yl |
| 118 | vinyl |
| 119 | 2-propenyl |
| 120 | 5-phenyl-1,3,4-thiadiazol-2-yl |
| 121 | 5-trifluoromethyl-1,3,4-thiadiazol-2-yl |
| 122 | 5-phenyl-1,3,4-oxadiazol-2-yl |
| 123 | 5-trifluoromethyl-1,3,4-oxadiazol-2-yl |
| 124 | 5-methyl-1,3,4-oxadiazol-2-yl |
| 125 | 1-methyl-1,2,3-triazol-4-yl |
| 126 | 1-phenyl-1,2,3-triazol-4-yl |

The radicals of the formulae A1.Za1, A1.Zb1 and A1.Zc1 represent the same structure wherein the substituents in position 3, 4 and 5 are hydrogen.

Examples of radicals of the formula A1, wherein Z is O are in particular furan-2-yl, 5-(2,5-dichloro-phenyl)-furan-2-yl, 5-(2-methoxy-4-nitro-phenyl)-furan-2-yl, 5-(2-nitro-phenoxymethyl)-furan-2-yl, 5-(3,5-dimethyl-pyrazol-1-ylmethyl)-furan-2-yl, 5-(3-trifluoromethyl-phenyl)-furan-2-yl, 5-(4-chloro-phenyl)-furan-2-yl, 5-(4-ethoxy-phenoxymethyl)-furan-2-yl, 5-(4-isopropyl-phenoxymethyl)-furan-2-yl, 5-(4-tert-butyl-phenoxymethyl)-furan-2-yl, 5-benzoyl-furan-2-yl, 5-bromo-furan-2-yl and 5-nitro-furan-2-yl and 3-methyl-furan-2-yl.

Examples of radicals of the formula A1, wherein Z is S are in particular thiophene-2-yl, 3-bromo-thiophen-2-yl, 3-chloro-thiophen-2-yl, 3-methoxy-thiophene-2-yl, 3-methyl-thiophene-2-yl, 3-trifluoromethyl-thiophen-2-yl, 4-bromo-thiophen-2-yl, 5-bromo-thiophene-2-yl, 5-chloro-thiophen-2-yl, 5-methyl-thiophene-2-yl, 5-nitro-thiophene-2-yl, 5-trifluoromethyl-thiophen-2-yl and 3-ethoxy-5-methyl-thiophene-2-yl.

Examples of radicals of the formula A1, wherein Z is N—$R^N$ are in particular 1H-pyrrol-2-yl, 1-methyl-1H-pyrrol-2-yl, 1-ethyl-1H-pyrrol-2-yl, 1-(cyclopropylmethyl)-1H-pyrrol-2-yl, 1-(2-methylpropyl)-1H-pyrrol-2-yl, 1-(2,2,2-trifluoroethyl)-1H-pyrrol-2-yl, 1-cyanomethyl-1H-pyrrol-2-yl, 1-methoxymethyl-1H-pyrrol-2-yl, 1-ethoxymethyl-1H-pyrrol-2-yl, 1-(2-methoxyethyl)-1H-pyrrol-2-yl and 4-acetyl-3,5-dimethyl-1H-pyrrol-2-yl.

A further embodiment of the invention relates to pyridine compounds of formulae I and II, to the salts and N-oxides thereof and to the methods and uses of such compounds, wherein A is a radical A2.

Among the compounds, wherein A is a radical A2, preference is given to compounds of the formula I, wherein $X^1$, $R^1$, $R^2$, $R^3$ and $X^3$ are as defined above and in particular have one of the preferred meanings and n is 0. Likewise, preference is given to compounds of formula I, wherein A is a radical A2 and $X^1$, $R^1$, $R^2$, $R^3$ and $X^3$ are as defined above and in particular have one of the preferred meanings and n is 1. Likewise, preference is given to compounds of formula I, wherein A is a radical A2 and $X^1$, $R^1$, $R^2$, $R^3$ and $X^3$ are as defined above and in particular have one of the preferred meanings and n is 2. Likewise, preference is given to compounds of formula I, wherein A is a radical A2 and $X^1$, $X^2$, $R^1$, $R^2$, $R^3$ and $X^3$ are as defined above and in particular have one of the preferred meanings and n is 3.

Among the compounds of formulae I and II, wherein A is a radical A2, preference is given to those compounds, wherein Z is O.

Among the compounds of formulae I and II, wherein A is a radical A2, preference is further given to those compounds, wherein Z is S.

Among the compounds of formulae I and II, wherein A is a radical A2, preference is further given to those compounds, wherein Z is N—$R^N$. In this embodiment, $R^N$ has preferably one of the preferred or particularly preferred meanings given above in connection with the embodiments related to the radical A1, in particular hydrogen or one of the meanings given in lines 2 to 126 of Table $R^N$.

A further embodiment of the invention relates to compounds of formulae I and II, to their N-oxides and their salts, wherein in the radical $R^A$ of the formula A2 is absent, i.e. n is 0. It is understood that if n is 0, the radical A2 in formulae I and II is unsubstituted.

A further embodiment of the invention relates to compounds of formulae I and II, to their N-oxides and their salts, wherein A is a radical A2, wherein n is 1. In this embodiment, $R^A$ has preferably one of the preferred or particularly preferred meanings given above in connection with the embodiments related to the radical A1.

A further embodiment of the invention relates to compounds of formulae I and II, to their N-oxides and their salts, wherein A is a radical A2 and the substituents $R^A$ are in combination with other $R^A$, i.e. n is 2 or 3. In the formula A2, where the variable n is 2 or 3, $R^A$ may be identical or different. In this embodiment, $R^A$ has preferably one of the preferred or particularly preferred meanings given above in connection with the embodiments related to the radical A1.

Each group of suitable and preferred radicals A2 of the following examples constitutes an embodiment of the invention.

Preferred radicals A2 are the radicals of the formula A2.Za,

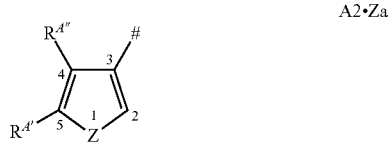

wherein # denotes the attachment point to the remainder of the compound of formulae I and II, Z is as defined above, $R^{A'}$ is hydrogen or has one of the meanings given for $R^A$, and $R^{A''}$ is hydrogen or has one of the meanings given for $R^A$.

The positional numbering of the atoms in the 5-membered ring depicted in formula A2.Za is the same as in formula A2: Z is in the number 1 position and the binding site to the remainder of the compound I or II is in the number 3 position.

Examples of particularly preferred radicals A2 are the radicals of the formula A2.Za, wherein Z is O, $R^{A'}$ and $R^{A''}$ are radicals $R^A$, as defined herein, at the indicated positions of the 5-membered ring, and each combination of the radicals $R^{A'}$ and $R^{A''}$ is represented by one line of Table $R^A$. These radicals A2.Za are numbered A2.Oa1 to A2.Oa420.

Preferred radicals A1 are further the radicals of the formula A2.Zb,

wherein # denotes the attachment point to the remainder of the compound of formulae I and II, Z is as defined above, $R^{A'}$ is hydrogen or has one of the meanings given for $R^A$, and $R^{A''}$ is hydrogen or has one of the meanings given for $R^A$.

Examples of particularly preferred radicals A2 are the radicals of the formula A2.Zb, wherein Z is O, $R^{A'}$ and $R^{A''}$ are radicals $R^A$, as defined herein, at the indicated positions of the 5-membered ring, and each combination of the radicals $R^{A'}$ and $R^{A''}$ is represented by one line of Table $R^A$. These radicals A2.Zb are numbered A2.Ob1 to A2.Ob420.

Preferred radicals A2 are further the radicals of the formula A2.Zc,

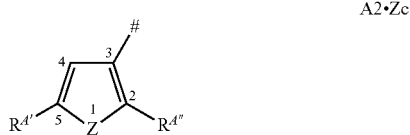

wherein # denotes the attachment point to the remainder of the compound of formulae I and II, Z is as defined above, $R^{A'}$ is hydrogen or has one of the meanings given for $R^A$, and $R^{A''}$ is hydrogen or has one of the meanings given for $R^A$.

Examples of particularly preferred radicals A2 are the radicals of the formula A2.Zc, wherein Z is O, $R^{A'}$ and $R^{A''}$ are radicals $R^A$, as defined herein, at the indicated positions of the 5-membered ring, and each combination of the radicals $R^{A'}$ and $R^{A''}$ is represented by one line of Table $R^A$. These radicals A2.Zc are numbered A2.Oc1 to A2.Oc420.

Further examples of suitable radicals A2 are the radicals numbered A2.Sa1 to A2.Sa420 having structures that are analog to the structures of the above radicals of numbers A2.Oa1 to A2.Oa420, wherein Z instead of O is S and each combination of the radicals $R^{A'}$ and $R^{A''}$ is represented by one line of Table $R^A$.

Further examples of suitable radicals A1 are the radicals numbered A2.Sb1 to A2.Sb420 having structures that are analog to the structures of the above radicals of numbers A2.Ob1 to A2.Ob420, wherein Z instead of O is S and each combination of the radicals $R^{A'}$ and $R^{A''}$ is represented by one line of Table $R^A$.

Further examples of suitable radicals A1 are the radicals numbered A2.Sc1 to A2.Sc420 having structures that are analog to the structures of the above radicals of numbers A2.Oc1 to A2.Oc420, wherein Z instead of O is S and each combination of the radicals $R^{A'}$ and $R^{A''}$ is represented by one line of Table $R^A$.

Further examples of suitable radicals A2 are the radicals numbered A2.1Na1 to A2.126Na420 having structures that are analog to the structures of the above radicals of numbers A2.Oa1 to A2.Oa420, wherein each combination of the radicals $R^{A'}$ and $R^{A''}$ is represented by one line of Table $R^A$ and Z instead of O is $NR^N$ with $R^N$ in each case being represented by one line of the following Table $R^N$. Thus, the set of radicals A2.1Na1 to A2.126Na420 comprises 52920 individual radicals A2.vNaw, wherein the variable v denotes the radical in line v of Table $R^N$ and the variable w denotes the combination of radicals $R^{A'}$ and $R^{A''}$ in line w of Table $R^A$.

Examples of particular preferred radicals A2.Za with Z being N—$R^N$ are the radicals A2.1Na1 to A2.1Na420, A2.2Na1 to A2.2Na420, A2.3Na1 to A2.3Na420, A2.6Na1 to A2.6Na420, A2.82Na1 to A2.82Na420, A2.83Na1 to A2.83Na420, A2.84Na1 to A2.84Na420, A2.85Na1 to A2.85Na420, A2.87Na1 to A2.87Na420 and A2.94Na1 to A2.94Na420, wherein $R^N$ is hydrogen, methyl, ethyl, isobutyl, cyclopropylmethyl, 2,2,2-trifluoroethyl, cyanomethyl, methoxymethyl, 2-methoxyethyl or ethoxymethyl, respectively.

Further examples of suitable radicals A2 are the radicals numbered A2.1Nb1 to A2.126Nb420 having structures that are analog to the structures of the above radicals of numbers A2.Ob1 to A2.Ob420, wherein each combination of the radicals $R^{A'}$ and $R^{A''}$ is represented by one line of Table $R^A$ and Z instead of O is $NR^N$ with $R^N$ in each case being represented by one line of the following Table $R^N$. Thus, the set of radicals A2.1Nb1 to A2.126Nb420 comprises 52920 individual radicals A2.vNbw, wherein the variable v denotes the radical in line v of Table $R^N$ and the variable w denotes the combination of radicals $R^{A'}$ and $R^{A''}$ in line w of Table $R^A$.

Examples of particular preferred radicals A2.Zb with Z being N—$R^N$ are the radicals A2.1 Nb1 to A2.1 Nb420, A2.2Nb1 to A2.2Nb420, A2.3Nb1 to A2.3Nb420, A2.6Nb1 to A2.6Nb420, A2.82Nb1 to A2.82Nb420, A2.83Nb1 to A2.83Nb420, A2.84Nb1 to A2.84Nb420, A2.85Nb1 to A2.85Nb420, A2.87Nb1 to A2.87Nb420 and A2.94Nb1 to A2.94Nb420, wherein $R^N$ is hydrogen, methyl, ethyl, isobutyl, cyclopropylmethyl, 2,2,2-trifluoromethyl, cyanomethyl, methoxymethyl, 2-methoxyethyl or ethoxymethyl, respectively.

Further examples of suitable radicals A2 are the radicals numbered A2.1Nc1 to A2.126Nc420 having structures that are analog to the structures of the above radicals of numbers A2.Oc1 to A2.Oc420, wherein each combination of the radicals $R^{A'}$ and $R^{A''}$ is represented by one line of Table $R^A$ and Z instead of O is NR$^N$ with R$^N$ in each case being represented by one line of the following Table R$^N$. Thus, the set of radicals A1.1Nc1 to A1.126Nc420 comprises 52920 individual radicals A2.vNcw, wherein the variable v denotes the radical in line v of Table R$^N$ and the variable w denotes the combination of radicals R$^{A'}$ and R$^{A''}$ in line w of Table R$^A$.

Examples of particular preferred radicals A2.Zc with Z being N—R$^N$ are the radicals A2.1Nc1 to A2.1Nc420, A2.2Nc1 to A2.2Nc420, A2.3Nc1 to A2.3Nc420, A2.6Nc1 to A2.6Nc420, A2.82Nc1 to A2.82Nc420, A2.83Nc1 to A2.83Nc420, A2.84Nc1 to A2.84Nc420, A2.85Nc1 to A2.85Nc420, A2.87Nb1 to A2.87Nb420 and A2.94Nc1 to A2.94Nc420, wherein R$^N$ is hydrogen, methyl, ethyl, isobutyl, cyclopropylmethyl, 2,2,2-trifluoromethyl, cyanomethyl, methoxymethyl, 2-methoxyethyl or ethoxymethyl, respectively.

The radicals of the type A2.Za1, A2.Zb1 and A2.Zc1 represent the same structure wherein the substituents in position 2, 4 and 5 are hydrogen.

Examples of radicals of the formula A2, wherein Z is O are in particular furan-3-yl, 2-methyl-furan-3-yl, 2,5-dimethyl-furan-3-yl, 5-methyl-2-trifluoromethyl-furan-3-yl and 5-(4-chloro-phenyl)-2-trifluoromethyl-furan-3-yl.

Examples of radicals of the formula A2, wherein Z is S are in particular thiophen-3-yl, 2-bromo-thiophen-3-yl, 2-chloro-thiophen-3-yl, 2-difluoromethoxy-thiophene-3-yl, 5-methyl-thiophen-3-yl, 5-isopropyl-thiophen-3-yl, 4-trifluoromethyl-thiophen-3-yl, 5-nitro-thiophen-3-yl, 2,5-dichloro-thiophen-3-yl, 2,5-dimethyl-thiophen-3-yl and 2,5-dichloro-thiophen-3-yl.

Examples of the radicals of the formula A2, wherein Z is N—R$^N$ are in particular such as 1H-pyrrol-3-yl, 1-methyl-1H-pyrrol-3-yl, 1-ethyl-1H-pyrrole-3-yl, 1-(2-methylpropyl)-1H-pyrrol-3-yl, 1-(2,2,2-trifluoroethyl)-1H-pyrrole-3-yl, 1-(cyclopropylmethyl)-1H-pyrrol-3-yl, 1-cyanomethyl-1H-pyrrol-3-yl, 1-methoxymethyl-1H-pyrrol-3-yl, 1-ethoxymethyl-1H-pyrrol-3-yl, 1-(2-methoxyethyl)-1H-pyrrole-3-yl.

Apart from that, the variables Y, R$^a$, R$^b$, R$^c$, R$^d$, R$^e$, R$^f$, R$^g$, R$^h$, R$^x$ and R$^y$ independently of each other, preferably have one of the following meanings:

Y is O;

R$^a$ is hydrogen, C$_1$-C$_4$-alkyl, C$_3$-C$_6$-cycloalkylmethyl, C$_3$-C$_6$-alkenyl, C$_3$-C$_6$-alkynyl and C$_1$-C$_4$-alkoxy-C$_1$-C$_4$-alkyl;

R$^b$, R$^c$ are independently of each other selected from hydrogen, C$_1$-C$_4$-alkyl, C$_1$-C$_4$-haloalkyl and phenyl, which is unsubstituted or carries 1, 2 or 3 substituents selected from cyano, nitro, C$_1$-C$_4$-alkyl, C$_1$-C$_4$-alkoxy and C$_1$-C$_4$-haloalkoxy;

R$^d$ is selected from C$_1$-C$_4$-alkyl and C$_1$-C$_4$-haloalkyl;

R$^e$, R$^f$ are independently of each other selected from hydrogen, C$_1$-C$_4$-alkyl, or R$^e$ and R$^f$ together with the nitrogen atom to which they are bound form a 5- or 6-membered, saturated heterocycle, which may carry a further heteroatom being selected from O, S and N as a ring member atom, e.g. pyrrolidin-1-yl, piperidin-1-yl, morpholin-4-yl, piperazin-1-yl or 4-methylpiperazin-1-yl;

R$^g$, R$^h$, R$^i$, are independently of each other selected from hydrogen and C$_1$-C$_4$-alkyl;

R$^x$ is C$_1$-C$_4$-alkoxy, C$_1$-C$_4$-haloalkoxy, C$_3$-C$_6$-cycloalkyl, hetaryl, phenyl and phenoxy, wherein the last three mentioned radicals may be unsubstituted or may carry 1, 2, 3, 4 or 5 radicals selected from halogen, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylsulfonyl and C$_1$-C$_4$-haloalkylsulfonyl, and R$^y$ is halogen, cyano, nitro, C$_1$-C$_4$-alkyl, C$_1$-C$_4$-haloalkyl, C$_1$-C$_4$-alkoxy or C$_1$-C$_4$-haloalkoxy.

A preferred embodiment of the invention relates to compounds of the formula I, to their salts, to their N-oxides and to the methods and uses of such compounds, wherein A is a radical of the formula A1, X$^1$ is O, X$^3$ is a lone pair and the variables R$^1$, R$^2$ and R$^3$ are as defined above and in particular have one of the preferred meanings.

A further preferred embodiment of the invention relates to compounds of the formula I, to their salts, to their N-oxides and to the methods and uses of such compounds, wherein A is a radical of the formula A1, X$^1$ is S, X$^3$ is a lone pair and the variables R$^1$, R$^2$ and R$^3$ are as defined above and in particular have one of the preferred meanings.

A further preferred embodiment of the invention relates to compounds of the formula I, to their salts, to their N-oxides and to the methods and uses of such compounds, wherein A is a radical of the formula A1, X$^1$ is N—R$^{1a}$, X$^3$ is a lone pair and the variables R$^1$, R$^2$, R$^3$ and R$^{1a}$ are as defined above and in particular have one of the preferred meanings.

A very preferred embodiment of the invention relates to compounds of the formula I and to their salts or N-oxides, wherein X$^1$ is O, X$^3$ is a lone pair and A is a radical A1. These compounds are hereinafter also referred to as compounds I.a.

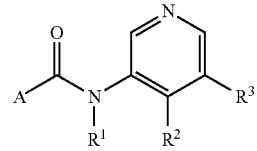

(I.a)

In formula I.a, the variables R$^1$, R$^2$ and R$^3$ are as defined herein. Amongst the compounds of the formula I.a, preference is given to those compounds, wherein at least one of the radicals R$^1$, R$^2$ and R$^3$, preferably at least two of the radicals R$^1$, R$^2$ and R$^3$, and more preferably all of the radicals R$^1$, R$^2$ and R$^3$ have one of the preferred meanings.

Amongst the compounds of the formula I.a, preference is given to those compounds, wherein A is a radical A1 with Z=O, e.g. a radical, selected from the furan radicals A1.Oa1 to A1.Oa420, A1.Ob1 to A1.Ob420 and A1.Oc1 to A1.Oc420.

Amongst the compounds of the formula I.a, preference is further given to those compounds, wherein A is a radical A1 with Z=S, e.g. a radical, selected from the thiophen radicals A1.Sa1 to A1.Sa420, A1.Sb1 to A1.Sb420 and A1.Sc1 to A1.Sc420.

Amongst the compounds of the formula I.a, preference is further given to those compounds, wherein A is a radical A1 with Z=N—R$^N$, e.g. a radical, selected from the pyrrol radicals A1.1Na1-A1.1Na420 to A1.126Na1-A1.126Na420, A1.1Nb1-A1.1Nb420 to A1.126Nb1-A1.126Nb420 and A1.1Nc1-A1.1Nc420 to A1.126Nc1-A1.126Nc420.

A particular preferred embodiment relates to compounds of the formula I.a and to their salts, wherein A is a radical A1 with Z being 0, as defined herein, in particular a radical A1, wherein (R$^A$)$_n$ have the preferred meanings, in particular a furan radical of one of the formulae A1.Oa1-A1.Oa420 to A1.Oc1-A1.Oc420;

R$^1$ is hydrogen, C$_1$-C$_4$-alkyl, C$_1$-C$_3$-alkylen-O—C$_1$-C$_3$-alkyl or C$_1$-C$_4$-alkylene-CN, most preferably hydrogen, methyl, ethyl, methoxymethyl or ethoxymethyl;

R² is selected from hydrogen, fluorine, chlorine, bromine, methyl, difluoromethyl, trifluoromethyl, methoxy, difluoromethoxy or trifluoromethoxy, in particular hydrogen; and R³ is selected from hydrogen, fluorine, chlorine, bromine, methyl, difluoromethyl, trifluoromethyl, methoxy, difluoromethoxy and trifluoromethoxy, in particular hydrogen; and wherein preferably one or in particular both radicals R² and R³ are hydrogen.

Examples of compounds of this particularly preferred embodiment are the compounds given in the following tables 1 to 9.

Table 1: Compounds of the formula I.a and their salts, wherein R¹, R² and R³ are hydrogen and wherein A is selected from the radicals A1.Oa1 to A1.Oa420.

Table 2: Compounds of the formula I.a and their salts, wherein R¹, R² and R³ are hydrogen and wherein A is selected from the radicals A1.Ob1 to A1.Ob420.

Table 3: Compounds of the formula I.a and their salts, wherein R¹, R² and R³ are hydrogen and wherein A is selected from the radicals A1.Oc1 to A1.Oc420.

Table 4: Compounds of the formula I.a and their salts, wherein R¹ is methyl, R² and R³ are hydrogen and wherein A is selected from the radicals A1.Oa1 to A1.Oa420.

Table 5: Compounds of the formula I.a and their salts, wherein R¹ is methyl, R² and R³ are hydrogen and wherein A is selected from the radicals A1.Ob1 to A1.Ob420.

Table 6: Compounds of the formula I.a and their salts, wherein R¹ is methyl, R² and R³ are hydrogen and wherein A is selected from the radicals A1.Oc1 to A1.Oc420.

Table 7: Compounds of the formula I.a and their salts, wherein R¹ is ethyl, R² and R³ are hydrogen and wherein A is selected from the radicals A1.Oa1 to A1.Oa420.

Table 8: Compounds of the formula I.a and their salts, wherein R¹ is ethyl, R² and R³ are hydrogen and wherein A is selected from the radicals A1.Ob1 to A1.Ob420.

Table 9: Compounds of the formula I.a and their salts, wherein R¹ is ethyl, R² and R³ are hydrogen and wherein A is selected from the radicals A1.Oc1 to A1.Oc420.

Another particular preferred embodiment relates to compounds of the formula I.a and to their salts, wherein A is a radical A1 with Z being S, as defined herein, in particular a radical A1, wherein $(R^4)_n$ have the preferred meanings, in particular a thiophene radical of the formulae A1.Sa1-A1.Sa420 to A1.Sc1-A1.Sc420;

R¹ is hydrogen, $C_1$-$C_4$-alkyl, $C_1$-$C_3$-alkylen-O—$C_1$-$C_3$-alkyl or $C_1$-$C_4$-alkylene-CN, most preferably hydrogen, methyl, ethyl, methoxymethyl or ethoxymethyl;

R² is selected from hydrogen, fluorine, chlorine, bromine, methyl, difluoromethyl, trifluoromethyl, methoxy, difluoromethoxy or trifluoromethoxy, in particular hydrogen; and R³ is selected from hydrogen, fluorine, chlorine, bromine, methyl, difluoromethyl, trifluoromethyl, methoxy, difluoromethoxy and trifluoromethoxy, in particular hydrogen; and wherein preferably one or in particular both radicals R² and R³ are hydrogen.

Examples of compounds of this particularly preferred embodiment are the compounds given in the following tables 10 to 18.

Table 10: Compounds of the formula I.a and their salts, wherein R¹, R² and R³ are hydrogen and wherein A is selected from the radicals A1.Sa1 to A1.Sa420.

Table 11: Compounds of the formula I.a and their salts, wherein R¹, R² and R³ are hydrogen and wherein A is selected from the radicals A1.Sb1 to A1.Sb420.

Table 12: Compounds of the formula I.a and their salts, wherein R¹, R² and R³ are hydrogen and wherein A is selected from the radicals A1.Sc1 to A1.Sc420.

Table 13: Compounds of the formula I.a and their salts, wherein R¹ is methyl, R² and R³ are hydrogen and wherein A is selected from the radicals A1.Sa1 to A1.Sa420.

Table 14: Compounds of the formula I.a and their salts, wherein R¹ is methyl, R² and R³ are hydrogen and wherein A is selected from the radicals A1.Sb1 to A1.Sb420.

Table 15: Compounds of the formula I.a and their salts, wherein R¹ is methyl, R² and R³ are hydrogen and wherein A is selected from the radicals A1.Sc1 to A1.Sc420.

Table 16: Compounds of the formula I.a and their salts, wherein R¹ is ethyl, R² and R³ are hydrogen and wherein A is selected from the radicals A1.Sa1 to A1.Sa420.

Table 17: Compounds of the formula I.a and their salts, wherein R¹ is ethyl, R² and R³ are hydrogen and wherein A is selected from the radicals A1.Sb1 to A1.Sb420.

Table 18: Compounds of the formula I.a and their salts, wherein R¹ is ethyl, R² and R³ are hydrogen and wherein A is selected from the radicals A1.Sc1 to A1.Sc420.

Another particular preferred embodiment relates to compounds of the formula I.a and to the salts and N-oxides thereof, wherein A is a radical A1 with Z being N—$R^N$, as defined herein, in particular a radical A1, wherein $(R^4)_n$ and $R^N$ have the preferred meanings and wherein $R^N$ is in particular selected from the group consisting of hydrogen, methyl, ethyl, isobutyl, cyclopropylmethyl, 2,2,2-trifluoroethyl, methoxymethyl, ethoxymethyl, 2-metoxyethyl or cyanomethyl, in particular an pyrrole radical of the formulae A1.1Na1 to A1.126Na420, A1.1Nb1 to A1.126Nb420 or A1.1Nc1 to A1.126Nc420, and more preferred a radical selected from the group consisting of those radicals A1.1Na1 to A1.126Na420, A1.1Nb1 to A1.126Nb420 or A1.1Nc1 to A1.126Nc420 wherein $R^N$ is selected from the group consisting of hydrogen, methyl, ethyl, isobutyl, cyclopropylmethyl, 2,2,2-trifluoroethyl, methoxymethyl, ethoxymethyl, 2-metoxyethyl or cyanomethyl;

R¹ is hydrogen, $C_1$-$C_4$-alkyl, $C_1$-$C_4$-haloalkyl, $C_1$-$C_3$-alkylen-O—$C_1$-$C_3$-alkyl or $C_1$-$C_4$-alkylene-CN, most preferably hydrogen, methyl, ethyl, methoxymethyl or ethoxymethyl;

R² is selected from hydrogen, fluorine, chlorine, bromine, methyl, difluoromethyl, trifluoromethyl, methoxy, difluoromethoxy or trifluoromethoxy, in particular hydrogen; and R³ is selected from hydrogen, fluorine, chlorine, bromine, methyl, difluoromethyl, trifluoromethyl, methoxy, difluoromethoxy and trifluoromethoxy, in particular hydrogen; and wherein preferably one or in particular both radicals R² and R³ are hydrogen.

Examples of compounds of this particularly preferred embodiment are the compounds given in the following tables 19 to 108

Table 19: Compounds of the formula I.a and their salts, wherein R¹, R² and R³ are hydrogen and wherein A is selected from the radicals A1.1Na1 to A1.1Na420.

Table 20: Compounds of the formula I.a and their salts, wherein R¹, R² and R³ are hydrogen and wherein A is selected from the radicals A1.1Nb1 to A1.1Nb420.

Table 21: Compounds of the formula I.a and their salts, wherein R¹, R² and R³ are hydrogen and wherein A is selected from the radicals A1.1Nc1 to A1.1Nc420.

Table 22: Compounds of the formula I.a and their salts, wherein R¹ is methyl, R² and R³ are hydrogen and wherein A is selected from the radicals A1.1Na1 to A1.1Na420.

Table 23: Compounds of the formula I.a and their salts, wherein $R^1$ is methyl, $R^2$ and $R^3$ are hydrogen and wherein A is selected from the radicals A1.1Nb1 to A1.1Nb420.

Table 24: Compounds of the formula I.a and their salts, wherein $R^1$ is methyl, $R^2$ and $R^3$ are hydrogen and wherein A is selected from the radicals A1.1Nc1 to A1.1Nc420.

Table 25: Compounds of the formula I.a and their salts, wherein $R^1$ is ethyl, $R^2$ and $R^3$ are hydrogen and wherein A is selected from the radicals A1.1Na1 to A1.1Na420.

Table 26: Compounds of the formula I.a and their salts, wherein $R^1$ is ethyl, $R^2$ and $R^3$ are hydrogen and wherein A is selected from the radicals A1.1Nb1 to A1.1Nb420.

Table 27: Compounds of the formula I.a and their salts, wherein $R^1$ is ethyl, $R^2$ and $R^3$ are hydrogen and wherein A is selected from the radicals A1.1Nc1 to A1.1Nc420.

Table 28: Compounds of the formula I.a and their salts, wherein $R^1$, $R^2$ and $R^3$ are hydrogen and wherein A is selected from the radicals A1.2Na1 to A1.2Na420.

Table 29: Compounds of the formula I.a and their salts, wherein $R^1$, $R^2$ and $R^3$ are hydrogen and wherein A is selected from the radicals A1.2Nb1 to A1.2Nb420.

Table 30: Compounds of the formula I.a and their salts, wherein $R^1$, $R^2$ and $R^3$ are hydrogen and wherein A is selected from the radicals A1.2Nc1 to A1.2Nc420.

Table 31: Compounds of the formula I.a and their salts, wherein $R^1$ is methyl, $R^2$ and $R^3$ are hydrogen and wherein A is selected from the radicals A1.2Na1 to A1.2Na420.

Table 32: Compounds of the formula I.a and their salts, wherein $R^1$ is methyl, $R^2$ and $R^3$ are hydrogen and wherein A is selected from the radicals A1.2Nb1 to A1.2Nb420.

Table 33: Compounds of the formula I.a and their salts, wherein $R^1$ is methyl, $R^2$ and $R^3$ are hydrogen and wherein A is selected from the radicals A1.2Nc1 to A1.2Nc420.

Table 34: Compounds of the formula I.a and their salts, wherein $R^1$ is ethyl, $R^2$ and $R^3$ are hydrogen and wherein A is selected from the radicals A1.2Na1 to A1.2Na420.

Table 35: Compounds of the formula I.a and their salts, wherein $R^1$ is ethyl, $R^2$ and $R^3$ are hydrogen and wherein A is selected from the radicals A1.2Nb1 to A1.2Nb420.

Table 36: Compounds of the formula I.a and their salts, wherein $R^1$ is ethyl, $R^2$ and $R^3$ are hydrogen and wherein A is selected from the radicals A1.2Nc1 to A1.2Nc420.

Table 37: Compounds of the formula I.a and their salts, wherein $R^1$, $R^2$ and $R^3$ are hydrogen and wherein A is selected from the radicals A1.3Na1 to A1.3Na420.

Table 38: Compounds of the formula I.a and their salts, wherein $R^1$, $R^2$ and $R^3$ are hydrogen and wherein A is selected from the radicals A1.3Nb1 to A1.3Nb420.

Table 39: Compounds of the formula I.a and their salts, wherein $R^1$, $R^2$ and $R^3$ are hydrogen and wherein A is selected from the radicals A1.3Nc1 to A1.3Nc420.

Table 40: Compounds of the formula I.a and their salts, wherein $R^1$ is methyl, $R^2$ and $R^3$ are hydrogen and wherein A is selected from the radicals A1.3Na1 to A1.3Na420.

Table 41: Compounds of the formula I.a and their salts, wherein $R^1$ is methyl, $R^2$ and $R^3$ are hydrogen and wherein A is selected from the radicals A1.3Nb1 to A1.3Nb420.

Table 42: Compounds of the formula I.a and their salts, wherein $R^1$ is methyl, $R^2$ and $R^3$ are hydrogen and wherein A is selected from the radicals A1.3Nc1 to A1.3Nc420.

Table 43: Compounds of the formula I.a and their salts, wherein $R^1$ is ethyl, $R^2$ and $R^3$ are hydrogen and wherein A is selected from the radicals A1.3Na1 to A1.3Na420.

Table 44: Compounds of the formula I.a and their salts, wherein $R^1$ is ethyl, $R^2$ and $R^3$ are hydrogen and wherein A is selected from the radicals A1.3Nb1 to A1.3Nb420.

Table 45: Compounds of the formula I.a and their salts, wherein $R^1$ is ethyl, $R^2$ and $R^3$ are hydrogen and wherein A is selected from the radicals A1.3Nc1 to A1.3Nc420.

Table 46: Compounds of the formula I.a and their salts, wherein $R^1$, $R^2$ and $R^3$ are hydrogen and wherein A is selected from the radicals A1.6Na1 to A1.6Na420.

Table 47: Compounds of the formula I.a and their salts, wherein $R^1$, $R^2$ and $R^3$ are hydrogen and wherein A is selected from the radicals A1.6Nb1 to A1.6Nb420.

Table 48: Compounds of the formula I.a and their salts, wherein $R^1$, $R^2$ and $R^3$ are hydrogen and wherein A is selected from the radicals A1.6Nc1 to A1.6Nc420.

Table 49: Compounds of the formula I.a and their salts, wherein $R^1$ is methyl, $R^2$ and $R^3$ are hydrogen and wherein A is selected from the radicals A1.6Na1 to A1.6Na420.

Table 50: Compounds of the formula I.a and their salts, wherein $R^1$ is methyl, $R^2$ and $R^3$ are hydrogen and wherein A is selected from the radicals A1.6Nb1 to A1.6Nb420.

Table 51: Compounds of the formula I.a and their salts, wherein $R^1$ is methyl, $R^2$ and $R^3$ are hydrogen and wherein A is selected from the radicals A1.6Nc1 to A1.6Nc420.

Table 52: Compounds of the formula I.a and their salts, wherein $R^1$ is ethyl, $R^2$ and $R^3$ are hydrogen and wherein A is selected from the radicals A1.6Na1 to A1.6Na420.

Table 53: Compounds of the formula I.a and their salts, wherein $R^1$ is ethyl, $R^2$ and $R^3$ are hydrogen and wherein A is selected from the radicals A1.6Nb1 to A1.6Nb420.

Table 54: Compounds of the formula I.a and their salts, wherein $R^1$ is ethyl, $R^2$ and $R^3$ are hydrogen and wherein A is selected from the radicals A1.6Nc1 to A1.6Nc420.

Table 55: Compounds of the formula I.a and their salts, wherein $R^1$, $R^2$ and $R^3$ are hydrogen and wherein A is selected from the radicals A1.82Na1 to A1.82Na420.

Table 56: Compounds of the formula I.a and their salts, wherein $R^1$, $R^2$ and $R^3$ are hydrogen and wherein A is selected from the radicals A1.82Nb1 to A1.82Nb420.

Table 57: Compounds of the formula I.a and their salts, wherein $R^1$, $R^2$ and $R^3$ are hydrogen and wherein A is selected from the radicals A1.82Nc1 to A1.82Nc420.

Table 58: Compounds of the formula I.a and their salts, wherein $R^1$ is methyl, $R^2$ and $R^3$ are hydrogen and wherein A is selected from the radicals A1.82Na1 to A1.82Na420.

Table 59: Compounds of the formula I.a and their salts, wherein $R^1$ is methyl, $R^2$ and $R^3$ are hydrogen and wherein A is selected from the radicals A1.82Nb1 to A1.82Nb420.

Table 60: Compounds of the formula I.a and their salts, wherein $R^1$ is methyl, $R^2$ and $R^3$ are hydrogen and wherein A is selected from the radicals A1.82Nc1 to A1.82Nc420.

Table 61: Compounds of the formula I.a and their salts, wherein $R^1$ is ethyl, $R^2$ and $R^3$ are hydrogen and wherein A is selected from the radicals A1.82Na1 to A1.82Na420.

Table 62: Compounds of the formula I.a and their salts, wherein $R^1$ is ethyl, $R^2$ and $R^3$ are hydrogen and wherein A is selected from the radicals A1.82Nb1 to A1.82Nb420.

Table 63: Compounds of the formula I.a and their salts, wherein $R^1$ is ethyl, $R^2$ and $R^3$ are hydrogen and wherein A is selected from the radicals A1.82Nc1 to A1.82Nc420.

Table 64: Compounds of the formula I.a and their salts, wherein $R^1$, $R^2$ and $R^3$ are hydrogen and wherein A is selected from the radicals A1.83Na1 to A1.83Na420.

Table 65: Compounds of the formula I.a and their salts, wherein $R^1$, $R^2$ and $R^3$ are hydrogen and wherein A is selected from the radicals A1.83Nb1 to A1.83Nb420.

Table 66: Compounds of the formula I.a and their salts, wherein $R^1$, $R^2$ and $R^3$ are hydrogen and wherein A is selected from the radicals A1.83Nc1 to A1.83Nc420.

Table 67: Compounds of the formula I.a and their salts, wherein $R^1$ is methyl, $R^2$ and $R^3$ are hydrogen and wherein A is selected from the radicals A1.83Na1 to A1.83Na420.
Table 68: Compounds of the formula I.a and their salts, wherein $R^1$ is methyl, $R^2$ and $R^3$ are hydrogen and wherein A is selected from the radicals A1.83Nb1 to A1.83Nb420.
Table 69: Compounds of the formula I.a and their salts, wherein $R^1$ is methyl, $R^2$ and $R^3$ are hydrogen and wherein A is selected from the radicals A1.83Nc1 to A1.83Nc420.
Table 70: Compounds of the formula I.a and their salts, wherein $R^1$ is ethyl, $R^2$ and $R^3$ are hydrogen and wherein A is selected from the radicals A1.83Na1 to A1.83Na420.
Table 71: Compounds of the formula I.a and their salts, wherein $R^1$ is ethyl, $R^2$ and $R^3$ are hydrogen and wherein A is selected from the radicals A1.83Nb1 to A1.83Nb420.
Table 72: Compounds of the formula I.a and their salts, wherein $R^1$ is ethyl, $R^2$ and $R^3$ are hydrogen and wherein A is selected from the radicals A1.83Nc1 to A1.83Nc420.
Table 73: Compounds of the formula I.a and their salts, wherein $R^1$, $R^2$ and $R^3$ are hydrogen and wherein A is selected from the radicals A1.84Na1 to A1.84Na420.
Table 74: Compounds of the formula I.a and their salts, wherein $R^1$, $R^2$ and $R^3$ are hydrogen and wherein A is selected from the radicals A1.84Nb1 to A1.84Nb420.
Table 75: Compounds of the formula I.a and their salts, wherein $R^1$, $R^2$ and $R^3$ are hydrogen and wherein A is selected from the radicals A1.84Nc1 to A1.84Nc420.
Table 76: Compounds of the formula I.a and their salts, wherein $R^1$ is methyl, $R^2$ and $R^3$ are hydrogen and wherein A is selected from the radicals A1.84Na1 to A1.84Na420.
Table 77: Compounds of the formula I.a and their salts, wherein $R^1$ is methyl, $R^2$ and $R^3$ are hydrogen and wherein A is selected from the radicals A1.84Nb1 to A1.84Nb420.
Table 78: Compounds of the formula I.a and their salts, wherein $R^1$ is methyl, $R^2$ and $R^3$ are hydrogen and wherein A is selected from the radicals A1.84Nc1 to A1.84Nc420.
Table 79: Compounds of the formula I.a and their salts, wherein $R^1$ is ethyl, $R^2$ and $R^3$ are hydrogen and wherein A is selected from the radicals A1.84Na1 to A1.84Na420.
Table 80: Compounds of the formula I.a and their salts, wherein $R^1$ is ethyl, $R^2$ and $R^3$ are hydrogen and wherein A is selected from the radicals A1.84Nb1 to A1.84Nb420.
Table 81: Compounds of the formula I.a and their salts, wherein $R^1$ is ethyl, $R^2$ and $R^3$ are hydrogen and wherein A is selected from the radicals A1.84Nc1 to A1.84Nc420.
Table 82: Compounds of the formula I.a and their salts, wherein $R^1$, $R^2$ and $R^3$ are hydrogen and wherein A is selected from the radicals A1.85Na1 to A1.85Na420.
Table 83: Compounds of the formula I.a and their salts, wherein $R^1$, $R^2$ and $R^3$ are hydrogen and wherein A is selected from the radicals A1.85Nb1 to A1.85Nb420.
Table 84: Compounds of the formula I.a and their salts, wherein $R^1$, $R^2$ and $R^3$ are hydrogen and wherein A is selected from the radicals A1.85Nc1 to A1.85Nc420.
Table 85: Compounds of the formula I.a and their salts, wherein $R^1$ is methyl, $R^2$ and $R^3$ are hydrogen and wherein A is selected from the radicals A1.85Na1 to A1.85Na420.
Table 86: Compounds of the formula I.a and their salts, wherein $R^1$ is methyl, $R^2$ and $R^3$ are hydrogen and wherein A is selected from the radicals A1.85Nb1 to A1.85Nb420.
Table 87: Compounds of the formula I.a and their salts, wherein $R^1$ is methyl, $R^2$ and $R^3$ are hydrogen and wherein A is selected from the radicals A1.85Nc1 to A1.85Nc420.
Table 88: Compounds of the formula I.a and their salts, wherein $R^1$ is ethyl, $R^2$ and $R^3$ are hydrogen and wherein A is selected from the radicals A1.85Na1 to A1.85Na420.
Table 89: Compounds of the formula I.a and their salts, wherein $R^1$ is ethyl, $R^2$ and $R^3$ are hydrogen and wherein A is selected from the radicals A1.85Nb1 to A1.85Nb420.
Table 90: Compounds of the formula I.a and their salts, wherein $R^1$ is ethyl, $R^2$ and $R^3$ are hydrogen and wherein A is selected from the radicals A1.85Nc1 to A1.85Nc420.
Table 91: Compounds of the formula I.a and their salts, wherein $R^1$, $R^2$ and $R^3$ are hydrogen and wherein A is selected from the radicals A1.87Na1 to A1.87Na420.
Table 92: Compounds of the formula I.a and their salts, wherein $R^1$, $R^2$ and $R^3$ are hydrogen and wherein A is selected from the radicals A1.87Nb1 to A1.87Nb420.
Table 93: Compounds of the formula I.a and their salts, wherein $R^1$, $R^2$ and $R^3$ are hydrogen and wherein A is selected from the radicals A1.87Nc1 to A1.87Nc420.
Table 94: Compounds of the formula I.a and their salts, wherein $R^1$ is methyl, $R^2$ and $R^3$ are hydrogen and wherein A is selected from the radicals A1.87Na1 to A1.87Na420.
Table 95: Compounds of the formula I.a and their salts, wherein $R^1$ is methyl, $R^2$ and $R^3$ are hydrogen and wherein A is selected from the radicals A1.87Nb1 to A1.87Nb420.
Table 96: Compounds of the formula I.a and their salts, wherein $R^1$ is methyl, $R^2$ and $R^3$ are hydrogen and wherein A is selected from the radicals A1.87Nc1 to A1.87Nc420.
Table 97: Compounds of the formula I.a and their salts, wherein $R^1$ is ethyl, $R^2$ and $R^3$ are hydrogen and wherein A is selected from the radicals A1.87Na1 to A1.87Na420.
Table 98: Compounds of the formula I.a and their salts, wherein $R^1$ is ethyl, $R^2$ and $R^3$ are hydrogen and wherein A is selected from the radicals A1.87Nb1 to A1.87Nb420.
Table 99: Compounds of the formula I.a and their salts, wherein $R^1$ is ethyl, $R^2$ and $R^3$ are hydrogen and wherein A is selected from the radicals A1.87Nc1 to A1.87Nc420
Table 100: Compounds of the formula I.a and their salts, wherein $R^1$, $R^2$ and $R^3$ are hydrogen and wherein A is selected from the radicals A1.94Na1 to A1.94Na420.
Table 101: Compounds of the formula I.a and their salts, wherein $R^1$, $R^2$ and $R^3$ are hydrogen and wherein A is selected from the radicals A1.94Nb1 to A1.94Nb420.
Table 102: Compounds of the formula I.a and their salts, wherein $R^1$, $R^2$ and $R^3$ are hydrogen and wherein A is selected from the radicals A1.94Nc1 to A1.94Nc420.
Table 103: Compounds of the formula I.a and their salts, wherein $R^1$ is methyl, $R^2$ and $R^3$ are hydrogen and wherein A is selected from the radicals A1.94Na1 to A1.94Na420.
Table 104: Compounds of the formula I.a and their salts, wherein $R^1$ is methyl, $R^2$ and $R^3$ are hydrogen and wherein A is selected from the radicals A1.94Nb1 to A1.94Nb420.
Table 105: Compounds of the formula I.a and their salts, wherein $R^1$ is methyl, $R^2$ and $R^3$ are hydrogen and wherein A is selected from the radicals A1.94Nc1 to A1.94Nc420.
Table 106: Compounds of the formula I.a and their salts, wherein $R^1$ is ethyl, $R^2$ and $R^3$ are hydrogen and wherein A is selected from the radicals A1.94Na1 to A1.94Na420.
Table 107: Compounds of the formula I.a and their salts, wherein $R^1$ is ethyl, $R^2$ and $R^3$ are hydrogen and wherein A is selected from the radicals A1.87Nb1 to A1.94Nb420.
Table 108: Compounds of the formula I.a and their salts, wherein $R^1$ is ethyl, $R^2$ and $R^3$ are hydrogen and wherein A is selected from the radicals A1.94Nc1 to A1.94Nc420.

Another particular preferred embodiment relates to compounds of the formula I.a and to their salts, wherein A is a radical A2 with Z being O, as defined herein, in particular a radical A2, wherein $(R^4)_n$ have the preferred meanings, in particular a furan radical of the formulae A2.Oa1-A2.Oa420 to A2.Oc1-A2.Oc420;

$R^1$ is hydrogen, $C_1$-$C_4$-alkyl, $C_1$-$C_4$-haloalkyl, $C_1$-$C_3$-alkylen-O—$C_1$-$C_3$-alkyl or $C_1$-$C_4$-alkylene-CN, most preferably hydrogen, methyl, ethyl, methoxymethyl or ethoxymethyl;

$R^2$ is selected from hydrogen, fluorine, chlorine, bromine, methyl, difluoromethyl, trifluoromethyl, methoxy, difluoromethoxy or trifluoromethoxy, in particular hydrogen; and $R^3$ is selected from hydrogen, fluorine, chlorine, bromine, methyl, difluoromethyl, trifluoromethyl, methoxy, difluoromethoxy and trifluoromethoxy, in particular hydrogen; and wherein preferably one or in particular both radicals $R^2$ and $R^3$ are hydrogen.

Examples of compounds of this particularly preferred embodiment are the compounds given in the following tables 109 to 117.

Table 109: Compounds of the formula I.a and their salts, wherein $R^1$, $R^2$ and $R^3$ are hydrogen and wherein A is selected from the radicals A2.Oa1 to A2.Oa420.

Table 110: Compounds of the formula I.a and their salts, wherein $R^1$, $R^2$ and $R^3$ are hydrogen and wherein A is selected from the radicals A2.Ob1 to A2.Ob420.

Table 111: Compounds of the formula I.a and their salts, wherein $R^1$, $R^2$ and $R^3$ are hydrogen and wherein A is selected from the radicals A2.Oc1 to A2.Oc420.

Table 112: Compounds of the formula I.a and their salts, wherein $R^1$ is methyl, $R^2$ and $R^3$ are hydrogen and wherein A is selected from the radicals A2.Oa1 to A2.Oa420.

Table 113: Compounds of the formula I.a and their salts, wherein $R^1$ is methyl, $R^2$ and $R^3$ are hydrogen and wherein A is selected from the radicals A2.Ob1 to A2. Ob420.

Table 114: Compounds of the formula I.a and their salts, wherein $R^1$ is methyl, $R^2$ and $R^3$ are hydrogen and wherein A is selected from the radicals A2.Oc1 to A2.Oc420.

Table 115: Compounds of the formula I.a and their salts, wherein $R^1$ is ethyl, $R^2$ and $R^3$ are hydrogen and wherein A is selected from the radicals A2.Oa1 to A2.Oa420.

Table 116: Compounds of the formula I.a and their salts, wherein $R^1$ is ethyl, $R^2$ and $R^3$ are hydrogen and wherein A is selected from the radicals A2.Ob1 to A2.Ob420.

Table 117: Compounds of the formula I.a and their salts, wherein $R^1$ is ethyl, $R^2$ and $R^3$ are hydrogen and wherein A is selected from the radicals A2.Oc1 to A2.Oc420.

Another particular preferred embodiment relates to compounds of the formula I.a and to their salts, wherein A is a radical A2 with Z being S, as defined herein, in particular a radical A2, wherein $(R^A)_n$ have the preferred meanings, in particular a thiophene radical of the formulae A2.Sa1-A2.Sa420 to A2.Sc1-A2.Sc420;

$R^1$ is hydrogen, $C_1$-$C_4$-alkyl, $C_1$-$C_4$-haloalkyl, $C_1$-$C_3$-alkylen-O—$C_1$-$C_3$-alkyl or $C_1$-$C_4$-alkylene-CN, most preferably hydrogen, methyl, ethyl, methoxymethyl or ethoxymethyl;

$R^2$ is selected from hydrogen, fluorine, chlorine, bromine, methyl, difluoromethyl, trifluoromethyl, methoxy, difluoromethoxy or trifluoromethoxy, in particular hydrogen; and $R^3$ is selected from hydrogen, fluorine, chlorine, bromine, methyl, difluoromethyl, trifluoromethyl, methoxy, difluoromethoxy and trifluoromethoxy, in particular hydrogen; and wherein preferably one or in particular both radicals $R^2$ and $R^3$ are hydrogen.

Examples of compounds of this particularly preferred embodiment are the compounds given in the following tables 118 to 126.

Table 118: Compounds of the formula I.a and their salts, wherein $R^1$, $R^2$ and $R^3$ are hydrogen and wherein A is selected from the radicals A2.Sa1 to A2.Sa420.

Table 119: Compounds of the formula I.a and their salts, wherein $R^1$, $R^2$ and $R^3$ are hydrogen and wherein A is selected from the radicals A2.Sb1 to A2.Sb420.

Table 120: Compounds of the formula I.a and their salts, wherein $R^1$, $R^2$ and $R^3$ are hydrogen and wherein A is selected from the radicals A2.Sc1 to A2.Sc420.

Table 121: Compounds of the formula I.a and their salts, wherein $R^1$ is methyl, $R^2$ and $R^3$ are hydrogen and wherein A is selected from the radicals A2.Sa1 to A2.Sa420.

Table 122: Compounds of the formula I.a and their salts, wherein $R^1$ is methyl, $R^2$ and $R^3$ are hydrogen and wherein A is selected from the radicals A2.Sb1 to A2.Sb420.

Table 123: Compounds of the formula I.a and their salts, wherein $R^1$ is methyl, $R^2$ and $R^3$ are hydrogen and wherein A is selected from the radicals A2.Sc1 to A2.Sc420.

Table 124: Compounds of the formula I.a and their salts, wherein $R^1$ is ethyl, $R^2$ and $R^3$ are hydrogen and wherein A is selected from the radicals A2.Sa1 to A2.Sa420.

Table 125: Compounds of the formula I.a and their salts, wherein $R^1$ is ethyl, $R^2$ and $R^3$ are hydrogen and wherein A is selected from the radicals A2.Sb1 to A2.Sb420.

Table 126: Compounds of the formula I.a and their salts, wherein $R^1$ is ethyl, $R^2$ and $R^3$ are hydrogen and wherein A is selected from the radicals A1.Sc1 to A1.Sc420.

Another particular preferred embodiment relates to compounds of the formula I.a and to the salts and N-oxides thereof, wherein A is a radical A2 with Z being N—$R^N$, as defined herein, in particular a radical A2, wherein $(R^A)_n$ and $R^N$ have the preferred meanings and wherein $R^N$ is in particular selected from the group consisting of hydrogen, methyl, ethyl, isobutyl, cyclopropylmethyl, 2,2,2-trifluoroethyl, methoxymethyl, ethoxymethyl, 2-metoxyethyl or cyanomethyl, in particular an pyrrole radical of the formulae A2.1Na1 to A21.126Na420, A2.1 Nb1 to A2.126Nb420 or A2.1Nc1 to A2.126Nc420, and more preferred a radical selected from the group consisting of those radicals A2.1Na1 to A2.126Na420, A2.1 Nb1 to A2.126Nb420 or A2.1Nc1 to A2.126Nc420 wherein $R^N$ is selected from the group consisting of hydrogen, methyl, ethyl, isobutyl, cyclopropylmethyl, 2,2,2-trifluoroethyl, methoxymethyl, ethoxymethyl, 2-metoxyethyl or cyanomethyl;

$R^1$ is hydrogen, $C_1$-$C_4$-alkyl, $C_1$-$C_4$-haloalkyl, $C_1$-$C_3$-alkylen-O—$C_1$-$C_3$-alkyl or $C_1$-$C_4$-alkylene-CN, most preferably hydrogen, methyl, ethyl, methoxymethyl or ethoxymethyl;

$R^2$ is selected from hydrogen, fluorine, chlorine, bromine, methyl, difluoromethyl, trifluoromethyl, methoxy, difluoromethoxy or trifluoromethoxy, in particular hydrogen; and $R^3$ is selected from hydrogen, fluorine, chlorine, bromine, methyl, difluoromethyl, trifluoromethyl, methoxy, difluoromethoxy and trifluoromethoxy, in particular hydrogen; and wherein preferably one or in particular both radicals $R^2$ and $R^3$ are hydrogen.

Examples of compounds of this particularly preferred embodiment are the compounds given in the following tables 127 to 216:

Table 127: Compounds of the formula I.a and their salts, wherein $R^1$, $R^2$ and $R^3$ are hydrogen and wherein A is selected from the radicals A2.1Na1 to A2.1Na420.

Table 128: Compounds of the formula I.a and their salts, wherein $R^1$, $R^2$ and $R^3$ are hydrogen and wherein A is selected from the radicals A2.1Nb1 to A2.1Nb420.

Table 129: Compounds of the formula I.a and their salts, wherein $R^1$, $R^2$ and $R^3$ are hydrogen and wherein A is selected from the radicals A2.1Nc1 to A2.1Nc420.

Table 130: Compounds of the formula I.a and their salts, wherein $R^1$ is methyl, $R^2$ and $R^3$ are hydrogen and wherein A is selected from the radicals A2.1Na1 to A2.1Na420.

Table 131: Compounds of the formula I.a and their salts, wherein $R^1$ is methyl, $R^2$ and $R^3$ are hydrogen and wherein A is selected from the radicals A2.1Nb1 to A2.1Nb420.

Table 132: Compounds of the formula I.a and their salts, wherein $R^1$ is methyl, $R^2$ and $R^3$ are hydrogen and wherein A is selected from the radicals A2.1Nc1 to A2.1Nc420.

Table 133: Compounds of the formula I.a and their salts, wherein $R^1$ is ethyl, $R^2$ and $R^3$ are hydrogen and wherein A is selected from the radicals A2.1Na1 to A2.1Na420.

Table 134: Compounds of the formula I.a and their salts, wherein $R^1$ is ethyl, $R^2$ and $R^3$ are hydrogen and wherein A is selected from the radicals A2.1Nb1 to A2.1Nb420.

Table 135: Compounds of the formula I.a and their salts, wherein $R^1$ is ethyl, $R^2$ and $R^3$ are hydrogen and wherein A is selected from the radicals A2.1Nc1 to A2.1Nc420.

Table 136: Compounds of the formula I.a and their salts, wherein $R^1$, $R^2$ and $R^3$ are hydrogen and wherein A is selected from the radicals A2.2Na1 to A2.2Na420.

Table 137: Compounds of the formula I.a and their salts, wherein $R^1$, $R^2$ and $R^3$ are hydrogen and wherein A is selected from the radicals A2.2Nb1 to A2.2Nb420.

Table 138: Compounds of the formula I.a and their salts, wherein $R^1$, $R^2$ and $R^3$ are hydrogen and wherein A is selected from the radicals A2.2Nc1 to A2.2Nc420.

Table 139: Compounds of the formula I.a and their salts, wherein $R^1$ is methyl, $R^2$ and $R^3$ are hydrogen and wherein A is selected from the radicals A2.2Na1 to A2.2Na420.

Table 140: Compounds of the formula I.a and their salts, wherein $R^1$ is methyl, $R^2$ and $R^3$ are hydrogen and wherein A is selected from the radicals A2.2Nb1 to A2.2Nb420.

Table 141: Compounds of the formula I.a and their salts, wherein $R^1$ is methyl, $R^2$ and $R^3$ are hydrogen and wherein A is selected from the radicals A2.2Nc1 to A2.2Nc420.

Table 142: Compounds of the formula I.a and their salts, wherein $R^1$ is ethyl, $R^2$ and $R^3$ are hydrogen and wherein A is selected from the radicals A2.2Na1 to A2.2Na420.

Table 143: Compounds of the formula I.a and their salts, wherein $R^1$ is ethyl, $R^2$ and $R^3$ are hydrogen and wherein A is selected from the radicals A2.2Nb1 to A2.2Nb420.

Table 144: Compounds of the formula I.a and their salts, wherein $R^1$ is ethyl, $R^2$ and $R^3$ are hydrogen and wherein A is selected from the radicals A2.2Nc1 to A2.2Nc420.

Table 145: Compounds of the formula I.a and their salts, wherein $R^1$, $R^2$ and $R^3$ are hydrogen and wherein A is selected from the radicals A2.3Na1 to A2.3Na420.

Table 146: Compounds of the formula I.a and their salts, wherein $R^1$, $R^2$ and $R^3$ are hydrogen and wherein A is selected from the radicals A2.3Nb1 to A2.3Nb420.

Table 147: Compounds of the formula I.a and their salts, wherein $R^1$, $R^2$ and $R^3$ are hydrogen and wherein A is selected from the radicals A2.3Nc1 to A2.3Nc420.

Table 148: Compounds of the formula I.a and their salts, wherein $R^1$ is methyl, $R^2$ and $R^3$ are hydrogen and wherein A is selected from the radicals A2.3Na1 to A2.3Na420.

Table 149: Compounds of the formula I.a and their salts, wherein $R^1$ is methyl, $R^2$ and $R^3$ are hydrogen and wherein A is selected from the radicals A2.3Nb1 to A2.3Nb420.

Table 150: Compounds of the formula I.a and their salts, wherein $R^1$ is methyl, $R^2$ and $R^3$ are hydrogen and wherein A is selected from the radicals A2.3Nc1 to A2.3Nc420.

Table 151: Compounds of the formula I.a and their salts, wherein $R^1$ is ethyl, $R^2$ and $R^3$ are hydrogen and wherein A is selected from the radicals A2.3Na1 to A2.3Na420.

Table 152: Compounds of the formula I.a and their salts, wherein $R^1$ is ethyl, $R^2$ and $R^3$ are hydrogen and wherein A is selected from the radicals A2.3Nb1 to A2.3Nb420.

Table 153: Compounds of the formula I.a and their salts, wherein $R^1$ is ethyl, $R^2$ and $R^3$ are hydrogen and wherein A is selected from the radicals A2.3Nc1 to A2.3Nc420.

Table 154: Compounds of the formula I.a and their salts, wherein $R^1$, $R^2$ and $R^3$ are hydrogen and wherein A is selected from the radicals A2.6Na1 to A2.6Na420.

Table 155: Compounds of the formula I.a and their salts, wherein $R^1$, $R^2$ and $R^3$ are hydrogen and wherein A is selected from the radicals A2.6Nb1 to A2.6Nb420.

Table 156: Compounds of the formula I.a and their salts, wherein $R^1$, $R^2$ and $R^3$ are hydrogen and wherein A is selected from the radicals A2.6Nc1 to A2.6Nc420.

Table 157: Compounds of the formula I.a and their salts, wherein $R^1$ is methyl, $R^2$ and $R^3$ are hydrogen and wherein A is selected from the radicals A2.6Na1 to A2.6Na420.

Table 158: Compounds of the formula I.a and their salts, wherein $R^1$ is methyl, $R^2$ and $R^3$ are hydrogen and wherein A is selected from the radicals A2.6Nb1 to A2.6Nb420.

Table 159: Compounds of the formula I.a and their salts, wherein $R^1$ is methyl, $R^2$ and $R^3$ are hydrogen and wherein A is selected from the radicals A2.6Nc1 to A2.6Nc420.

Table 160: Compounds of the formula I.a and their salts, wherein $R^1$ is ethyl, $R^2$ and $R^3$ are hydrogen and wherein A is selected from the radicals A2.6Na1 to A2.6Na420.

Table 161: Compounds of the formula I.a and their salts, wherein $R^1$ is ethyl, $R^2$ and $R^3$ are hydrogen and wherein A is selected from the radicals A2.6Nb1 to A2.6Nb420.

Table 162: Compounds of the formula I.a and their salts, wherein $R^1$ is ethyl, $R^2$ and $R^3$ are hydrogen and wherein A is selected from the radicals A2.6Nc1 to A2.6Nc420.

Table 163: Compounds of the formula I.a and their salts, wherein $R^1$, $R^2$ and $R^3$ are hydrogen and wherein A is selected from the radicals A2.83Na1 to A2.83Na420.

Table 164: Compounds of the formula I.a and their salts, wherein $R^1$, $R^2$ and $R^3$ are hydrogen and wherein A is selected from the radicals A2.83Nb1 to A2.83Nb420.

Table 165: Compounds of the formula I.a and their salts, wherein $R^1$, $R^2$ and $R^3$ are hydrogen and wherein A is selected from the radicals A2.83Nc1 to A2.83Nc420.

Table 166: Compounds of the formula I.a and their salts, wherein $R^1$ is methyl, $R^2$ and $R^3$ are hydrogen and wherein A is selected from the radicals A2.83Na1 to A2.83Na420.

Table 167: Compounds of the formula I.a and their salts, wherein $R^1$ is methyl, $R^2$ and $R^3$ are hydrogen and wherein A is selected from the radicals A2.83Nb1 to A2.83Nb420.

Table 168: Compounds of the formula I.a and their salts, wherein $R^1$ is methyl, $R^2$ and $R^3$ are hydrogen and wherein A is selected from the radicals A2.83Nc1 to A2.83Nc420.

Table 169: Compounds of the formula I.a and their salts, wherein $R^1$ is ethyl, $R^2$ and $R^3$ are hydrogen and wherein A is selected from the radicals A2.83Na1 to A2.83Na420.

Table 170: Compounds of the formula I.a and their salts, wherein $R^1$ is ethyl, $R^2$ and $R^3$ are hydrogen and wherein A is selected from the radicals A2.83Nb1 to A2.83Nb420.

Table 171: Compounds of the formula I.a and their salts, wherein $R^1$ is ethyl, $R^2$ and $R^3$ are hydrogen and wherein A is selected from the radicals A2.83Nc1 to A2.83Nc420.

Table 172: Compounds of the formula I.a and their salts, wherein $R^1$, $R^2$ and $R^3$ are hydrogen and wherein A is selected from the radicals A2.82Na1 to A2.82Na420.

Table 173: Compounds of the formula I.a and their salts, wherein $R^1$, $R^2$ and $R^3$ are hydrogen and wherein A is selected from the radicals A2.82Nb1 to A2.82Nb420.

Table 174: Compounds of the formula I.a and their salts, wherein $R^1$, $R^2$ and $R^3$ are hydrogen and wherein A is selected from the radicals A2.82Nc1 to A2.82Nc420.

Table 175: Compounds of the formula I.a and their salts, wherein $R^1$ is methyl, $R^2$ and $R^3$ are hydrogen and wherein A is selected from the radicals A2.82Na1 to A2.82Na420.

Table 176: Compounds of the formula I.a and their salts, wherein $R^1$ is methyl, $R^2$ and $R^3$ are hydrogen and wherein A is selected from the radicals A2.82Nb1 to A2.82Nb420.

Table 177: Compounds of the formula I.a and their salts, wherein $R^1$ is methyl, $R^2$ and $R^3$ are hydrogen and wherein A is selected from the radicals A2.82Nc1 to A2.82Nc420.

Table 178: Compounds of the formula I.a and their salts, wherein $R^1$ is ethyl, $R^2$ and $R^3$ are hydrogen and wherein A is selected from the radicals A2.82Na1 to A2.82Na420.

Table 179: Compounds of the formula I.a and their salts, wherein $R^1$ is ethyl, $R^2$ and $R^3$ are hydrogen and wherein A is selected from the radicals A2.82Nb1 to A2.82Nb420.

Table 180: Compounds of the formula I.a and their salts, wherein $R^1$ is ethyl, $R^2$ and $R^3$ are hydrogen and wherein A is selected from the radicals A2.82Nc1 to A2.82Nc420.

Table 181: Compounds of the formula I.a and their salts, wherein $R^1$, $R^2$ and $R^3$ are hydrogen and wherein A is selected from the radicals A2.84Na1 to A2.84Na420.

Table 182: Compounds of the formula I.a and their salts, wherein $R^1$, $R^2$ and $R^3$ are hydrogen and wherein A is selected from the radicals A2.84Nb1 to A2.84Nb420.

Table 183: Compounds of the formula I.a and their salts, wherein $R^1$, $R^2$ and $R^3$ are hydrogen and wherein A is selected from the radicals A2.84Nc1 to A2.84Nc420.

Table 184: Compounds of the formula I.a and their salts, wherein $R^1$ is methyl, $R^2$ and $R^3$ are hydrogen and wherein A is selected from the radicals A2.84Na1 to A2.84Na420.

Table 185: Compounds of the formula I.a and their salts, wherein $R^1$ is methyl, $R^2$ and $R^3$ are hydrogen and wherein A is selected from the radicals A2.84Nb1 to A2.84Nb420.

Table 186: Compounds of the formula I.a and their salts, wherein $R^1$ is methyl, $R^2$ and $R^3$ are hydrogen and wherein A is selected from the radicals A2.84Nc1 to A2.84Nc420.

Table 187: Compounds of the formula I.a and their salts, wherein $R^1$ is ethyl, $R^2$ and $R^3$ are hydrogen and wherein A is selected from the radicals A2.84Na1 to A2.84Na420.

Table 188: Compounds of the formula I.a and their salts, wherein $R^1$ is ethyl, $R^2$ and $R^3$ are hydrogen and wherein A is selected from the radicals A2.84Nb1 to A2.84Nb420.

Table 189: Compounds of the formula I.a and their salts, wherein $R^1$ is ethyl, $R^2$ and $R^3$ are hydrogen and wherein A is selected from the radicals A2.84Nc1 to A2.84Nc420.

Table 190: Compounds of the formula I.a and their salts, wherein $R^1$, $R^2$ and $R^3$ are hydrogen and wherein A is selected from the radicals A2.85Na1 to A2.85Na420.

Table 191: Compounds of the formula I.a and their salts, wherein $R^1$, $R^2$ and $R^3$ are hydrogen and wherein A is selected from the radicals A2.85Nb1 to A2.85Nb420.

Table 192: Compounds of the formula I.a and their salts, wherein $R^1$, $R^2$ and $R^3$ are hydrogen and wherein A is selected from the radicals A2.85Nc1 to A2.85Nc420.

Table 193: Compounds of the formula I.a and their salts, wherein $R^1$ is methyl, $R^2$ and $R^3$ are hydrogen and wherein A is selected from the radicals A2.85Na1 to A2.85Na420.

Table 194: Compounds of the formula I.a and their salts, wherein $R^1$ is methyl, $R^2$ and $R^3$ are hydrogen and wherein A is selected from the radicals A2.85Nb1 to A2.85Nb420.

Table 195: Compounds of the formula I.a and their salts, wherein $R^1$ is methyl, $R^2$ and $R^3$ are hydrogen and wherein A is selected from the radicals A2.85Nc1 to A2.85Nc420.

Table 196: Compounds of the formula I.a and their salts, wherein $R^1$ is ethyl, $R^2$ and $R^3$ are hydrogen and wherein A is selected from the radicals A2.85Na1 to A2.85Na420.

Table 197: Compounds of the formula I.a and their salts, wherein $R^1$ is ethyl, $R^2$ and $R^3$ are hydrogen and wherein A is selected from the radicals A2.85Nb1 to A2.85Nb420.

Table 198: Compounds of the formula I.a and their salts, wherein $R^1$ is ethyl, $R^2$ and $R^3$ are hydrogen and wherein A is selected from the radicals A2.85Nc1 to A2.85Nc420.

Table 199: Compounds of the formula I.a and their salts, wherein $R^1$, $R^2$ and $R^3$ are hydrogen and wherein A is selected from the radicals A2.87Na1 to A2.87Na420.

Table 200: Compounds of the formula I.a and their salts, wherein $R^1$, $R^2$ and $R^3$ are hydrogen and wherein A is selected from the radicals A2.87Nb1 to A2.87Nb420.

Table 201: Compounds of the formula I.a and their salts, wherein $R^1$, $R^2$ and $R^3$ are hydrogen and wherein A is selected from the radicals A2.87Nc1 to A2.87Nc420.

Table 202: Compounds of the formula I.a and their salts, wherein $R^1$ is methyl, $R^2$ and $R^3$ are hydrogen and wherein A is selected from the radicals A2.87Na1 to A2.87Na420.

Table 203: Compounds of the formula I.a and their salts, wherein $R^1$ is methyl, $R^2$ and $R^3$ are hydrogen and wherein A is selected from the radicals A2.87Nb1 to A2.87Nb420.

Table 204: Compounds of the formula I.a and their salts, wherein $R^1$ is methyl, $R^2$ and $R^3$ are hydrogen and wherein A is selected from the radicals A2.87Nc1 to A2.87Nc420.

Table 205: Compounds of the formula I.a and their salts, wherein $R^1$ is ethyl, $R^2$ and $R^3$ are hydrogen and wherein A is selected from the radicals A2.87Na1 to A2.87Na420.

Table 206: Compounds of the formula I.a and their salts, wherein $R^1$ is ethyl, $R^2$ and $R^3$ are hydrogen and wherein A is selected from the radicals A2.87Nb1 to A2.87Nb420.

Table 207: Compounds of the formula I.a and their salts, wherein $R^1$ is ethyl, $R^2$ and $R^3$ are hydrogen and wherein A is selected from the radicals A2.87Nc1 to A2.87Nc420.

Table 208: Compounds of the formula I.a and their salts, wherein $R^1$, $R^2$ and $R^3$ are hydrogen and wherein A is selected from the radicals A2.94Na1 to A2.94Na420.

Table 209: Compounds of the formula I.a and their salts, wherein $R^1$, $R^2$ and $R^3$ are hydrogen and wherein A is selected from the radicals A2.94Nb1 to A2.94Nb420.

Table 210: Compounds of the formula I.a and their salts, wherein $R^1$, $R^2$ and $R^3$ are hydrogen and wherein A is selected from the radicals A2.94Nc1 to A2.94Nc420.

Table 211: Compounds of the formula I.a and their salts, wherein $R^1$ is methyl, $R^2$ and $R^3$ are hydrogen and wherein A is selected from the radicals A2.94Na1 to A2.94Na420.

Table 212: Compounds of the formula I.a and their salts, wherein $R^1$ is methyl, $R^2$ and $R^3$ are hydrogen and wherein A is selected from the radicals A2.94Nb1 to A2.94Nb420.

Table 213: Compounds of the formula I.a and their salts, wherein $R^1$ is methyl, $R^2$ and $R^3$ are hydrogen and wherein A is selected from the radicals A2.94Nc1 to A2.94Nc420.

Table 214: Compounds of the formula I.a and their salts, wherein $R^1$ is ethyl, $R^2$ and $R^3$ are hydrogen and wherein A is selected from the radicals A2.94Na1 to A2.94Na420.

Table 215: Compounds of the formula I.a and their salts, wherein $R^1$ is ethyl, $R^2$ and $R^3$ are hydrogen and wherein A is selected from the radicals A2.94Nb1 to A2.94Nb420.

Table 216: Compounds of the formula I.a and their salts, wherein $R^1$ is ethyl, $R^2$ and $R^3$ are hydrogen and wherein A is selected from the radicals A2.94Nc1 to A2.94Nc420.

Further examples of these preferred embodiments are represented by the N-oxides of the preferred compounds according to the present invention as here above defined.

The compounds of the formula I, wherein $X^1$ is O and $X^3$ is a lone pair (compounds I.a), can be prepared e.g. according to the method depicted in scheme 1 by reacting an activated furan, thiophene or pyrrole carboxylic acid derivative III with a 3-aminopyridine compound IV (see e.g. Houben-Weyl: "Methoden der organ. Chemie" [Methods of Organic Chemistry], Georg-Thieme-Verlag, Stuttgart, N.Y. 1985, Volume E5, pp. 941-1045). Activated furan, thiophene or pyrrole carboxylic acid derivatives III are, for example, acyl halides, activated esters, anhydrides, acyl azides, wherein X is for example chlorine, fluorine, bromine, para-nitrophenoxy, pentafluorophenoxy, N-hydroxysuccinimides, hydroxybenzotriazol-1-yl. In scheme 1, the radicals A, $R^1$, $R^2$ and $R^3$ have the meanings mentioned above and in particular the meanings mentioned as being preferred.

Scheme 1:

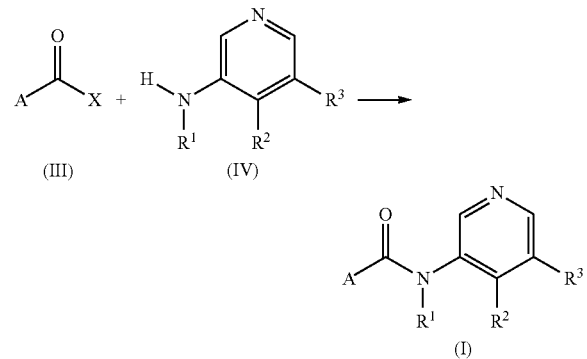

The compounds of the formula I, wherein $X^1$ is O and $X^3$ is a lone pair (compounds I.a), can also be prepared, for example, by reacting the furan, thiophene or pyrrole carboxylic acid V and the 3-aminopyridine compound IV, in the presence of a coupling agent according to scheme 2. In scheme 2, the radicals A, $R^1$, $R^2$ and $R^3$ have the meanings given above and in particular the meanings given as being preferred.

Scheme 2:

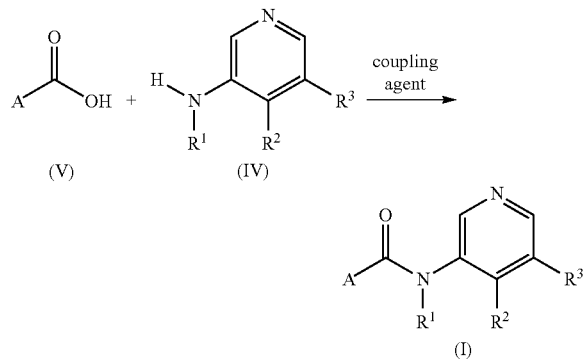

Suitable coupling agents are, for example:
coupling agents based on carbodiimides, for example N,N'-dicyclohexylcarbodiimide [J. C. Sheehan, G. P. Hess, J. Am. Chem. Soc. 1955, 77, 1067], N-(3-dimethylaminopropyl)-N'-ethylcarbodiimide;

coupling agents which form mixed anhydrides with carbonic esters, for example 2-ethoxy-1-ethoxycarbonyl-1,2-dihydroquinoline [B. Belleau, G. Malek, J. Amer. Chem. Soc. 1968, 90, 1651], 2-isobutyloxy-1-isobutyloxycarbonyl-1,2-dihydroquinoline [Y. Kiso, H. Yajima, J. Chem. Soc., Chem. Commun. 1972, 942];

coupling agents based on phosphonium salts, for example (benzotriazol-1-yloxy)tris(dimethylamino)phosphonium hexafluorophosphate [B. Castro, J. R. Domoy, G. Evin, C. Selye, Tetrahedron Lett. 1975, 14, 1219], (benzotriazol-1-yl-oxy)tripyrrolidinophosphonium hexafluorophosphate [J. Coste et al., Tetrahedron Lett. 1990, 31, 205];

coupling agents based on uronium salts or having a guanidinium N-oxide structure, for example N,N,N',N'-tetramethyl-O-(1H-benzotriazol-1-yl)uronium hexafluorophosphate [R. Knorr, A. Trzeciak, W. Bannwarth, D. Gillessen, Tetrahedron Lett. 1989, 30, 1927], N,N,N',N'-tetramethyl-O-(benzotriazol-1-yl)uronium tetrafluoroborate, (benzotriazol-1-yloxy)dipiperidinocarbenium hexafluorophosphate [S. Chen, J. Xu, Tetrahedron Lett. 1992, 33, 647];

coupling agents which form acid chlorides, for example bis-(2-oxo-oxazolidinyl)phosphinic chloride [J. Diago-Mesequer, Synthesis 1980, 547].

Compounds of formula I, wherein $X^1$ is O and $X^3$ is a lone pair (compounds I.a) and $R^1$ is different from hydrogen can also be prepared by alkylating the amides I (in which $R^1$ is hydrogen and which can be obtained according to scheme 1 or 2) using suitable alkylating agents in the presence of bases.

Scheme 3:

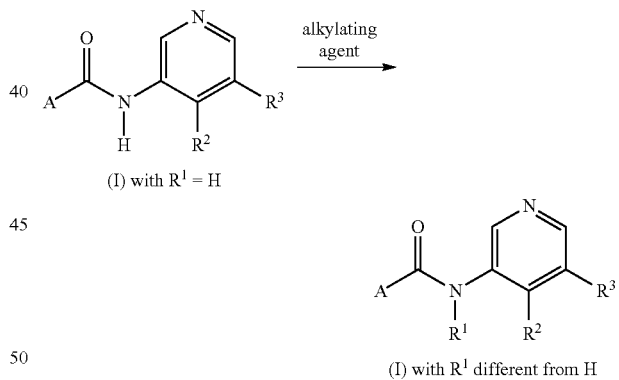

The furan, thiophene or pyrrole carboxylic acids V and their activated derivatives III as well as 3-aminopyridine-compounds IV are known in the art or are commercially available or can be prepared by methods known from the literature.

Compounds of the formula I, wherein $X^1$ is different from oxygen, can be prepared from the compounds of formula I.a by standard methods:

Compounds of the formula I, wherein $X^1$ is S, can be prepared e.g. by reacting a compound of formula I.a with 2,4-bis(4-methoxyphenyl)-1,3,2,4-dithiadiphosphetane-2,4-disulfide or phosphorus pentasulfide according to the method described by M. Jesberger et al. in Synthesis 2003, 1929.

Compounds of the formula I, wherein $X^1$ is $NR^{1a}$, can be prepared e.g. by reacting a compound I.a with 2,4-bis(4- methoxyphenyl)-1,3,2,4-dithiadiphosphetane-2,4-disulfide to obtain the corresponding thioamide (compound I, wherein $X^1$ is S) which is then reacted with an appropriate amine according to the method described by V. Glushkov et al. in Pharmaceutical Chemistry Journal 2005, 39(10), 533-536.

Compounds of formula II, wherein $X^2 = SR^{2d}$, can be prepared by alkylation of the corresponding thioamide (compound I, wherein $X^1$ is S) by reaction with an alkylating agent according to the method described by V. Glushkov et al. in Pharmaceutical Chemistry Journal 2005, 39(10), 533-536. Compounds II, wherein $X^2$ is $OR^{2a}$ or $NR^{2b}R^{2c}$, can be obtained in a similar manner. Compounds of the formula II, wherein $X^2 = SOR^{2d}$ or $SO_2R^{2d}$ can be obtained by oxidation of compounds II with $X^2 = SR^{2d}$.

N-oxides of the compounds of formulae I and II, can be prepared by oxidation of compounds I, according to standard methods of preparing heteroaromatic N-oxides, e.g. by the method described by C. Botteghi et al. in Journal of Organometallic Chemistry 1989, 370, 17-31.

As a rule, the compounds of formulae I or II can be prepared by the methods described above. If individual compounds can not be prepared via the above-described routes, they can be prepared by derivatization of other compounds I or II or by customary modifications of the synthesis routes described. For example, in individual cases, certain compounds I or II can advantageously be prepared from other compounds I or II by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the general formulae I or II may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formulae I or II or a salt or N-oxide thereof or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of formulae I or II or an agriculturally acceptable salt or N-oxide thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects preferably insects of the order Homoptera.

The invention further provides an agricultural composition for combating such invertebrate pests, which comprises such an amount of at least one compound of the general formulae I or II or at least one agriculturally useful salt or N-oxide thereof and at least one inert liquid and/or solid agronomically acceptable carrier that has a pesticidal action and, if desired, at least one surfactant.

Such a composition may contain a single active compound of the formulae I or II or a salt or N-oxide thereof or a mixture of several active compounds I or II or their salts according to the present invention. The composition according to the present invention may comprise an individual isomer or mixtures of isomers as well as individual tautomers or mixtures of tautomers.

The compounds of the formulae I or II and the pesticidical compositions comprising them are effective agents for controlling arthropod pests and nematodes. Invertebrate pests controlled by the compounds of formulae I or II include for example insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholithai funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus,*

*Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya* hominivorax, *Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribisnigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodoros moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* siphonatera, e.g. *Xenopsylla cheopsis, Ceratophyllus* spp.

The compositions and compounds of formulae I or II are useful for the control of nematodes, especially plant parasitic nematodes such as root knot nematodes, *Meloidogyne* hapla, *Meloidogyne incognita, Meloidogyne javanica,* and other *Meloidogyne* species;

cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formulae I or II are used for controlling insects or arachnids, in particular insects of the orders Lepidoptera, Coleoptera, Thysanoptera and Homoptera and arachnids of the order Acarina. The compounds of the formulae I or II according to the present invention are particularly useful for controlling insects of the order Thysanoptera and Homoptera.

The compounds of formula formulae I or II or the pesticidal compositions comprising them may be used to protect growing plants and crops from attack or infestation by invertebrate pests, especially insects, acaridae or arachnids by contacting the plant/crop with a pesticidally effective amount of compounds of formulae I or II. The term "crop" refers both to growing and harvested crops.

The compounds of formulae I or II can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineers Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are ligninsulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulphates, alkylsulfonates, fatty alcohol sulfates, fatty acids and sulphated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybute-nes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2- to 10-fold leading to concentrations in the ready to use preparations of 0.01 to 60% by weight active compound by weight, preferably 0.1 to 40% by weight.

The compounds of formulae I or II can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wetable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.

A) Water-soluble concentrates (SL, LS)

10 parts by weight of the active compound(s) are dissolved in 90 parts by weight of water or a water-soluble solvent. As an alternative, wetting agents or other auxiliaries are added. The active compound(s) dissolves upon dilution with water, whereby a formulation with 10% (w/w) of active compound(s) is obtained.

B) Dispersible concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetting agents and 70 parts by weight of water or of an organic solvent to give a fine active compound(s) suspension. Dilution with water gives a stable suspension of the active compound, whereby a formulation with 20% (w/w) of active compound(s) is obtained.

F) Water-dispersible granules and water-soluble granules (WG, SG)

50 parts by weight of the active compound(s) are ground finely with addition of 50 parts by weight of dispersants and wetting agents and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-dispersible powders and water-soluble powders (WP, SP, SS, WS)

75 parts by weight of the active compound(s) are ground in a rotor-stator mill with addition of 25 parts by weight of dispersants, wetting agents and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formulae I or II are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1 to 800 g/l of active ingredient, 1 to 200 g/l surfactant, 0 to 200 g/l antifreezing agent, 0 to 400 g/l of binder, 0 to 200 g/l of a pigment and up to 1 liter of a solvent, preferably water.

Other preferred FS formulations of compounds of formulae I or II for seed treatment comprise from 0.5 to 80% wt of the active ingredient, from 0.05 to 5% wt of a wetting agent, from 0.5 to 15% wt of a dispersing agent, from 0.1 to 5% wt of a thickener, from 5 to 20% wt of an anti-freeze agent, from 0.1 to 2% wt of an anti-foam agent, from 1 to 20% wt of a pigment and/or a dye, from 0 to 15% wt of a sticker/adhesion agent, from 0 to 75% wt of a filler/vehicle, and from 0.01 to 1% wt of a preservative.

Various types of oils, wetting agents, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formulae I or II are effective through both contact (via soil, glass, wall, bed net, carpet, plant parts or animal parts), and ingestion (bait, or plant part).

For use against ants, termites, wasps, flies, mosquitoes, crickets, or cockroaches, compounds of formulae I or II are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spraying devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formulae I or II as aerosols (e.g. in spray cans), oil sprays or pump sprays are highly suitable for the non-professional user for controlling pests such as flies, fleas, ticks, mosquitos or cockroaches. Aerosol recipes are preferably com-posed of the active compound, solvents such as lower alcohols (e.g. methanol, ethanol, propanol, butanol), ketones (e.g. acetone, methyl ethyl ketone), paraffin hydrocar-bons (e.g. kerosenes) having boiling ranges of approximately 50 to 250° C., dimethyl-formamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3 to 7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formulae I or II and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formulae I or II and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the active compounds of formulae I or II or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formulae I or II into contact with each other, and "seed dressing" to methods of seed treatment which provide the seeds with an amount of the compounds of formulae I or II, i.e. which generate a seed comprising the compound of formulae I or II. In principle, the treatment can be applied to the seed at any time from the harvest of the seed to the sowing of the seed. The seed can be treated immediately before, or during, the planting of the seed, for example using the "planters box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formulae I or II or the enantiomers diastereomers or veterinarily acceptable salts thereof are in particular also suitable for being used for combating parasites in and on animals.

A further object of the present invention is therefore also to provide new methods for controlling parasites in and on animals. Another object of the invention is to provide safer pesticides for animals. Another object of the invention is further to provide pesticides for animals that may be used in lower doses than existing pesticides. An another object of the invention is to provide pesticides for animals, which provide a long residual control of the parasites.

The invention also relates to compositions containing a parasiticidally effective amount of compounds of formulae I or II or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of compounds of formulae I or II or the enantiomers or veterinarily acceptable salts thereof and an acceptable carrier or a composition comprising it.

The present invention also provides a non-therapeutic method for treating, controlling, preventing and protecting animals against infestation and infection by parasites, which comprises applying to a locus-P a parasiticidally effective amount of a compound of formulae I or II or the enantiomers or veterinarily acceptable salts thereof and an acceptable carrier or a composition comprising it.

The invention also provides a process for the preparation of a composition for treating, controlling, preventing or protecting animals against infestation or infection by parasites which comprises including a parasiticidally effective amount of a compound of formulae I or II or the enantiomers or veterinarily acceptable salts thereof and an acceptable carrier or a composition comprising it.

The invention relates further to the use of compounds of formulae I or II for treating, controlling, preventing or protecting animals against infestation or infection by parasites.

The invention relates also to the use of a compound of formulae I or II or the enantiomers or veterinarily acceptable salts thereof and an acceptable carrier or a composition comprising it, for the manufacture of a medicament for the therapeutic treatment of animals against infections or infestations by parasites.

Activity of compounds against agricultural pests does not suggest their suitability for control of endo- and ectoparasites in and on animals which requires, for example, low, nonemetic dosages in the case of oral application, metabolic compatibility with the animal, low toxicity, and a safe handling.

Surprisingly, it has been found that compounds of formulae I or II are suitable for combating endo- and ectoparasites in and on animals. The compounds of formulae I or II or the enantiomers or veterinarily acceptable salts thereof and compositions comprising them are suitable for systemic and/or non-systemic control of ecto- and/or endoparasites. They are active against all or some stages of development.

Compounds of formulae I or II or the enantiomers or veterinarily acceptable salts thereof and compositions comprising them are preferably used for controlling and preventing infestations and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formulae I or II or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formulae I or II are especially useful for combating ectoparasites.

The compounds of formulae I or II are especially useful for combating endoparasites.

The compounds of formulae I or II are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*, ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*,

*Actinedida* (Prostigmata) and *Acaridida* (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm),

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formulae I or II and compositions containing them are particularly useful for the control of pests from the orders Diptera, Siphonaptera and Ixodida.

Moreover, the use of the compounds of formulae I or II and compositions containing them for combating mosquitoes is especially preferred.

The use of the compounds of formulae I or II and compositions containing them for combating flies is a further preferred embodiment of the present invention.

Furthermore, the use of the compounds of formulae I or II and compositions containing them for combating fleas is especially preferred.

The use of the compounds of formulae I or II and compositions containing them for combating ticks is a further preferred embodiment of the present invention.

The compounds of formulae I or II and compositions containing them also are especially useful for combating endoparasites (roundworms nematoda, thorny headed worms and planarians).

The compounds of formulae I or II and compositions containing them can be effective through both contact (via soil, glass, wall, bed net, carpet, blankets or animal parts) and ingestion (e.g. baits).

The present invention relates to the therapeutic and the non-therapeutic use of compounds of formulae I or II and compositions containing them for controlling and/or combating parasites in and/or on animals.

The compounds of formulae I or II and compositions containing them may be used to protect the animals from attack or infestation by parasites by contacting them with a parasitically effective amount of compounds of formulae I or II and compositions containing them.

As such, "contacting" includes both direct contact (applying the pesticidal mixtures/compositions containing the compounds of formulae I or II according to the present invention directly on the parasite, which may include an indirect contact at its locus-P, and optionally also administrating the pesticidal mixtures/composition directly on the animal to be protected) and indirect contact (applying the compounds/compositions to the locus of the parasite). The contact of the parasite through application to its locus is an example of a non-therapeutic use of compounds of formulae I or II.

"Locus-P" as used above means the habitat, food supply, breeding ground, area, material or environment in which a parasite is growing or may grow outside of the animal. The compounds of the invention can also be applied preventively to places at which occurrence of the pests or parasites are expected.

The compounds of formulae I or II can be effective through both contact (via soil, glass, wall, bed net, carpet, blankets or animal parts) and ingestion (e.g. baits).

Administration can be carried out prophylactically, therapeutically or non-therapeutically.

Administration of the active compounds is carried out directly or in the form of suitable preparations, orally, topically/dermally or parenterally.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally it is favorable to apply the compounds of formulae I or II in total amounts of 0.5 mg/kg to 100 mg/kg per day, preferably 1 mg/kg to 50 mg/kg per day.

Formulations

For oral administration to warm-blooded animals, the compounds of formulae I or II may be formulated as animal feeds, animal feed premixes, animal feed concentrates, pills, solutions, pastes, suspensions, drenches, gels, tablets, boluses and capsules. In addition, the compounds of formulae I or II may be administered to the animals in their drinking water. For oral administration, the dosage form chosen should provide the animal with 0.01 mg/kg to 100 mg/kg of animal body weight per day of the formulae I or II compound, preferably with 0.5 mg/kg to 100 mg/kg of animal body weight per day.

Alternatively, the compounds of formulae I or II may be administered to animals parenterally, for example, by intraruminal, intramuscular, intravenous or subcutaneous injection. The compounds of formulae I or II may be dispersed or dissolved in a physiologically acceptable carrier for subcutaneous injection. Alternatively, the compounds of formulae I or II may be formulated into an implant for subcutaneous administration. In addition the compounds of formulae I or II may be transdermally administered to animals. For parenteral administration, the dosage form chosen should provide the animal with 0.01 mg/kg to 100 mg/kg of animal body weight per day of the compounds of formulae I or II.

The compounds of formulae I or II may also be applied topically to the animals in the form of dips, dusts, powders, collars, medallions, sprays, shampoos, spot-on and pour-on formulations and in ointments or oil-in-water or water-in-oil emulsions. For topical applica-tion, dips and sprays usually contain 0.5 ppm to 5 000 ppm and preferably 1 ppm to 3 000 ppm of the compounds of formulae I or II. In addition, the compounds of formulae I or II may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels; Emulsions and suspensions for oral or dermal administration; semi-solid preparations; Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile. Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above. Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, N-alkylpyrrolidones such as N-methylpyrrolidone, N-butylpyrrolidone or N-octylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, °leyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether; ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride. Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures. Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity. For the production of solid preparations, the active compound is mixed with suitable excipients, if appropriate with addition of auxiliaries, and brought into the desired form. Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches. Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formulae I or II. Generally, it is favorable to apply the compounds of formulae I or II in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80% by weight, preferably from 0.1 to 65% by weight, more preferably from 1 to 50% by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formulae I or II against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formulae I or II are applied dermally/topically.

In a further preferred embodiment, the topical application is conducted in the form of compound-containing shaped articles such as collars, medallions, ear tags, bands for fixing at body parts, and adhesive strips and foils.

Generally, it is favorable to apply solid formulations which release compounds of formulae I or II in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formulae I or II. A detailed list of plastics and elastomers as well as preparation procedures for the shaped articles is given e.g. in WO 03/086075.

The active compounds can be applied solely or in a mixture with synergists or with other active compounds which act against pathogenic endo- and ectoparasites. For example, the active compounds of formulae I or II can be applied in mixtures with synthetic coccidiosis compounds, polyetherantibiotics as Amprolium, Robenidin, Toltrazuril, Monensin, Salinomycin, Maduramicin, Lasalocid, Narasin or Semduramicin or with other pesticides which are described in the list M below.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formulae I or II or the compositions comprising them in the use form as pesticides with other pesticides frequently results in a broader pesticidal spectrum of action.

The following list M of pesticides together with which the compounds of formulae I or II the invention can be used and with which potential synergistic effects might be produced, is intended to illustrate the possible combinations, but not to impose any limitation:

M.1. Organo(thio)phosphates compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zetacypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonists: amitraz;

M.21. Ryanodine receptor modulators: flubendiamide; (R)-,(S)-3-Chlor-N1-{2-methyl-4-[1,2,2,2-tetrafluor-1-(trifluormethyl)ethyl]phenyl}-N2-(1-methyl-2-methylsulfonyl-ethyl)phthalamid (M21.1);

M.22. Isoxazoline, 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4) and 4-[5-(3,5-Dichlorophenyl)-5-trifluoromethyl-4,5-dihydro-isoxazol-3-yl]-N-[(methoxyimino)methyl]-2-methylbenzamide (M22.5), 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6); 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M22.8);

M.23. Anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-

2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malonitrile compounds: 2-(2,2,3,3,4,4,5,5-octafluoropentyl)-2-(3,3,3-trifluoropropyl)malononitrile ($CF_2H$—$CF_2$—$CF_2$—$CF_2$—$CH_2$—$C(CN)_2$—$CH_2$—$CH_2$—$CF_3$) (M24.1) and 2-(2,2,3,3,4,4,5,5-octafluoropentyl)-2-(3,3,4,4,4-pentafluorobutyl)-malonodinitrile ($CF_2H$—$CF_2$—$CF_2$—$CF_2$—$CH_2$—$C(CN)_2$—$CH_2$—$CH_2$—$CF_2$—$CF_3$) (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds:
4-{[(6-Bromopyrid-3-yl)methyl](2-fluoroethyl)amino}furan-2(5H)-on (M26.),
4-{[(6-Fluoropyrid-3-yl)methyl](2,2-difluoroethyl)amino}furan-2(5H)-on (M26.2),
4-{[(2-Chloro-1,3-thiazolo-5-yl)methyl](2-fluoroethyl)amino}furan-2(5H)-on (M26.3),
4-{[(6-Chloropyrid-3-yl)methyl](2-fluoroethyl)amino}furan-2(5H)-on (M26.4),
4-{[(6-Chloropyrid-3-yl)methyl](2,2-difluoroethyl)amino}furan-2(5H)-on (M26.5),
4-{[(6-Chloro-5-fluoropyrid-3-yl)methyl](methyl)amino}furan-2(5H)-on (M26.6),
4-{[(5,6-Dichloropyrid-3-yl)methyl](2-fluoroethyl)amino}furan-2(5H)-on (M26.7),
4-{[(6-Chloro-5-fluoropyrid-3-yl)methyl](cyclopropyl)amino}furan-2(5H)-on),
4-{[(6-Chloropyrid-3-yl)methyl](cyclopropyl)amino}furan-2(5H)-on (M26.9) and
4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 14th Edition, British Crop Protection Council (2006) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779. AKD 1022 and its preparation have been described in U.S. Pat. No. 6,300,348. The compounds (M22.6) and (M22.7) are known from WO 2009/126668 and the compound (M22.8) is known from WO 2009/051956. The anthranilamides M23.1 to M23.6 have been described in WO 2008/72743 and WO 2008/72783, those M23.7 to M23.12 in WO 2007/043677. The phthalamide M 21.1 is known from WO 2007/101540. The alkynylether compound M27.1 is described e.g. in JP 2006/131529. Organic sulfur compounds have been described in WO 2007/060839. The isoxazoline compounds M 22.1 to M 22.5 have been described in e.g. WO 2005/085216, WO 2007/079162 and WO 2007/026965 The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 2002/089579, WO 2002/090320, WO 2002/090321, WO 2004/006677, WO 2005/068423, WO 2005/068432 and WO 2005/063694.

Fungicidal mixing partners are in particular those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-5-methyl, benthiavalicarb, carpropamid, chlorothalonil, cyflufenamid, cymoxanil, diclomezin, diclocymet, diethofencarb, edifen-phos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, enestroburin, fluoxastrobin, kresoxim-methyl, me-tominostrobin, orysastrobin, picoxystrobin, pyraclostrobin, pyribencarb or trifloxystrobin,
sulfenic acid derivatives such as captafol, captan, dichlofluanid, folpet, tolylfluanid, cinnemamides and analogs such as dimethomorph, flumetover or flumorph.

The invertebrate pest, i.e. arthropodes and nematodes, the plant, soil or water in which the plant is growing can be contacted with the compound(s) of formulae I or II or composition(s) containing them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

Moreover, invertebrate pests may be controlled by contacting the target pest, its food supply, habitat, breeding ground or its locus with a pesticidally effective amount of compounds of formulae I or II. As such, the application may be carried out before or after the infection of the locus, growing crops, or harvested crops by the pest.

"Locus" in general means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formulae I or II and the compositions comprising said compounds can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formulae I or II can also be applied preventively to places at which occurrence of the pests is expected.

The compounds of formulae I or II may also be used to protect growing plants from attack or infestation by pests by contacting the plant with a pesticidally effective amount of compounds of formulae I or II. As such, "contacting the plant" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m2.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 5 g to 600 g per hectare, more desirably from 10 g to 300 g per hectare.

In the treatment of seed, the application rates of the active ingredients are generally from 0.1 g to 10 kg per 100 kg of seed, preferably from 1 g to 1 kg per 100 kg of seed, in particular from 1 g to 250 g per 100 kg of seed, in particular from 10 g to 150 g per 100 kg of seed.

The present invention is now illustrated in further detail by the following examples. However, the purpose of the following examples is only illustrative and is not intended to limit the present invention to them.

I. PREPARATION EXAMPLES

The procedure described in the following synthesis example was used to prepare further compounds of the formula I by appropriate modification of the starting material. The resulting compounds, together with physical data, are listed below in Table I.

Products were characterized by melting point determination, by NMR spectroscopy or by the masses ([m/z]) or retention times (r.t.; [min]) determined via HPLC-MS (High Performance Liquid Chromatography Mass Spectrometry).

HPLC was carried out using an analytic RP-18 column (Chromolith® Speed ROD from Merck KgaA, Germany), 50×4.6 mm, which was operated at 40° C. The mobile phase consisted of acetonitrile with 0.1% by volume of trifluoroacetic acid (TFA) and an aqueous solution of TFA (0.1% by volume), using a gradient of 5:95 to 100:0 (vol/vol) over 5 minutes at a flow rate of 1.8 mL/min.

HPLC for examples 42, 46 and 47 was carried out using an analytic RP-18 column (Kinetex™ XB C18, 1.7 µm, from Phenomenex, Germany), 50×2.0 mm, which was operated at 60° C. The mobile phase consisted of acetonitrile with 0.1% by volume of TFA and an aqueous solution of TFA (0.1% by volume), using a gradient 5:95 to 100:0 (vol/vol) over 1.5 minutes at a flow rate of 0.8 mL/min to 1.0 mL/min.

MS analyses were performed using quadrupole electrospray ionization, 80 V (positive mode).

Example 28

2,5-Dichloro-thiophene-3-carboxylic acid methyl-pyridin-3-yl-amide 394 mg (2.0 mmol, 1.0 equiv.) of 2,5-dichloro-thiophene-3-carboxylic acid were dissolved in 8 ml of dichloromethane and 254 mg (2.0 mmol, 1.0 equiv.) of oxalyl chloride were added dropwise. A catalytic amount of N,N-dimethylformamide (DMF) (5 drops) was added and the reaction mixture was stirred at room temperature for 4 h. Then, the mixture was added dropwise to a solution of 300 mg (3.0 mmol, 1.5 equiv) of triethylamine and 217 mg (2.0 mmol, 1.0 equiv.) of methyl-pyridin-3-yl-amine in 6 ml of dichloromethane and the reaction was stirred at room temperature overnight. Water was added and the mixture was extracted with dichloromethane. The combined organic phases were dried over $Na_2SO_4$, filtered and the solvent was removed under reduced pressure to yield 371 mg of the title compound (65%, 95% purity), [Mt]: 288.1.

The procedure described in the synthesis example above was used to prepare further compounds by appropriate modification of the starting compounds. The compounds thus obtained are listed in table I below, together with physico-chemical data.

TABLE I

Compounds of formula I.a with $R^2 = R^3 = H$:

(I.a)

| Ex. | A | $R^1$ | r.t. [min] [a] | m/z [b] | M[g/mol] |
|---|---|---|---|---|---|
| 1 | 5-Chloro-thiophen-2-yl | H | 2.078 | 238.9 | 238.7 |
| 2 | 5-(4-Isopropyl-phenoxymethyl)-furan-2-yl | H | 2.998 | 337.1 | 336.4 |
| 3 | 5-Bromo-furan-2-yl | H | 1.710 | 268.9 | 267.1 |
| 4 | 3-Chloro-thiophen-2-yl | H | 1.702 | 239.0 | 238.7 |
| 5 | Furan-2-yl | H | 1.293 | 189.0 | 188.2 |
| 6 | 5-Nitro-furan-2-yl | H | 1.492 | 234.0 | 233.2 |
| 7 | 3-Trifluoromethyl-thiophen-2-yl | H | 1.947 | 273.0 | 272.3 |
| 8 | 3-Bromo-thiophen-2-yl | H | 1.768 | 284.9 | 283.2 |
| 9 | 4-Bromo-thiophen-2-yl | H | 2.027 | 284.9 | 283.2 |
| 10 | 5-Trifluoromethyl-thiophen-2-yl | H | 2.374 | 273.0 | 272.3 |
| 11 | 1-Methyl-1H-pyrrol-2-yl | H | 1.613 | 202.1 | 201.2 |
| 12 | 1H-Pyrrol-2-yl | H | 1.330 | 188.0 | 187.2 |
| 13 | 3-Chloro-thiophen-2-yl | $CH_3$ | 1.719 | 253.0 | 252.7 |
| 14 | 1-Methyl-1H-pyrrol-2-yl | $CH_3$ | 1.504 | 216.1 | 215.3 |
| 15 | 3-Methyl-furan-2-yl | $CH_3$ | 1.569 | 217.1 | 216.2 |
| 16 | 5-Chloro-thiophen-2-yl | $CH_3$ | 2.103 | 253.0 | 252.7 |
| 17 | 2-Methyl-furan-3-yl | H | 1.664 | 203.0 | 202.2 |
| 18 | Thiophen-3-yl | H | 1.544 | 205.0 | 204.3 |
| 19 | 2,5-Dimethyl-furan-3-yl | H | 1.953 | 217.1 | 216.2 |
| 20 | 2-Bromo-thiophen-3-yl | H | 1.820 | 284.9 | 283.1 |
| 21 | 2-Chloro-thiophen-3-yl | H | 1.759 | 238.9 | 238.7 |
| 22 | 2,5-Dichloro-thiophen-3-yl | H | 2.181 | 272.9 | 273.1 |
| 23 | 5-Methyl-thiophen-3-yl | H | 1.869 | 219.0 | 218.3 |
| 24 | 5-Isopropyl-thiophen-3-yl | H | 2.389 | 247.0 | 246.3 |
| 25 | 2,5-Dimethyl-thiophen-3-yl | H | 2.121 | 233.0 | 232.3 |
| 26 | 4-Trifluoromethyl-thiophen-3-yl | H | 1.933 | 273.0 | 272.3 |
| 27 | 5-Nitro-thiophen-3-yl | $CH_3$ | 1.702 | 264.0 | 263.3 |
| 28 | 2,5-Dichloro-thiophen-3-yl | $CH_3$ | 2.233 | 286.9 | 287.2 |
| 29 | Furan-3-yl | $CH_3$ | 1.146 | 203.0 | 202.2 |
| 30 | 2-Methyl-furan-3-yl | $CH_3$ | 1.483 | 217.0 | 216.2 |
| 31 | 5-Methyl-2-trifluoromethyl-furan-3-yl | $CH_3$ | 2.248 | 285.0 | 284.2 |
| 32 | Thiophen-3-yl | $CH_3$ | 1.389 | 219.0 | 218.3 |
| 33 | 2,5-Dimethyl-furan-3-yl | $CH_3$ | 1.775 | 231.1 | 230.3 |
| 34 | 5-(4-tert-Butyl-phenoxymethyl)-furan-2-yl | H | 3.145 | 351.1 | 350.4 |
| 35 | 5-Nitro-furan-2-yl | H | 1.432 | 234.0 | 233.2 |
| 36 | 5-Benzoyl-furan-2-yl | H | 2.173 | 293.1 | 292.3 |
| 37 | Furan-2-yl | H | 1.242 | 189.0 | 188.2 |
| 38 | 5-(3,5-Dimethyl-pyrazol-1-ylmethyl)-furan-2-yl | H | 1.857 | 297.1 | 296.3 |
| 39 | 5-(2-Nitro-phenoxymethyl)-furan-2-yl | H | 2.278 | 340.0 | 339.3 |
| 40 | 5-(4-Chloro-phenyl)-2-trifluoromethyl-furan-3-yl | H | 3.125 | 367.0 | 366.7 |
| 41 | 5-(4-Ethoxy-phenoxymethyl)-furan-2-yl | H | 2.533 | 339.1 | 338.4 |
| 42 | 5-(2,5-Dichloro-phenyl)-furan-2-yl | H | 1.227 | 338.0 | 333.2 |
| 43 | 5-(4-Chloro-phenyl)-furan-2-yl | H | 2.606 | 299.0 | 298.7 |
| 44 | 5-(2-Methoxy-4-nitro-phenyl)-furan-2-yl | H | 2.537 | 340.0 | 339.3 |
| 45 | 4-Acetyl-3,5-dimethyl-1H-pyrrole-2-yl | H | 1.640 | 258.1 | 257.3 |
| 46 | 3-Methoxy-thiophene-2-yl | H | 0.706 | 235.0 | 234.3 |
| 47 | 5-Nitro-thiophene-2-yl | H | 0.754 | 250.0 | 249.3 |
| 48 | 2-Difluoromethoxy-thiophene-3-yl | H | 1.858 | 271.0 | 270.3 |
| 49 | 3-Ethoxy-5-methyl-thiophene-2-yl | H | 1.443 | 262.3 | 262.3 |
| 50 | 3-Methyl-thiophene-2-yl | H | 1.728 | 219.0 | 218.3 |
| 51 | 5-Bromo-furan-2-yl | $CH_3$ | 1.676 | 282.7 | 281.1 |
| 52 | Furan-2-yl | $CH_3$ | 1.142 | 203.1 | 202.2 |
| 53 | 5-Nitro-furan-2-yl | $CH_3$ | 1.381 | 248.1 | 247.2 |
| 54 | Thiophene-2-yl | $CH_3$ | 1.381 | 219.1 | 218.3 |
| 55 | 5-Nitro-thiophene-2-yl | $CH_3$ | 1.878 | 264.1 | 263.3 |
| 56 | 2-Difluoromethoxy-thiophene-3-yl | $CH_3$ | 1.650 | 285.1 | 284.3 |
| 57 | 2-Bromo-thiophene-3-yl | $CH_3$ | 1.703 | 299.0 | 297.2 |
| 58 | 2-Chloro-thiophene-3-yl | $CH_3$ | 1.667 | 252.9 | 252.7 |
| 59 | 5-Methyl-thiophene-2-yl | $CH_3$ | 1.744 | 233.1 | 232.3 |
| 60 | 3-Methoxy-thiophene-2-yl | $CH_3$ | 1.410 | 249.1 | 248.3 |
| 61 | 4-Bromo-thiophene-2- | $CH_3$ | 1.986 | 299.0 | 297.2 |
| 62 | 3-Bromo-thiophene-2-yl | $CH_3$ | 1.702 | 299.0 | 297.2 |
| 63 | 5-Bromo-thiophene-2-yl | $CH_3$ | 2.078 | 299.0 | 297.2 |
| 64 | 5-(3-Trifluoromethyl-phenyl)-furan-2-yl | $CH_3$ | 2.758 | 347.1 | 346.3 |

[a] r.t. = HPLC retention time
[b] m/z of the [M]+ peaks

II. EVALUATION OF PESTICIDAL ACTIVITY

II.1 Cotton Aphid (*Aphis gossypii*, Mixed Life Stages)

Method a)

The active compounds were formulated in 50:50 (vol/vol) acetone:water and 100 ppm Kinetica™ surfactant.

Cotton plants at the cotyledon stage (one plant per pot) were infested by placing a heavily infested leaf from the main colony on top of each cotyledon. The aphids were allowed to transfer to the host plant overnight, and the leaf used to transfer the aphids was removed. The cotyledons were dipped in the test solution and allowed to dry. After 5 days, mortality counts were made.

In this test, the compounds 1, 2, 3, 4, 9, 10, 17, 18, 19, 21, 23, 24 and 25, respectively, at 300 ppm showed a mortality of at least 75% in comparison with untreated controls.

Method b)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (vol/vol). A nonionic sur25 factant (Kinetic®) was included in the solution at a volume of 0.01% (vol/vol).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compound 26 at 300 ppm showed a mortality of at least 75% in comparison with untreated controls.

II.2 Green Peach Aphid (*Myzus persicae*, Mixed Life Stages)

Method a)

The active compounds were formulated in 50:50 (vol/vol) acetone:water and 100 ppm Kinetica™ surfactant.

Pepper plants in the $2^{nd}$ leaf-pair stage (variety 'California Wonder') were infested with approximately 40 laboratory-reared aphids by placing infested leaf sections on top of the test plants. The leaf sections were removed after 24 hr. The leaves of the intact plants were dipped into gradient solutions of the test compound and allowed to dry. Test plants were maintained under fluorescent light (24 hour photoperiod) at about 25° C. and 20-40% relative humidity. Aphid mortality on the treated plants, relative to mortality on check plants, was determined after 5 days.

In this test, compounds 18, 19 and 23, respectively, at 300 ppm showed a mortality of at least 90% in comparison with untreated controls.

Method b)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (vol/vol). A nonionic surfactant (Kinetic®) was included in the solution at a volume of 0.01% (vol/vol).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds 7, 26, 33 and 64, respectively, at 300 ppm showed a mortality of at least 75% in comparison with untreated controls.

II.3 Cowpea Aphid (*Aphis craccivora*)

The active compounds were formulated in 50:50 (vol/vol) acetone:water. The test solution was prepared at the day of use.

Potted cowpea plants colonized with 100-150 aphids of various stages were sprayed after the pest population had been recorded. Population reduction was assessed after 24, 72, and 120 hours.

In this test, the compounds 1, 7, 9, 11, 12, 17, 18, 19, 25, 30, 32, 45 and 64, respectively, at 300 ppm showed a mortality of at least 90% in comparison with untreated controls.

II.4 Vetch aphid (*Megoura viciae*)

The active compounds were formulated in 1:3 (vol/vol) DMSO:water with different concentrations of formulated compounds.

Bean leaf disks were placed into microtiterplates filled with 0.8% agar-agar and 2.5 ppm OPUS™. The leaf disks were sprayed with 2.5 µl of the test solution and 5 to 8 adult aphids were placed into the microtiterplates which were then closed and kept at 23±1° C. and 50±5% relative humidity under fluorescent light for 6 days. Mortality was assessed on the basis of vital, reproduced aphids. Aphid mortality and fecundity was then visually assessed.

In this test, the compounds 6, 8, 10, 11, 17, 18, 19, 20, 24, 25, 26, 30 and 33, respectively at a concentration of the test solution of 2500 mg/L showed a mortality of at least 90%.

II.5 Boll Weevil (*Anthonomus grandis*)

The compounds were formulated in 75:25 (vol/vol) water:DMSO.

For evaluating control of boll weevil (*Anthonomus grandis*) the test unit consisted of 24-well-microtiter plates containing an insect diet and 20-30 *A. grandis* eggs. Different concentrations of formulated compounds were sprayed onto the insect diet at 20 µl, using a custom built micro atomizer, at two replications. After application, the microtiter plates were incubated at 23±1° C. and 50±5% relative humidity for 5 days. Egg and larval mortality was then visually assessed.

In this test, the compounds 4, 5, 6, 11, 12, 13, 16, 19, 20, 21, 22, 26, 28, 29 and 45, respectively at a concentration of the test solution of 2500 mg/L showed a mortality of at least 50%.

II.6 Activity Against Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% (vol/vol) water and 25% (vol/vol) DMSO. Different concentrations of formulated compounds were pipetted into the aphid diet, using a custom built pipetter, at two replications. After application, 5 to 8 adult aphids were placed on the artificial membrane inside the microtiter plate wells. The aphids were then allowed to suck on the treated aphid diet and incubated at about 23+1° C. and about 50+5% relative humidity for 3 days. Aphid mortality and fecundity was then visually assessed.

In this test, compounds 9, 12, 15, 19, 24, 27, 30, 31, 33 and 45, respectively at 2500 ppm showed 100% mortality in comparison with untreated controls.

II.7 Activity Against Brown Planthopper (*Nilaparvata lugens*)

The active compounds were formulated as a 50:50 (vol/vol) acetone:water solution. Surfactant (Alkamuls EL 620) was added at the rate of 0.1% (vol/vol).

Rice seedlings were cleaned and washed 24 h before spraying. Potted rice seedlings were sprayed with 5 ml test solution, air dried, placed in cages and inoculated with 10 adults. Treated rice plants were kept at 28-29° C. and relative humidity of 50-60%. Percent mortality was recorded after 72 hours.

In this test, compound 14 at 500 ppm showed a mortality of at least 50% in comparison with untreated controls.

II.8 Silverleaf Whitefly (*Bemisia argentifolii*, Adult)

The active compounds were formulated in cyclohexanone as a 10,0000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (vol/vol). A nonionic surfactant (Kinetic®) was included in the solution at a volume of 0.01% (vol/vol).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days old) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compound 7 at 300 ppm showed a mortality of at least 75% in comparison with untreated controls.

The invention claimed is:

1. A method for controlling invertebrate pests which method comprises treating the pests, their food supply, their habitat or their breeding ground or a plant, seed, soil, area, material or environment in which the pests are growing or may grow, or the materials, plants, seeds, soils, surfaces or spaces to be protected from pest attack or infestation with a pesticidally effective amount of a compound of a 3-pyridyl compound of formula (I) or (II), a salt, an N-oxide, a tautomer, or the salt of the N-oxide or tautomer,

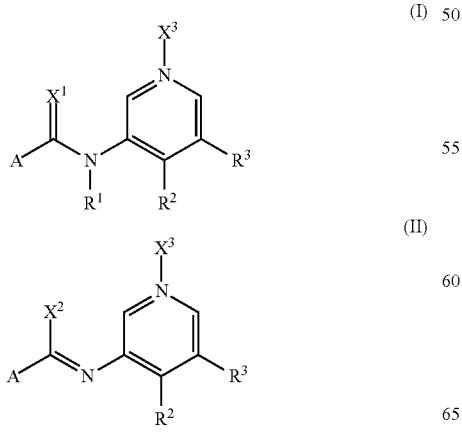

wherein
A is a radical of the formulae A1 or A2

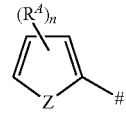

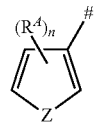

where # denotes the binding site to the remainder of formulae I and II
n is 0, 1, 2 or 3;
Z is O, S or N—$R^N$;
$R^A$ is selected from the group consisting of halogen, CN, $NO_2$, $C_1$-$C_{10}$-alkyl, $C_2$-$C_{10}$-alkenyl and $C_2$-$C_{10}$-alkynyl, wherein the last three mentioned radicals may be unsubstituted, may be partially or fully halogenated or may carry 1, 2 or 3 identical or different substituents $R^x$,
or from the group consisting of $OR^a$, $C(Y)R^b$, $C(Y)OR^c$, $S(O)_mR^d$, $NR^eR^f$, $C_3$-$C_{10}$-cycloalkyl, $C_5$-$C_{10}$-cycloalkenyl, heterocyclyl, phenyl, $C_3$-$C_{10}$-cycloalkyl-$C_1$-$C_5$-alkyl, $C_5$-$C_{10}$-cycloalkenyl-$C_1$-$C_5$-alkyl, heterocyclyl-$C_1$-$C_5$-alkyl, hetaryl-$C_1$-$C_5$-alkyl,
phenyl-$C_1$-$C_5$-alkyl and phenoxy-$C_1$-$C_5$-alkyl wherein the cyclic moieties of the ten last mentioned radicals may be unsubstituted or may carry 1, 2, 3, 4 or 5 identical or different substituents $R^y$; and
$R^N$ is selected from the group consisting of hydrogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$,
and also from the group consisting of $OR^a$, $C(Y)R^b$, $C(Y)OR^c$, $S(O)_mR^d$, $NR^eR^f$, $C(Y)NR^gR^h$, $S(O)_m$-$NR^eR^f$, $C(Y)NR^iNR^eR^f$, $C_1$-$C_5$-alkylen-$OR^a$, $C_1$-$C_5$-alkylen-CN, $C_1$-$C_5$-alkylen-$C(Y)R^b$, $C_1$-$C_5$-alkylen-$C(Y)OR^c$, $C_1$-$C_5$-alkylen-$NR^eR^f$, $C_1$-$C_5$-alkylen-$C(Y)NR^gR^h$, $C_1$-$C_5$-alkylen-$S(O)_mR^d$, $C_1$-$C_5$-alkylen-$S(O)_mNR^eR^f$, $C_1$-$C_5$-alkylen-$NR^iNR^eR^f$, $C_3$-$C_{10}$-cycloalkyl, $C_5$-$C_{10}$-cycloalkenyl, heterocyclyl, phenyl, $C_3$-$C_{10}$-cycloalkyl-$C_1$-$C_5$-alkyl, $C_5$-$C_{10}$-cycloalkenyl-$C_1$-$C_5$-alkyl, heterocyclyl-$C_1$-$C_5$-alkyl, hetaryl-$C_1$-$C_5$-alkyl, phenyl-$C_1$-$C_5$-alkyl and phenoxy-$C_1$-$C_5$-alkyl wherein the cyclic moieties of the ten last mentioned radicals may be unsubstituted or may carry 1, 2, 3, 4 or 5 identical or different substituents $R^y$;
and where
m is 0, 1 or 2
Y is O or S;
$X^1$ is S, O or $NR^{1a}$, where $R^{1a}$ is selected from hydrogen, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$X^2$ is $OR^{2a}$, $NR^{2b}R^{2c}$, $S(O)^m R^{2d}$, where $R^{2a}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^{2b}$, $R^{2c}$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, phenyl-$C_1$-$C_4$-alkyl and hetaryl-$C_1$-$C_4$-alkyl, wherein the aromatic ring in the eight last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^{2b}$ and $R^{2c}$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^{2d}$ is selected from $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, phenyl-$C_1$-$C_4$-alkyl and hetaryl-$C_1$-$C_4$-alkyl, wherein the aromatic ring in the four last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$X^3$ is a lone pair or oxygen;

$R^1$ is hydrogen, CN, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $OR^a$, $C(Y)R^b$, $C(Y)OR^c$, $S(O)_2R^d$, $NR^eR^f$, $C(Y)NR^gR^h$, $S(O)_m NR^eR^f$, $C(Y)NR^iNR^eR^f$, $C_1$-$C_5$-alkylen-$OR^a$, $C_1$-$C_5$-alkylen-CN, $C_1$-$C_5$-alkylen-$C(Y)R^b$, $C_1$-$C_5$-alkylen-$C(Y)OR^c$, $C_1$-$C_5$-alkylen-$NR^eR^f$, $C_1$-$C_5$-alkylen-$C(Y)NR^gR^h$, $C_1$-$C_5$-alkylen-$S(O)_2R^d$, $C_1$-$C_5$-alkylen-$S(O)_m NR^eR^d$, $C_1$-$C_5$-alkylen-$C(Y)NR^iNR^eR^f$, phenyl, hetaryl, $C_3$-$C_{10}$-cycloalkyl, heterocyclyl, phenyl-$C_1$-$C_5$-alkyl, hetaryl-$C_1$-$C_5$-alkyl, heterocyclyl-$C_1$-$C_5$-alkyl, $C_3$-$C_{10}$-cycloalkyl-$C_1$-$C_5$-alkyl and phenoxy-$C_1$-$C_5$-alkyl, wherein the rings of the nine last mentioned radicals may be unsubstituted or may carry 1, 2, 3, 4 or 5 identical or different substituents selected from the radicals $R^y$;

$R^2$ is hydrogen, halogen, methyl, $C_1$-haloalkyl, methoxy, $C_1$-haloalkoxy, methylthio, $C_1$-haloalkylthio, methylsulfinyl, $C_1$-haloalkylsulfinyl, methylsulfonyl or $C_1$-haloalkylsulfonyl;

$R^3$ is hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl or $C_1$-$C_4$-alkoxy-$C_1$-$C_4$-alkyl;

$R^a$, $R^b$, $R^c$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^g$, $R^h$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$- alkyl wherein the ring in the six last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^i$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^x$ are independently of each other selected from cyano, nitro, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_{10}$-alkylcarbonyl, $C_3$-$C_{10}$-cycloalkyl, 5- to 7-membered heterocyclyl, phenyl, $C_3$-$C_6$-cycloalkoxy, 3- to 6-membered heterocyclyloxy and phenoxy, wherein the last 6 mentioned radicals may be unsubstituted or may carry 1, 2, 3, 4 or 5 radicals selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^y$ is selected from halogen, cyano, nitro, $C_1$-$C_4$-alkyl, $C_1$-$C_4$-haloalkyl, $C_1$-$C_4$-alkoxy, $C_1$-$C_4$-haloalkoxy, $S(O)_m R^d$, $S(O)_m NR^e R^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_3$-$C_6$-cycloalkyl, 5- to 7-membered heterocyclyl, $C_3$-$C_6$-cycloalkoxy, 3- to 6-membered heterocyclyloxy, hetaryloxy and phenoxy, wherein the last 6 mentioned radicals may be unsubstituted or may carry 1, 2, 3, 4 or 5 radicals selected from halogen, cyano, nitro, $C_1$-$C_4$-alkyl, $C_1$-$C_4$-haloalkyl, $C_1$-$C_4$-alkoxy and $C_1$-$C_4$-haloalkoxy.

2. The method of claim 1, wherein the 3-pyridyl compound is a compound of the formula (I).

3. The method of claim 2, wherein $X^1$ in formula I is oxygen.

4. The method of claim 3, wherein $R^1$ of the compound of formula (I) is hydrogen, $C_1$-$C_{10}$-alkyl, $C_1$-$C_{10}$-haloalkyl, $C_1$-$C_4$-alkylene-CN, heterocyclyl-$C_1$-$C_5$-alkyl, hetaryl-$C_1$-$C_5$-alkyl, $C_1$-$C_5$-alkylen-$OR^a$ or $C_3$-$C_{10}$-cycloalkyl-$C_1$-$C_5$-alkyl.

5. The method of claim 4, wherein $R^1$ of the compound of formula I is hydrogen, $C_1$-$C_4$-alkyl, $C_1$-$C_4$-haloalkyl, $C_1$-$C_3$-alkylen-O—$C_1$-$C_3$-alkyl or $C_1$-$C_4$-alkylene-CN.

6. The method of claim 5, wherein $R^2$ of the compound of formulae I or II is hydrogen, fluorine, chlorine, bromine, methyl, difluoromethyl, trifluoromethyl, methoxy, difluoromethoxy or trifluoromethoxy.

7. The method of claim 6, wherein $R^3$ of the compound of formulae I or II is hydrogen, fluorine, chlorine, bromine, methyl, difluoromethyl, trifluoromethyl, methoxy, difluoromethoxy or trifluoromethoxy.

8. The method of claim 7, wherein at least one of the radicals $R^2$ or $R^3$ of the compound of formulae I or II is hydrogen.

9. The method of claim 7, wherein both radicals $R^2$ and $R^3$ of the compound of formulae I or II are hydrogen.

10. The method of claim 7, wherein A of the compound of formulae I or II is a radical A 1.

11. The method of claim 7, wherein A of the compound of formulae I or II is a radical A2.

12. The method of claim 7, wherein $R^A$ of the compound of formulae I or II, if present, is selected from the group consisting of halogen, CN, $NO_2$, $C_1$-$C_4$-alkyl, $C_1$-$C_4$-haloalkyl, $C_3$-$C_6$-cycloalkyl and $C_3$-$C_6$-halocycloalkyl.

13. The method of claim 7, wherein Z of the compound of formulae I or II is $NR^N$.

14. The method of claim 13, where $R^N$ of the compound of formulae I or II is selected from the group consisting of hydrogen, $C_1$-$C_6$-alkyl, $C_1$-$C_6$-haloalkyl, heterocyclyl-$C_1$-$C_4$-alkyl, $C_1$-$C_4$-alkoxy-$C_1$-$C_4$-alkyl, $C_1$-$C_4$-alkylene-CN, $C_3$-$C_6$-cycloalkyl, $C_3$-$C_6$-cycloalkyl-$C_1$-$C_4$-alkyl, where the cycloalkyl moiety in the last two mentioned radicals is unsubstituted or carries 1 or 2 radicals selected from halogen, CN and $C_1$-$C_2$-haloalkyl.

15. The method of claim 14, wherein Z of the compound of formulae I or II is O.

16. The method of claim 14, wherein Z of the compound of formulae I or II is S.

17. The method as claimed in claim 1, wherein the invertebrate pests are arthropod pests and/or nematodes.

18. The method as claimed in claim 1, wherein the invertebrate pests are insects.

19. The method as claimed in claim 18, wherein the invertebrate pests are insects of the order Homoptera.

* * * * *